United States Patent
Natan et al.

(10) Patent No.: US 6,242,264 B1
(45) Date of Patent: Jun. 5, 2001

(54) SELF-ASSEMBLED METAL COLLOID MONOLAYERS HAVING SIZE AND DENSITY GRADIENTS

(75) Inventors: Michael J. Natan, State College; Bonnie E. Baker, Collegeville, both of PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/254,142

(22) PCT Filed: Sep. 4, 1997

(86) PCT No.: PCT/US97/15581

§ 371 Date: Jan. 12, 2000

§ 102(e) Date: Jan. 12, 2000

(87) PCT Pub. No.: WO98/10289

PCT Pub. Date: Mar. 12, 1998

Related U.S. Application Data

(63) Continuation-in-part of application No. 08/769,970, filed on Dec. 19, 1996, now abandoned.
(60) Provisional application No. 60/025,064, filed on Sep. 4, 1996.

(51) Int. Cl.[7] .......................... G01N 21/65; G01N 33/48; G01N 33/50; G01N 33/553
(52) U.S. Cl. ..................... 436/171; 422/68.1; 422/82.01; 422/82.02; 422/82.03; 422/82.05; 422/82.08; 422/82.09; 436/86; 436/164; 436/501; 436/514; 436/525

(58) Field of Search .................. 204/415, 418; 422/82.01, 82.02, 82.03, 90, 98, 82.05, 82.09, 82.08, 68.1; 435/6; 436/86, 171, 501, 525, 514, 524, 536, 164

(56) References Cited

U.S. PATENT DOCUMENTS

| | | | |
|---|---|---|---|
| 4,334,880 | * 6/1982 | Malmros . | |
| 4,889,427 | * 12/1989 | Van Veen et al. | 422/82.05 X |
| 4,960,692 | * 10/1990 | Lentrichia et al. | 436/518 |
| 5,132,097 | * 7/1992 | Van Deusen et al. | 422/82.05 X |
| 5,137,827 | * 8/1992 | Mroczkowski et al. | 435/288 |
| 5,266,498 | 11/1993 | Tarcha et al. | 436/525 |
| 5,391,272 | * 2/1995 | O'Daly et al. | 204/153.12 |

OTHER PUBLICATIONS

R. L. Moody et al, Appl. Spectrosc> Jun. 1987, 41, 966–970.*
A. Doron et al, Langmuir 1995, 11, 1313–1317, Jun. 1987.*

* cited by examiner

*Primary Examiner*—Arlen Soderquist
(74) *Attorney, Agent, or Firm*—Swanson & Bratschun, LLC

(57) ABSTRACT

A biosensor based on complexes between biomolecule receptors and colloidal Au nanoparticles, and more specifically, colloid layers of receptor/Au complexes that can be used to detect biomolecule analytes through measuring of binding-induced changes in electrical resistance or surface plasmon resonance. Also disclosed is a method for detecting and analysing carrier-borne chemical compounds with Raman spectroscopy using an improved SERS substrate. Further disclosed is an improved method for detecting compounds in solvents using capillary electrophoresis in conjunction with Raman spectroscopy.

13 Claims, 55 Drawing Sheets

Scheme I

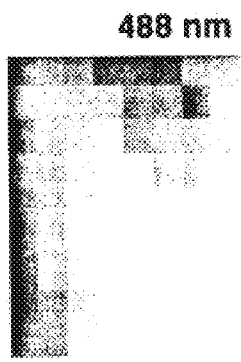
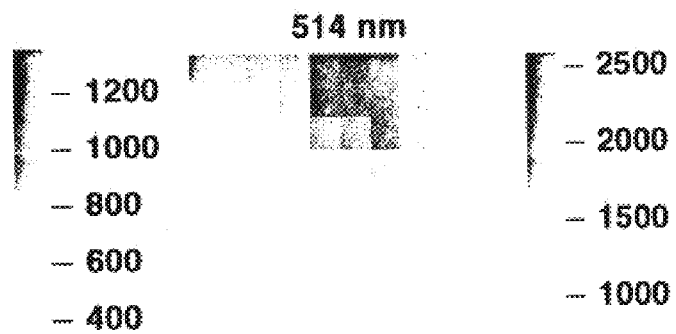
FIG. 43A
FIG. 43B
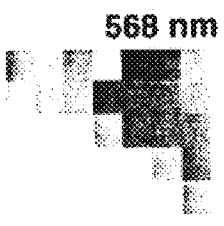
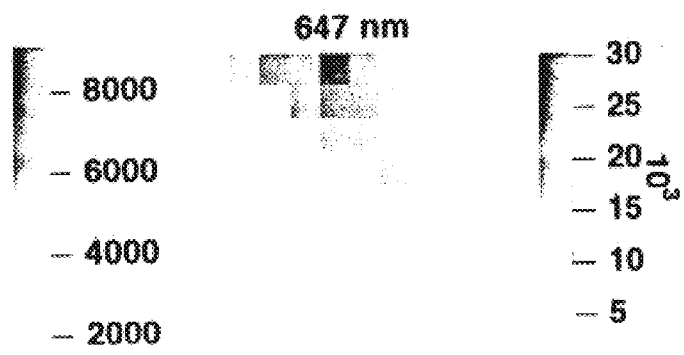
FIG. 43C
FIG. 43D

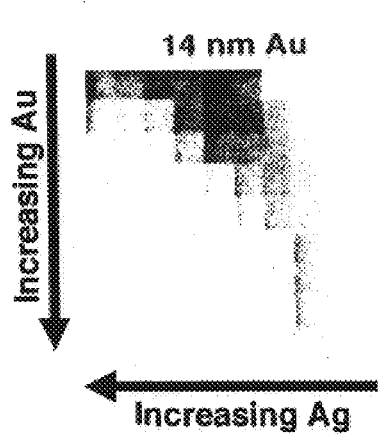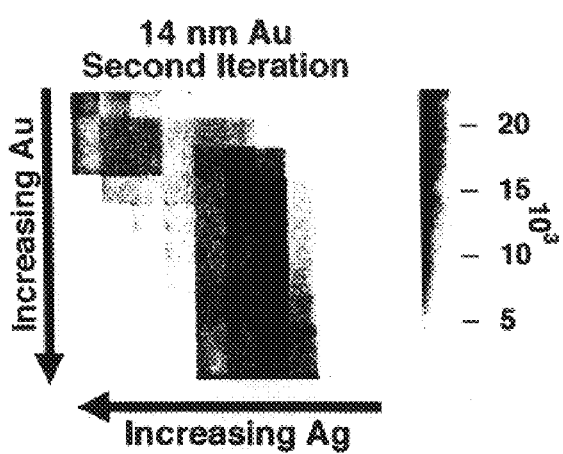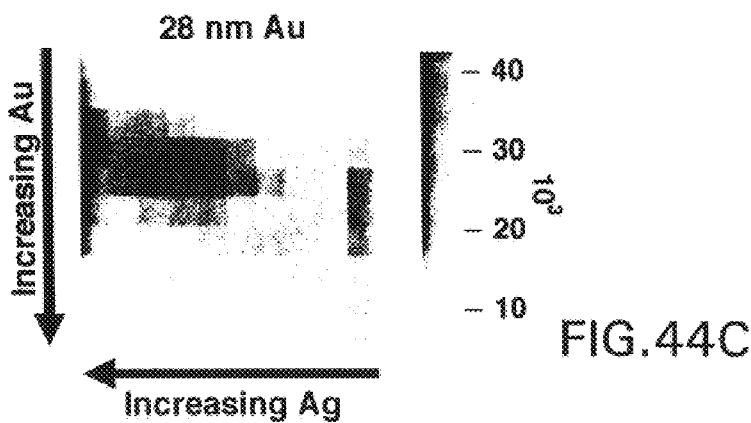
FIG. 44A
FIG. 44B
FIG. 44C $Ag_1$ 370 particles / micron$^2$
Ave. height = 29 nm $Ag_2$ 313 particles / micron$^2$
Ave. height = 38 nm $Ag_3$ 315 particles / micron$^2$
Ave. height = 41 nm

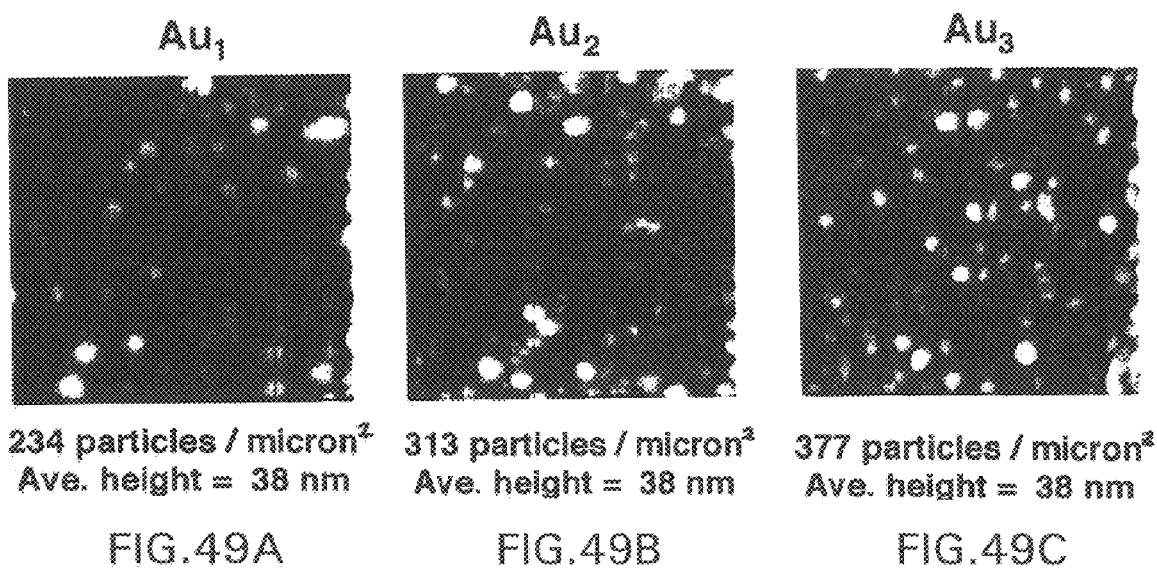
FIG.49A — 234 particles / micron² Ave. height = 38 nm
FIG.49B — 313 particles / micron² Ave. height = 38 nm
FIG.49C — 377 particles / micron² Ave. height = 38 nm

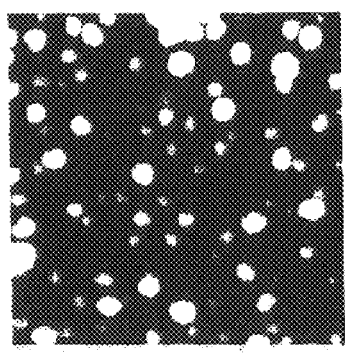 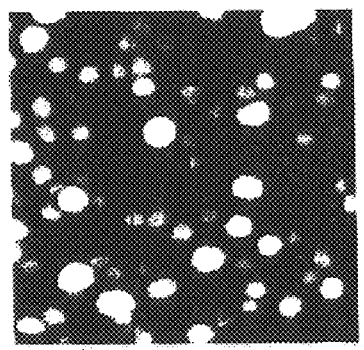 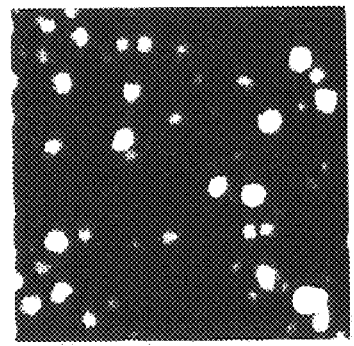
145 Particles / micron$^2$
Ave. Height = 51 nm
FIG. 51A
147 Particles / micron$^2$
Ave. Height = 53 nm
FIG. 51B
156 Particles / micron$^2$
Ave. Height = 55 nm
FIG. 51C

SELF-ASSEMBLED METAL COLLOID MONOLAYERS HAVING SIZE AND DENSITY GRADIENTS

This is the National Stage of International Application No. PCT/US97/15581, filed Sep. 4, 1997; which is a continuation-in-part of application Ser. No. 08/769,970, filed Dec. 19, 1996, now abandoned and which claims the benefit of U.S. Provisional Application No. 60/025,064, filed Sep. 4, 1996.

BACKGROUND OF THE INVENTION

The present invention relates to self-assembled metal colloid monolayers, methods of preparation, and use thereof.

In surface enhanced Raman scattering (SERS), million-fold enhancements in Raman scattering can be obtained for molecules adsorbed at suitably rough surfaces of Au, Ag, and Cu. Although many approaches have been reported, preparation of well-defined, stable SERS substrates having uniform roughness on the critical 3 to 100 nm scale has proven difficult. Because colloidal Au can be synthesized as monodisperse solutions throughout most of this size regime, and because molecules adsorbed to closely spaced colloidal Au and Ag exhibit enhanced Raman scattering, these particles are excellent building blocks for SERS-active substrates. The key issue is whether colloidal Au and Ag particles can be organized into macroscopic surfaces that have a well-defined and uniform nanometer-scale architecture. Indeed, controlling nanostructure is currently a central focus throughout materials research. Progress in self assembly of organic thin films on metal surfaces [C. D. Bain and G. M. Whitesides, *Angew. Chem. Int. Ed Engl.* 28, 506 (1989); A. Ulman, *An Introduction to Ultrathin Organic Films, from Langmuir-Blodgett to Self-Assembly* (Academic Press, Boston, 1991)] led us to explore the reverse process: self assembly of colloidal Au and Ag particles onto supported organic films. As detailed below, this approach has yielded surfaces that are SERS-active, characterizable at both the macroscopic and microscopic levels, highly reproducible, electrochemically addressable, and simple to prepare in large numbers. Moreover, these substrates have a surface roughness that is defined by the colloid diameter (which is tunable) and an average interparticle spacing that is continuously variable. As such, self-assembled Au, Ag and Ag-coated colloid monolayers are likely to have extraordinary utility for SERS.

In the nearly twenty years since the discovery of surface enhanced Raman scattering (SERS) of molecules adsorbed at roughened Ag electrodes, and the accompanying theoretical work demonstrating the need for surface roughness, there have been numerous reports of new architectures for SERS substrates. See, for instance, Liao, P. F.; Bergman, J. G.; Chemla, D. S.; Wokaun, A.; Melngailis, J.; Hawyrluk, A. M.; Economou, N. P. *Chem. Phys. Lett.* 1981, 82, 355–9; Creighton, J. A.; Blatchford, C. G.; Albrecht, M. G. *J. Chem. Soc., Faraday Trans.* 2 1979, 75, 790–8; Blatchford, C. G.; Campbell, J. R.; Creighton, J. A. *Surf. Sci.* 1982, 120, 435–55; Tran, C. D. *Anal. Chem.* 1984, 56, 824–6; Soper, S. A.; Ratzhlaff, K. L.; Kuwana, T. *Anal. Chem.* 1990, 62, 143844; Sequaris, J.-M.; Koglin, E. *Fresenius J Anal. Chem.* 1985, 321, 758–9; Aroca, R.; Jennings, C.; Kovacs, G. J.; Loutfy, R. O.; Vincett, P. S. *J. Phys. Chem.* 1985, 89, 4051–4; Moody, R. L.; Vo-Dinh, T.; Fletcher, W. H. *Appl. Spectrosc.* 1987, 41, 966–70; Ni, F.; Cotton, T. M. *Anal. Chem.* 1986, 58, 3159–63; Yogev, D.; Efrima, S. *J. Phys. Chem.* 1988, 92, 5761–5; Goudonnet, J. P.; Bijeon, J. L.; Warmack, R. J.; Ferrell, T. L. *Phys. Rev. B: Condensed Matter* 1991, 43, 4605–12; Murray, C. A.; Allara, D. L. *J. Chem. Phys.* 1982, 76, 1290–1303; Brandt, E. S. *Appl. Spectrosc.* 1993, 47, 85–93; Alsmeyer, Y. W.; McCreery, R. L. *Anal. Chem.* 1991, 63, 1289–95; Mullen, K.; Carron, K. *Anal. Chem.* 1994, 66, 478–83; Beer, K. D.; Tanner, W.; Garrell, R. L. *J. Electroanal Chem.* 1989, 258, 313–25; Dawson, P.; Alexander, K. B.; Thompson, J. R.; Haas III, J. W.; Ferrell, T. L. *Phys. Rev. B: Condens. Matter* 1991, 44, 6372–81; Roark, S. E.; Rowlen, K. L. *Appl. Spectrosc.* 1992, 46, 1759–61; Roark, Shane E.; Rowlen, K. L. *Chem. Phys. Lett.* 1993, 212, 50; Roark, Shane E.; Rowlen, K. L. *Anal. Chem.* 1994, 66, 261–70; Walls, D.; Bohn, P. *J. Phys. Chem.* 1989, 93, 2976–82; Dutta, P. K.; Robins, D. *Langmuir* 1991, 7, 2004–6; Sheng, R.-S.; Zhu, L.; Morris, M. D. *Anal. Chem.* 1986, 58,1116–9.

These surfaces span a wide range of assembly principles and encompass similarly broad levels of complexity. Examples of SERS-active surfaces include electrochemically-roughened electrodes, microlithographically-prepared elliptical Ag posts, aggregates of colloidal Au or Ag particles—both in solution and associated with chromatographic media, evaporated thin films, Ag-coated latex particles, substrates prepared by chemical reduction of $Ag^+$, and liquid Ag films. The motivation for this work stems from several intrinsically attractive aspects of SERS as a vibrational spectroscopy-based structural tool and/or analytical method: million fold signal enhancements compared to solution Raman spectra, adsorption-induced fluorescence quenching, a lack of interference from $H_2O$, and molecular generality. However, while SERS has been invaluable for certain narrowly defined applications, most spectroscopists would agree that the technique has not lived up to its enormous potential.

The problem has been the inability of any previous surface to meet all, or even most, of the essential criteria that would define a truly useful SERS substrate: strongly enhancing, reproducible, uniformly rough, easy to fabricate, and stable over time. Biocompatibility is also extremely important, insofar as previous studies demonstrating partial or full protein denaturation upon adsorption to SERS-active substrates [Holt, R. E.; Cotton, T. M. *J: Am. Chem. Soc.* 1989, 111, 2815–21; Lee, N.-S.; Hsieh, Y.-Z.; Morris, M. D.; Schopfer, L. M. *J. Am. Chem. Soc.* 1987, 109, 1353–63] have proven to be a major setback to the use of SERS in biological systems. Other desirable characteristics include electromagnetic tunability (i.e. the ability to control the wavelength where optimal enhancement occurs, so as to match the substrate to the photon source), electrochemical addressability—to control the extent of adsorption and the redox state of adsorbed species, a lack of surface "activation" steps, and a low cost per substrate. This last feature is particularly important for applications involving large numbers of routine measurements, such as in environmental monitoring, airport security, and clinical medicine.

SUMMARY OF THE INVENTION

Detailed embodiments of the present invention are disclosed herein. However, it is understood that certain preferred embodiments are merely illustrative of the invention which may be embodied in various forms and applications. Specific compositional and functional details disclosed herein are not meant to be interpreted as limiting, but merely as support for the invention as claimed and as appropriate representations for teaching those skilled in the art to variously employ the present invention in any appropriate embodiment.

We report here a new approach to SERS substrates that meets all of the criteria delineated above. Our strategy involves assembly of colloidal Au, Ag, or other suitable metal particles into macroscopic two-dimensional arrays on polymer-immobilized substrates (FIG. 1). In the first, covalent approach, reactive hydroxyl/oxide groups are generated on a substrate. For many substrates (glass, metal, etc.), such functional groups are already present in high concentration. A second step involves surface-initiated polymerization of bifunctional organosilanes such as $(RO)_3Si(CH_2)_3A$. The alkoxysilane forms covalent attachments to the surface via hydrolysis. The pendant functional group A (FIG. 1B), chosen for its high affinity toward noble metal surfaces, extends out into solution. In the final step, the polymer-derivatized substrate is immersed into a solution of colloidal Au particles, where surface assembly spontaneously occurs. An alternate approach based on high affinity binding of streptavidin to biotin can also be used (FIG. 1C). See Wilchek, M.; Bayer, E. A. *Anal. Biochem.* 1988, 171, 1 and Anzai, J.; Hoshi, T.; Osa, T *Trends Anal. Chem.* 1994, 13, 205–10. Here, a biotinylated surface is reacted with a colloidal Au-streptavidin conjugate to form a colloid-based surface held together by non-covalent interactions.

With molecular self-assembly on metal substrates [Nuzzo, R. G.; Allara, D. L. *J. Am. Chem. Soc.* 1983, 105, 4481–4483; Bain, C. D.; Whitesides, G. M. *Angew. Chem. Int. Ed. Engl.* 1989, 28, 506–512] now established as an important route to controlling interfacial properties, it should be pointed out that the approaches delineated in FIG. 1 define what is essentially the inverse process: self-assembly of well-defined particulate metal films on organic substrates. The term self-assembly refers to our finding that interparticle spacing is governed by interparticle repulsive forces. We have explored this chemistry in detail by varying substrate, polymer, colloid diameter, and reaction conditions. Moreover, the electrochemical characteristics of colloid-based surfaces, the kinetics of surface formation, and the electromagnetic properties of composite particles have been investigated. We also describe here the basic steps involved in surface assembly and characterization, as well as experimental verification of SERS activity. What distinguishes this work are the following features: macroscopic surfaces of controlled and uniform roughness can be prepared by self-assembly, the resulting substrates are compatible with biomolecules, and the surfaces exhibit a high degree of durability/stability over time.

Our construction protocol for SERS-active Au and Ag colloid monolayers exploits the simplicity of self assembly from solution and the affinity of noble metal surfaces for certain organic functional groups (FIG. 1). In our case, these moieties are present by virtue of organic films either polymerized or deposited on the surface of macroscopic (0.8 cm×2 cm) substrates. Immersion of the functionalized substrate into a dilute solution of monodisperse colloidal Au or Ag particles leads to colloid immobilization. This solution-based process is extremely general, encompassing numerous permutations of insulating and conducting substrates [glass, quartz, plasma-treated Teflon, Formvar, indium-doped $SnO_2$ (ITO), and Pt], organic films [hydrolyzed mono-, di- and trialkoxysilanes containing the functional groups CN, $NH_2$, 2-pyridyl, $P(C_6H_5)_2$, and SH, as well as carboxyl-terminated $C_{18}$ organothiol self-assembled monolayers], and colloids [5 to 70 nm in diameter for Au, and 5 to 20 nm in diameter for Ag and Au/Ag composites]. Our work has focused on Au and Ag particles, but with the right functional group A, a wide variety of colloidal particles could constitute building blocks for well-defined macroscopic surfaces.

Solution-based surface assembly also eliminates preparative, geometric, and operational constraints associated with most previously described SERS substrates. Thus, one liter of 17 nM, 12-nm diameter colloidal Au, which can be stored indefinitely at room temperature, can be used to prepare 2,000 0.5-cm$^2$ surfaces with only a 1% decrease in colloid concentration. Importantly, these substrates can be assembled sequentially or simultaneously. Surfaces in novel geometries that extend the utility of SERS can now be derivatized, including one face of a 5 ml-volume spectroelectrochemical cell, large glass sheets several centimeters on a side, and the inside of a 20-mm inner diameter glass capillary. Moreover, once constructed, no further activation steps (such as electrochemical oxidation-reduction cycles or particle aggregation) are required to initiate SERS activity. It should be noted that the particles are tightly bound and the thermodynamic stability of these surfaces is very high: exchange with molecules in solution containing the functional group A does not occur.

This preparation method differs greatly from electrochemical roughening of electrodes and metal vapor deposition, the most common routes to solid SERS substrates. Each of these protocols yields surfaces with polydisperse roughness on the nanometer scale. This problem is circumvented by the methods of FIG. 1. Since the size of the colloid precursor can be easily varied and controlled, the defining roughness of the surface is pre-determined. Not only can the roughness be tuned according to experimental needs, but the roughness is uniform—all particles are of the same size and dimensions. This is of particular importance in SERS where enhancement at the surface is directly correlated to nanometer scale roughness.

Two-dimensional colloid self assembly also differs from the numerous methods for preparation of SERS-active substrates involving colloidal particles [Creighton, J. A.; Blatchford, C. G.; Albrecht, M. G. *J. Chem. Soc., Faraday Trans. 2* 1979, 75, 790–8; Blatchford, C. G.; Campbell, J. R.; Creighton, J. A. *Surf Sci.* 1982, 120, 435–55; Tran, C. D. *Anal. Chem.* 1984, 56, 824–6; Soper, S. A.; Ratzhlaff, K. L.; Kuwana, T. *Anal. Chem.* 1990, 62, 1438–44; Sequaris, J.-M.; Koglin, E. *Fresenius J. Anal. Chem.* 1985, 321, 758–9; Ahern, A. M.; Garrell, R. L. *Langmuir* 1991, 7, 254–61; Angel, S. M.; Katz, L. F.; Archibald, D. D.; Honigs, D. E. *Appl. Spectrosc.* 1989, 43, 367–72; Clarkson, J.; Campbell, C.; Rospendowski, B. N.; Smith, W. E. *J. Raman Spectrosc.* 1991, 22, 771–775]. In those methods, there is a single size of particle, but since there is no control over interparticle interactions, aggregates of ill-defined dimensions are often formed. In this work, strong covalent or non-covalent bonds to the substrate reduce the surface mobility of the nanoparticles and prevent the spontaneous coalescence of particles on the surface. Thus, the initial size uniformity is maintained.

For several reasons, keeping the particles physically separated is a critical component to our assembly strategy. (1) The intrinsic biocompatibility of individual colloidal Au particles is maximized: aggregates begin to approximate larger surfaces where, for Au, protein denaturation is a serious concern. (2) The resulting surfaces are more straightforwardly characterized than particle aggregates. (3) It is known both from theory and experiment that closely-spaced but physically separated particle arrays can be strongly enhancing [Inoue, M.; Ohtaka, K. *J. Phys. Soc. Jpn.* 1983, 52, 3853–64; Chu, L.-C.; Wang, S.-Y. *J. Appl. Phys.* 1985, 57, 453–9; Chu, L.-C.; Wang, S.-Y. *Phys. Rev. B: Condens. Matter* 1985, 31, 693–9]. As the interparticle spacing increases toward $\lambda$, nearly all of the SERS effect is lost:

completely isolated small colloidal Au particles are weakly enhancing. In our view, the relatively small loss in enhancement for non-contacting, closely-spaced particles is more than offset by an increased ease of characterization, improved biocompatibility, and demonstrated improvements in stability (vide infra). FIG. 1D depicts various regimes for colloid immobilization that could result from using the strategy delineated above. In surface A, the particles are isolated, but too far apart to be strongly enhancing. In B, the particles are close enough to see the SERS effect, but still isolated (thus retaining the biocompatibility properties of individual particles). Surface C represents a close-packed colloid monolayer, while D represents particle multilayers approximating a bulk surface. The latter surface can be prepared from a monolayer. Our goals are to prepare and characterize surfaces like B, C and D, and to use them to solve a variety of problems in analytical, biological, environmental, clinical and inorganic chemistry.

To this end, the ease of fabrication and handling of Au colloid monolayers is very significant. Large numbers of samples can be prepared simultaneously, with no restrictions on the size or shape of the substrates, and without the need for even moderately sophisticated equipment (i.e. no potentiostat, no vacuum deposition apparatus). Furthermore, with transparent substrates, the optical properties of the SERS-active surface can be monitored directly. This means that a reasonably accurate prediction of enhancement factors can be made a priori. Indeed, as described below, uv-vis is our basic characterization tool.

BRIEF DESCRIPTION OF THE FIGURES

FIGS. 30a–c show a tapping-mode AFM images of Au colloid multilayer film preparation on APTMS-derivatized glass using 12 nm Au particles, wherein;

FIG. 30a shows an image of a submonolayer;

FIG. 30b shows an image of a submonolayer after 2 exposures to 2-mercaptoethanol/Au colloid; and FIG. 30c shows an image of the submonolayer(bottom left) after 5 exposures to 2-mercaptoethanol/Au colloid, images of FIGS. 30a–c each being 1 mm×1 mm with 0–100 nm z-scale.

FIG. 43 shows wavelength-dependent SERS maps from a single sample of a Au/Ag continuous gradient colloidal Au on 3-mercaptopropylmethyl-dimethoxysilane (MPMDMS)/glass. Intensities have been normalized to 30 mW of 514 nm excitation. Each square represents 1 spectrum in a 2 mm×2 mm area, with the peak intensities calculated from the 1610 cm$^{-1}$ band of trans-4,4'-bis-pyridylethylene (BPE). Experimental conditions: 30 minutes Au exposure, 40-minute Ag exposure. [BPE]=10 mM; two collections of a 2-s integration, 5 cm$^{-1}$ band pass.

FIGS. 44A, 44B and 44C shows wavelength dependent SERS maps from three samples of continuous combinatorial gradients based on 14- and 28-nm diameter colloidal Au (Au colloid/MPMDMS/glass). Exposure times on the right-hand image (Au exposure=180 minutes, 5× diluted colloid, Ag exposure=40 minutes) were based on the experimental findings for the left-hand image (30 minutes Au exposure, 40-minute Ag exposure). Experimental conditions are the same as in FIG. 43.

FIGS. 49A, 49B and 49C show AFM images (1 μm×1 μm, with 80 nm Z-scale) for the samples with varying Au coverages described in FIGS. 46A and 46B, and FIGS. 47A and 47B.

FIGS. 51A, 51B and 51C show AFM images (1 μm×1 μm, with 80 nm Z-scale) for the samples described in FIGS. 50A and 50B.

DETAILED DESCRIPTION OF THE INVENTION

Below we describe data regarding the preparation, characterization, and applications of self-metal colloid monolayers. Experimental examples are included.

Two lines of evidence demonstrate that immobilized particles are located solely at the surface of, and not embedded within, the organic film. (i) Colloidal particles are very tightly attached to the polymer (when stored in water, no particle dissociation occurs after 1 year), yet monolayer formation does not occur on polymers with pendant methyl or methoxy groups. These data indicate that multiple specific covalent interactions between polymer functional groups (which are oriented toward the solution) and the particle surface are necessary for immobilization. (ii) Although SERS spectra for adsorbates from solution are easily obtained (see below), the SERS spectra of organosilane polymer films underneath Au monolayers are quite weak. This contrasts with published SERS studies of colloid/polymer mixtures [P. Matejka, B. Vlcková, J. Vohlidal, P. Pancoska, V. Baumruk, *J. Phys. Chem.* 96, 1361 (1992); P. C. Lee and D. Meisel, *Chem. Phys. Lett.* 99, 262 (1983)], and demonstrates that the surface of immobilized metal particles is accessible to solvent. In accord with this finding is our observation that the optical spectrum of Au colloid monolayers on transparent substrates depends on the dielectric constant of the surrounding medium.

The optical properties of colloidal Au and the nature of self assembly offer an unprecedented opportunity to monitor surface evolution in real time. The time course of Au colloid monolayer formation on a glass slide coated with polymerized 3-aminopropyltrimethoxysilane (APTMS) is shown in FIG. 2. Binding of 12-nm diameter Au particles to amine groups on the surface is indicated by an absorbance feature at 520 nm, the location of the Mie resonance for isolated small Au particles. As the particle coverage increases, interparticle spacing becomes small compared to the incident wavelength, and a new feature corresponding to a collective particle surface plasmon oscillation grows in at ~650 nm. This feature is responsible for the pronounced SERS activity of collections of colloidal Au particles. Accordingly, when a colloid monolayer in various stages of formation is placed in a solution containing the adsorbate trans-1,2-bis(4-pyridyl) ethylene (BPE), the SERS intensity for the ring stretch at 1610 cm$^{-1}$ closely tracks the magnitude of the absorbance at 650 nm. Immersion time is one of four routes we have found to alter the rate or extent of surface formation, the others being choice of organosilane functional group (rate of surface formation for SH>NH$_2$>>CN), colloid concentration, and the presence or absence of an adsorbate on the colloidal particle.

Figure 1A:
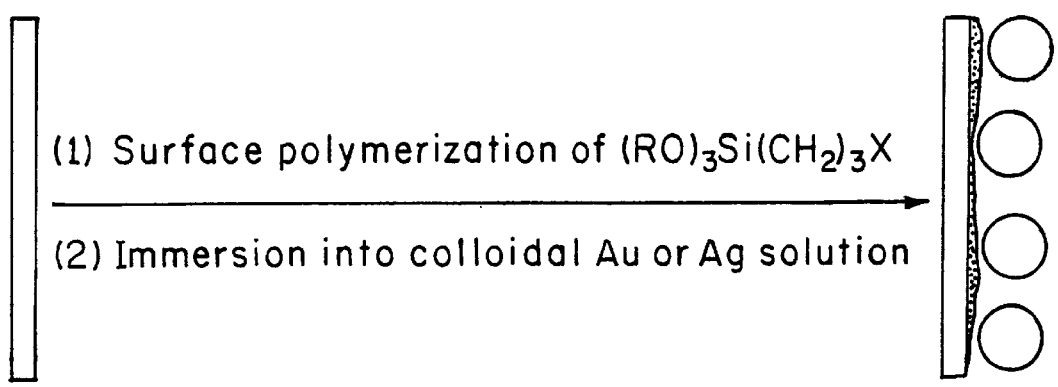
FIGS. 1A–1B show assembly strategies for Au and Ag colloid monolayers; X=A=CN, $NH_2$, 2-pyridyl, $P(C_6H_5)_2$, and SH.
Figure 1B:
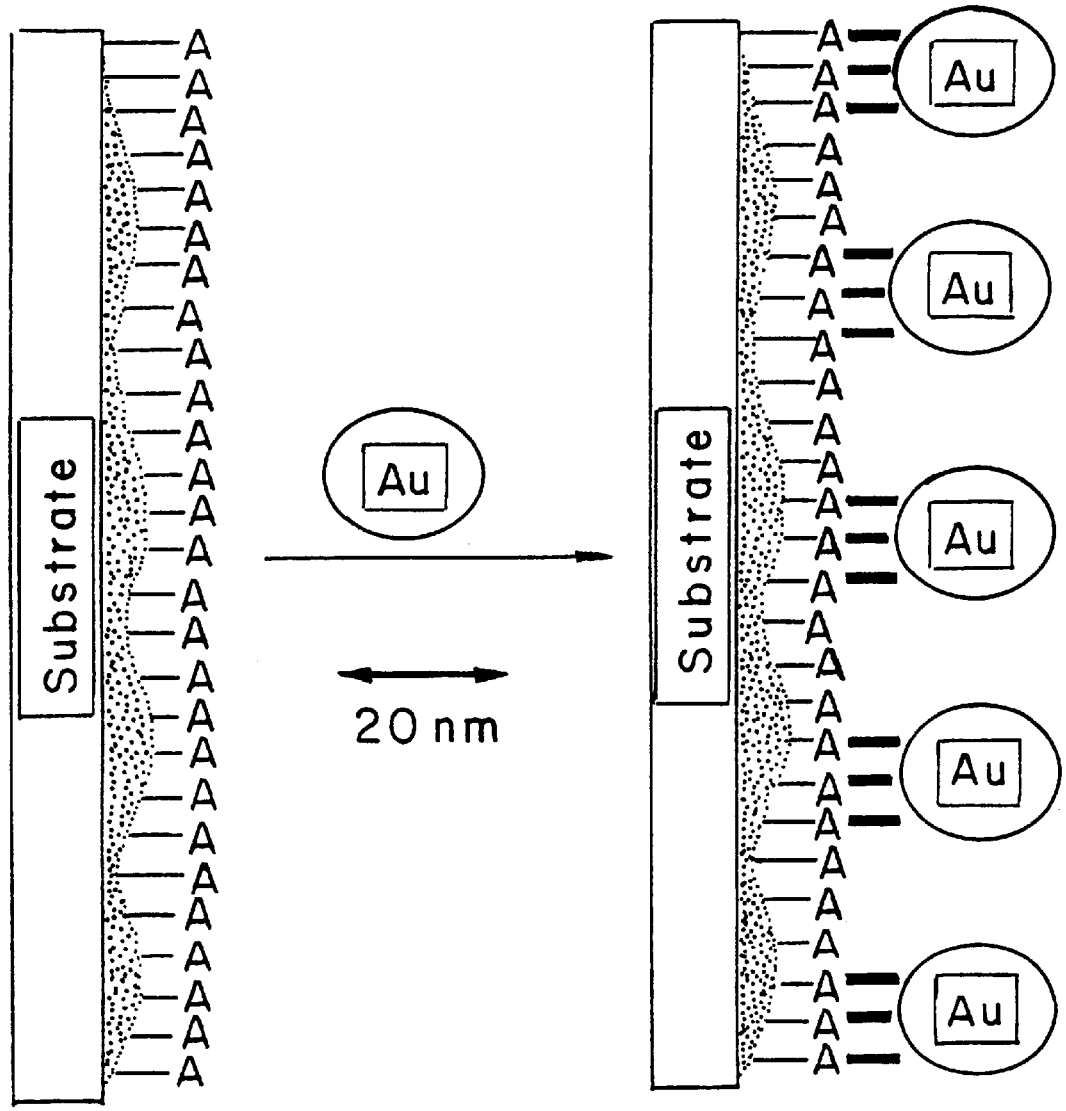
Figure 1C:
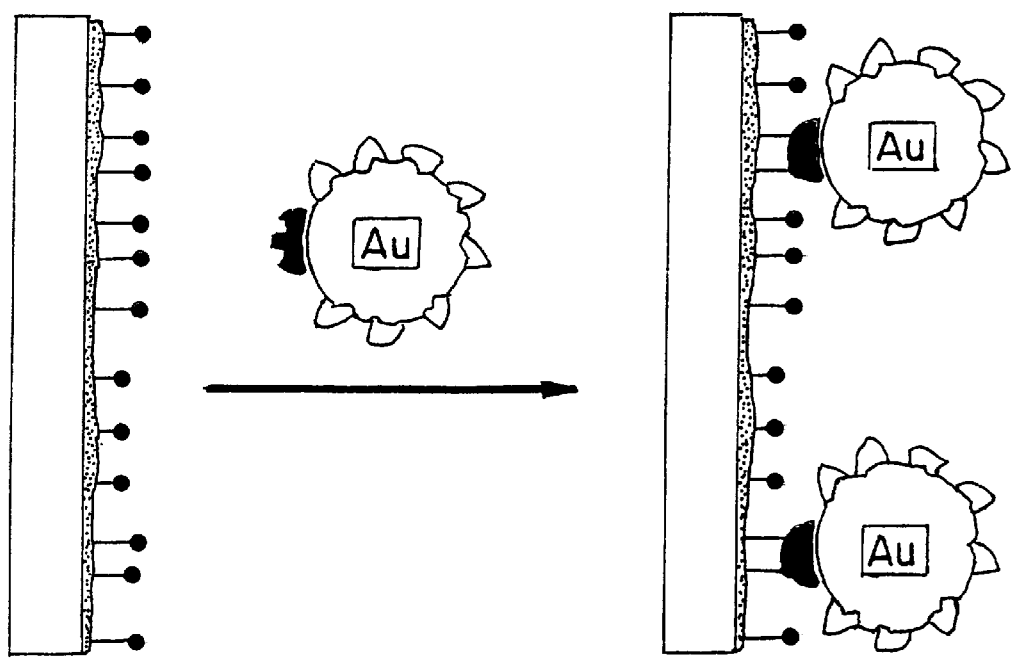
FIG. 1C demonstrates one embodiment of the present invention based on high affinity binding of streptavidin to a biotin.
Figure 1D:
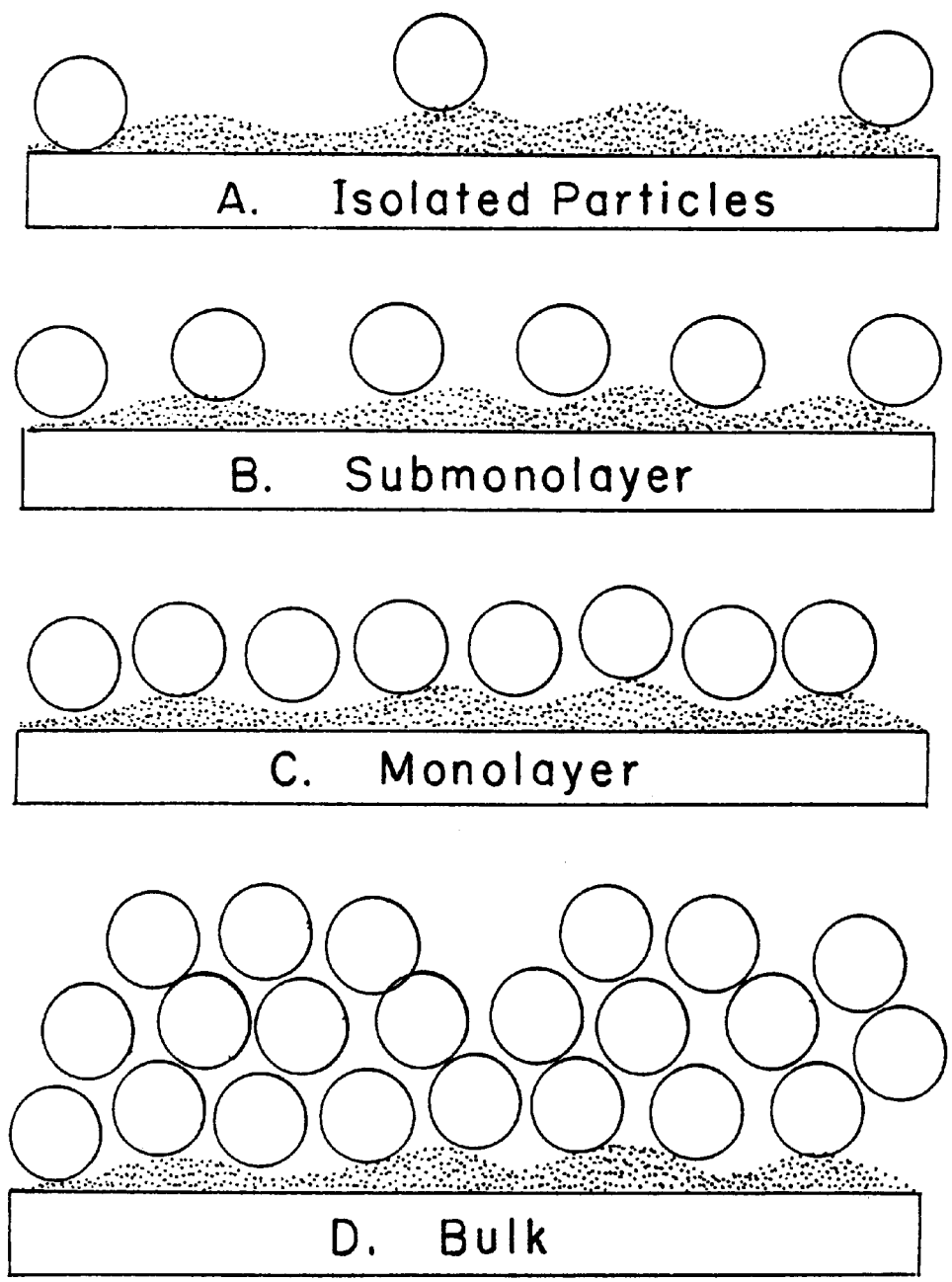
FIG. 1D depicts various degrees of substrate surface coverage by metal particles.
Figure 2A:
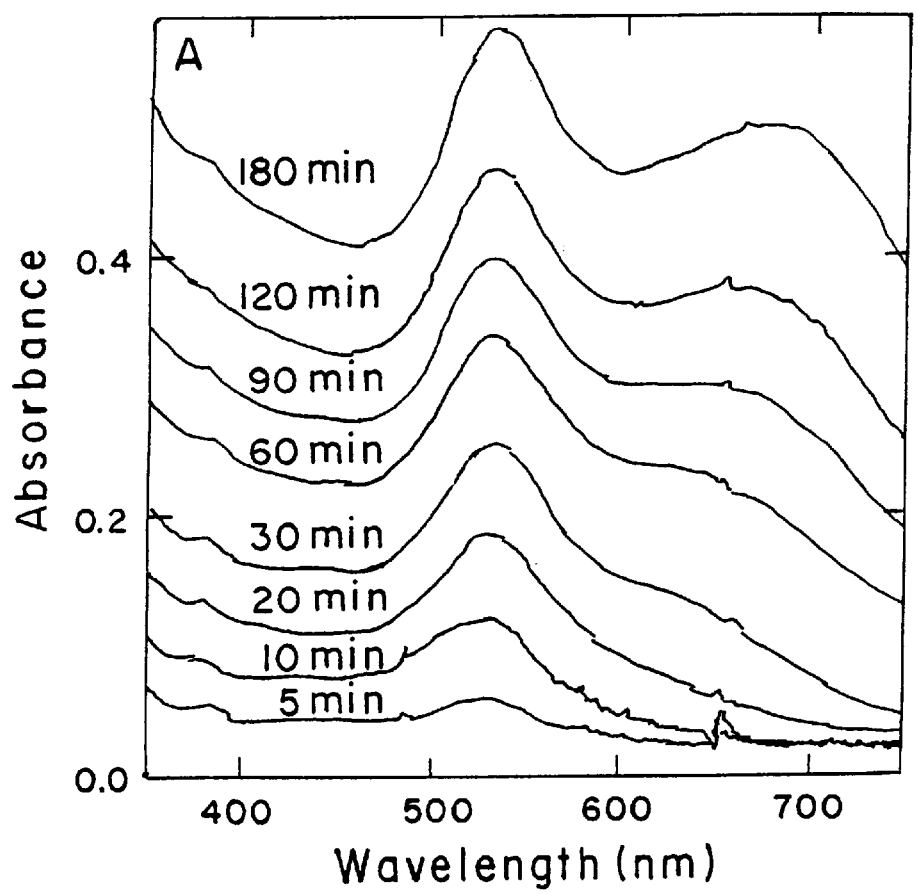
FIG. 2A illustrates the ultraviolet-visible kinetics of a Au colloid monolayer on a glass substrate coated with 3-aminopropyltrimethoxysilane.
Figure 2B:
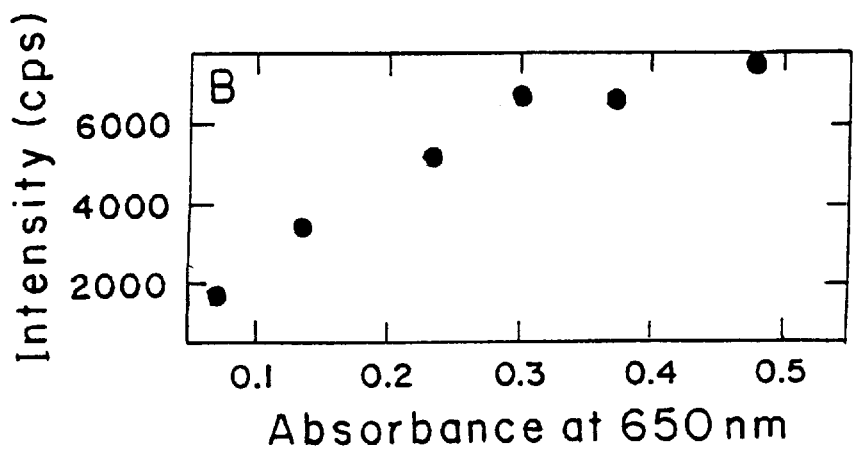
FIG. 2B illustrates the SERS kinetics of a Au colloid monolayer on a glass substrate coated with 3-aminopropyltrimethoxysilane.

FIG. 2A shows kinetics of Au colloid monolayer formation by ultraviolet-visible (uv-vis). A series of uv-vis spectra of Au colloid-functionalized glass slides in H$_2$O obtained with an HP-8452A spectrophotometer. Cleaned (4:1 H$_2$SO$_4$:H$_2$O$_2$, 70° C.) rectangular glass slides (0.9 mm×25 mm) were placed into a dilute solution of 3-aminopropyltrimethoxysilane (APTMS) (0.3 ml: 3 ml of CH$_3$OH) for 12 hours and rinsed with CH$_3$OH upon removal. The polymer-coated slides were then immersed in a 17 nM solution of 12-nm diameter colloidal Au particles (wavelength maximum=520 nm) [Garrell, R. L. *Anal. Chem.* 1989, 61, 401A–11A; Tran, C. D. *Anal. Chem.* 1984, 56, 824–67,20]. At each time indicated (and at several others not shown), the slide was removed from the Au colloid solution, and an optical spectrum was recorded in H$_2$O, followed by a SERS spectrum in 4 mM BPE in 95:5 H$_2$O:CH$_3$OH (20 mW 632.8 nm, Spex 1403 double monochromator, Hamamatsu R928 photomultiplier tube, bandpass=7 cm$^{-1}$, scan rate=1 cm$^{-1}$s$^{-1}$, integration time=1 s). FIG. 2B shows kinetics of Au colloid monolayer formation by SERS. SERS intensity for the 1610 cm$^{-1}$ band versus absorbance at 650 nm. Other bands in the BPE SERS spectrum evolve with identical kinetics.

This high degree of control over surface formation has important ramifications for reproducibility, a long-standing complication in SERS research. For example, when BPE was adsorbed to eight identical Ag colloid monolayers on glass, the greatest variation in integrated peak intensity for the 1610 cm$^{-1}$ band was less than 8%. Similarly, for five different locations on a single substrate, the greatest difference was only 5%. As these values incorporate intrinsic errors associated with variation in laser power and sample positioning, the actual sample reproducibility is significantly better. This reproducibility extends to the nanometer scale, where Au and Ag colloid monolayers have been imaged using transmission electron microscopy (TEM), field emission scanning electron microscopy (FE-SEM), and atomic force microscopy (AFM). A representative TEM image of an Au colloid monolayer prepared on an SiO$_x$-coated Formvar surface is shown in FIG. 3. The Au particles are confined to a single layer, and the vast majority of particles are isolated from each other, unlike previous TEM studies of SERS-active Au and Ag colloids. Furthermore, the large field of view available with TEM allows us to conclude that particle aggregation has been eliminated over the entire sample. Similar conclusions obtain from large-field FE-SEM images and from multisite tapping-mode AFM images of Au-modified glass surfaces. The AFM image from a glass slide coated with 3-aminopropylmethyldimethoxysilane indicates a roughness of 1 to 3 nm, notwithstanding a few isolated locations where the polymer roughness approaches 8 to 10 nm. This roughness scale is typical for organosilane films on glass or quartz. Immobilization of 12-nm colloidal Au particles to a coverage equivalent to that shown for 180 to 210 min in FIG. 2 yields a surface with features 12 to 20 nm high and 20 to 30 nm wide. The increased dispersion in particle size relative to TEM results from convolution of the true particle size with the AFM tip size, but are nevertheless of sufficient quality to conclude that the surface is composed of a monolayer of separated particles, in agreement with FE-SEM images on similar substrates. Importantly, we have demonstrated that the spacing obtained on these colloid-based surfaces is sufficient to yield SERS enhancement. The bottom panel of FIG. 3B shows the SERS spectrum of BPE adsorbed onto the derivatized TEM grid pictured in the top panel. For comparison, the Raman scattering spectrum of an equivalent amount of BPE deposited onto an unmodified SiO$_x$-coated TEM grid is also shown. The intensity difference in these two samples clearly demonstrates the enhancing properties of colloid-based surfaces.

Figure 3A:
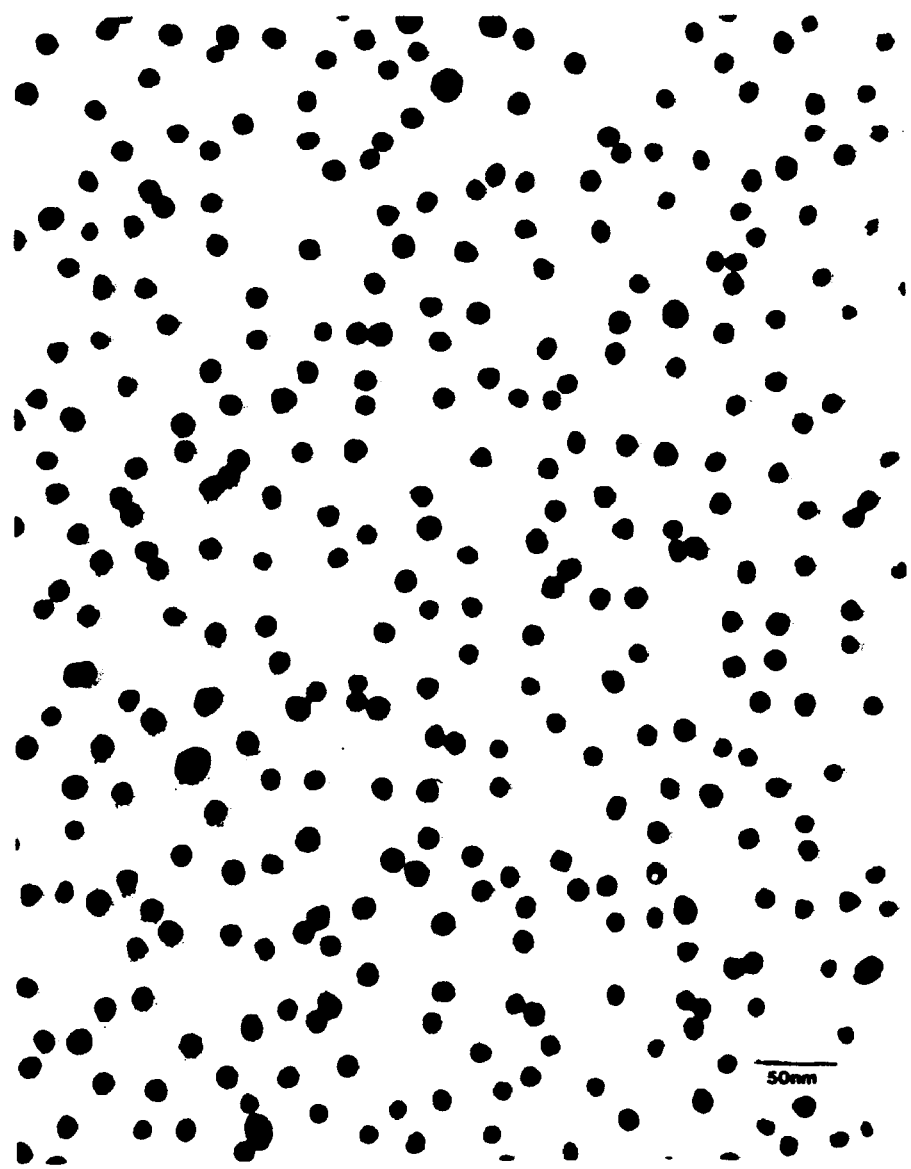
FIG. 3A is a TEM image of a Au colloid monolayer prepared on a $SiO_x$-coated formvar surface.
Figure 3B:
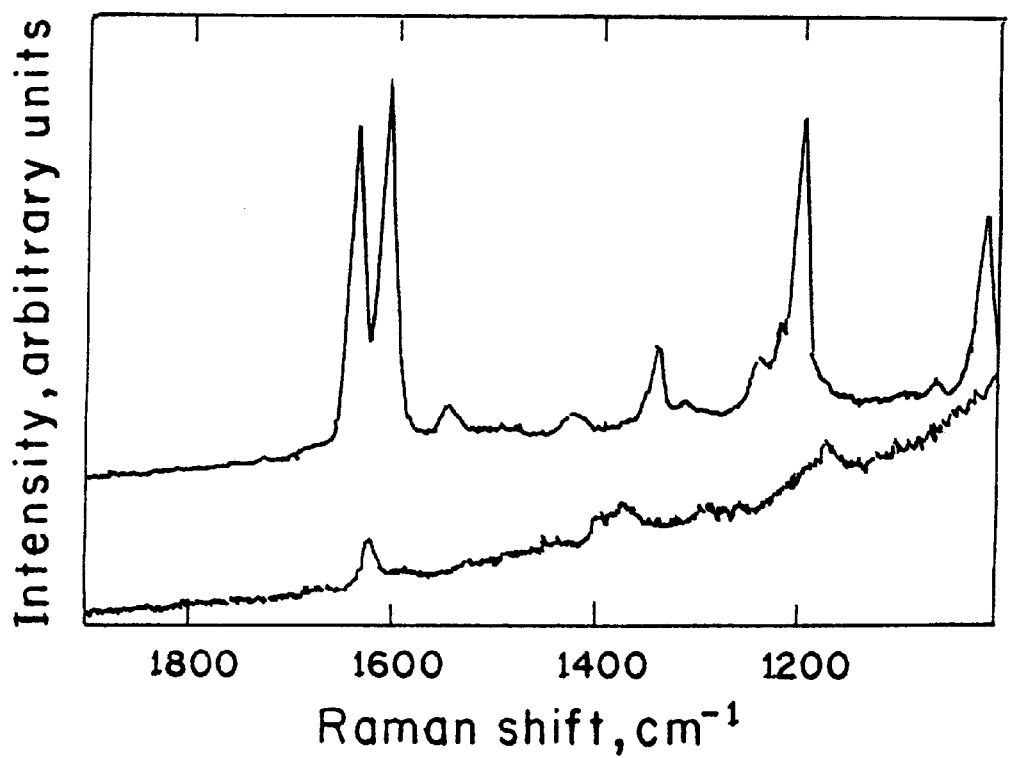
FIG. 3B shows the SERS spectrum of BPE adsorbed onto the derivatized TEM grid used to produce FIG. 3A.

FIG. 3A shows an image from a Formvar-coated Cu TEM grid which had been sputter-coated with a thin layer of SiO$_x$ (Ted Pella, Inc.), treated for 2.5 hours in neat 3-cyanopropyldimethylmethoxysilane, rinsed exhaustively with CH$_3$OH upon removal, and immersed for 12 hours in colloidal Au (12 nm diameter) [Garrell, R. L. *Anal. Chem.* 1989, 61, 401A–11A; Tran, C. D. Anal. Chem. 1984, 56, 824–6]. Imaging was performed on a JEOL 1200 EXII instrument operated at 80 kV accelerating voltage. The area depicted is 0.28 mm$^2$ and is representative of the sample surface. FIG. 3B shows a SERS spectrum (upper) of 5 ml of 1 mM BPE drop-coated onto the surface of the derivatized TEM grid (100 mW, 647.1 nm, 5 cm$^{-1}$ bandpass, 2 cm$^{-1}$ step, 2 s integration). For comparison, an identical quantity of BPE was drop-coated onto an underivatized SiO$_x$ grid; the Raman spectrum from this sample is shown (1 cm$^{-1}$ step, 1 s integration).

Figure 4:
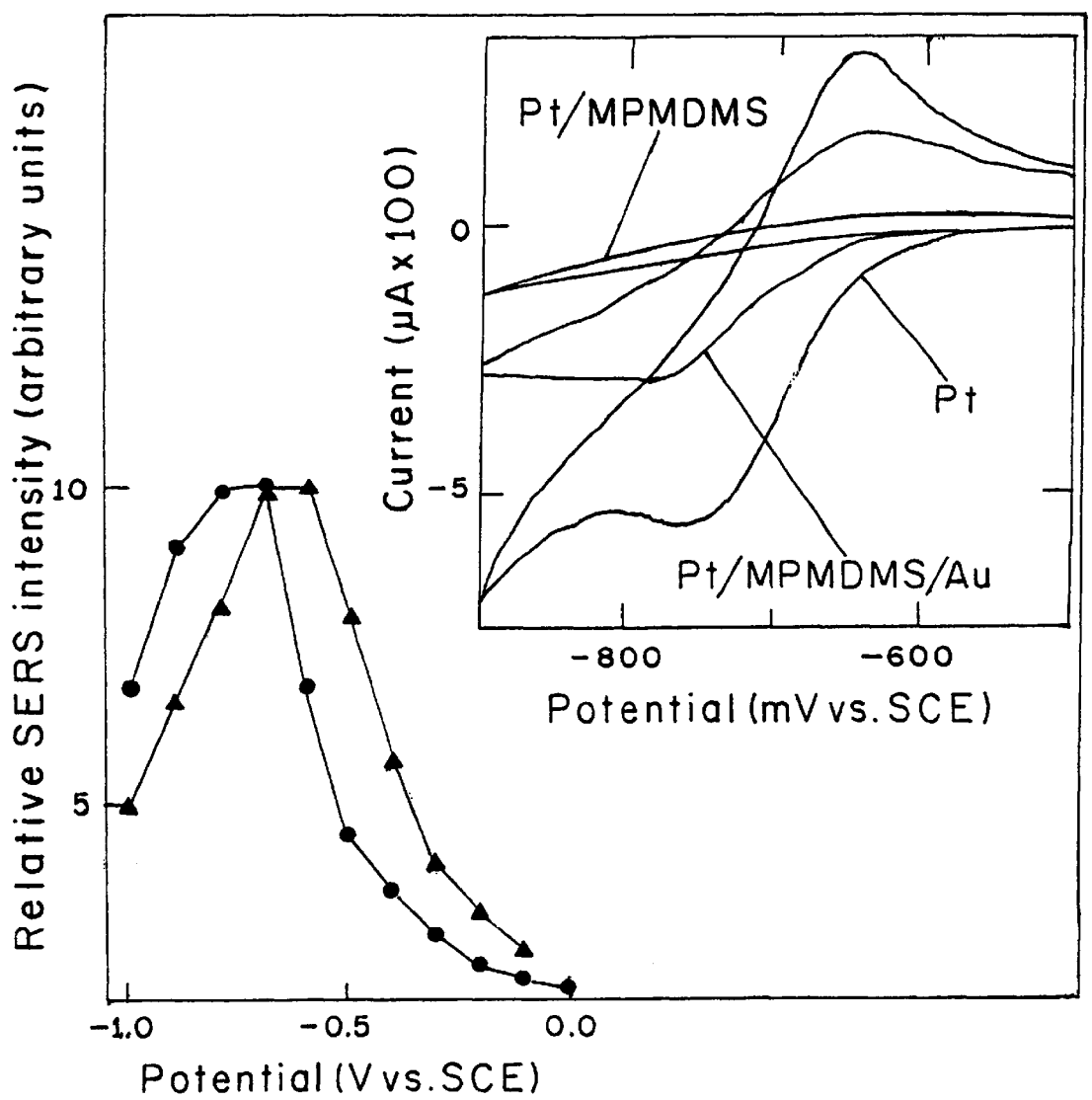
FIG. 4 shows an electrochemical potential dependence of SERS intensity of the 1006 $cm^{-1}$ band of pyridine on a Ag colloid monolayer on Pt and on bulk Ag.

Another important feature of film-supported metal colloid monolayers is that the particles are subject to electrochemical potentials applied to underlying conductive substrates. Consequently, like SERS-active electrodes, Ag colloids immobilized on Pt exhibit an electrochemical potential-dependent SERS intensity for adsorbed pyridine (FIG. 4). Identical maximas for the two surfaces in the intensity versus potential plots suggests that the voltage drop across the polymer film is minimal. Voltammetry at colloid-based surfaces also resembles that at macroscopic electrodes. The first reduction wave for methyl viologen (MV$^{2+}$) is markedly rectified at an organosilane-coated Pt electrode (FIG. 4, inset) but returns upon immobilization of Au particles. The slightly broadened peak-to-peak separation is expected for an array of closely spaced microelectrodes. Considering the demonstrated biocompatibility of 5 to 20 nm diameter Au particles, the ability to make electrochemical measurements at Au colloid monolayers suggests possible electrode-based biosensor applications.

FIG. 4 shows an electrochemical potential dependence of SERS intensity of the 1006 cm$^{-1}$ band of pyridine on an Ag colloid monolayer on Pt and on bulk Ag [Albrecht, M. G.; Creighton, J. A. *J. Am. Chem. Soc.* 1977, 99, 5215–7]. The monolayer was prepared as follows: Clean Pt foil was placed into neat APTMS for 4 hours. After rinsing with triply distilled H$_2$O and air-drying, the polymer-coated foil was dipped in Ag colloid solution [Soper, S. A.; Ratzhlaff, K. L.; Kuwana, T. *Anal. Chem.* 1990, 62, 1438–44] for 1 hour. The derivatized foil was then rinsed with triply distilled H$_2$O and air-dried. In the absence of colloidal Ag, no pyridine SERS spectra were observed at any potential. See FIG. 2 for spectral acquisition parameters. Inset: Voltammograms (100 mV/s, N$_2$ atmosphere) of 5 mM MV$^{2+}$ in 0.1 M Na$_2$SO$_4$ on three surfaces: unmodified Pt, Pt coated with surface-polymerized 3-mercaptopropylmethyl-dimethoxysilane (MPMDMS), and Pt coated with MPMDMS and derivatized with 15-nm diameter Au particles (5 hours in neat silane, rinsed, 4 hours in colloidal Au).

Figure 5:
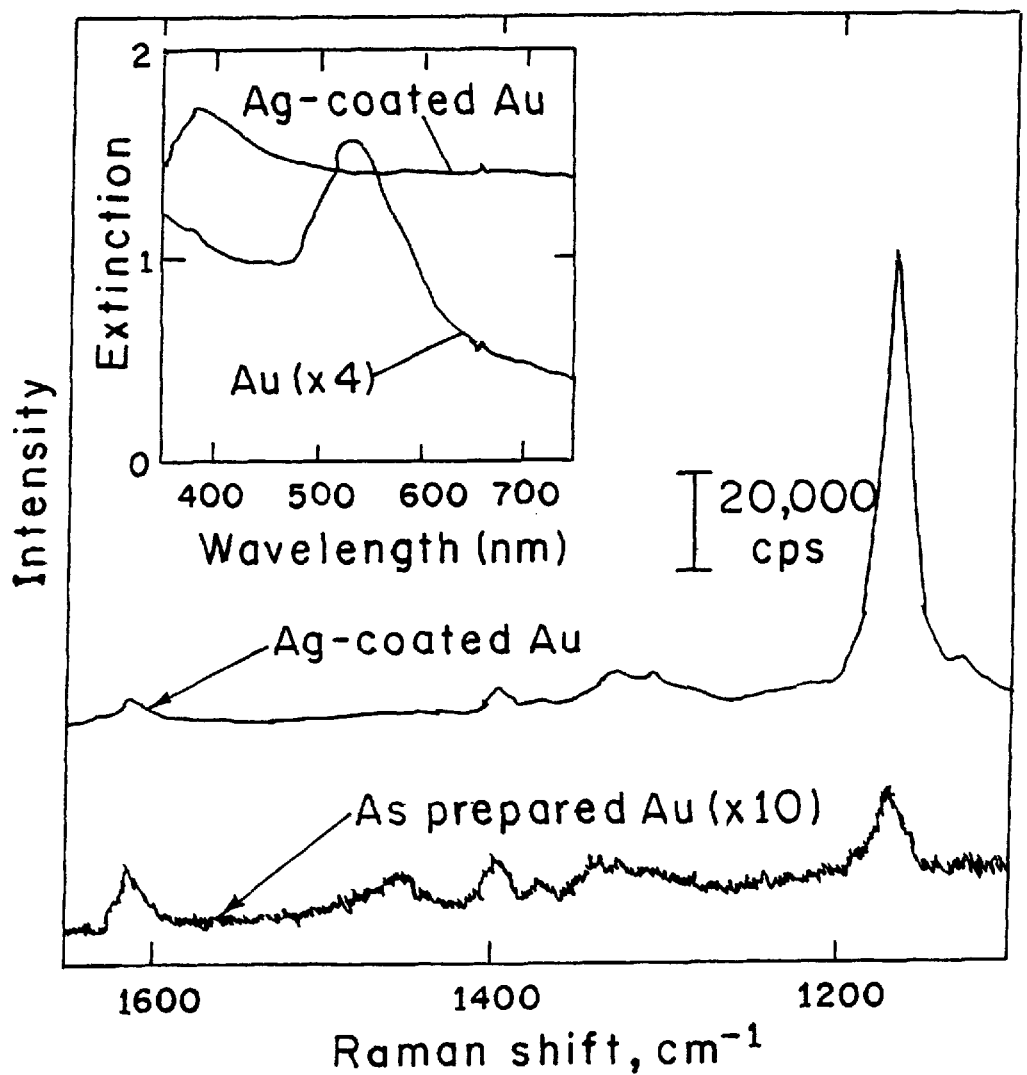
FIG. 5 shows the optical and SERS spectra before and after deposition of Ag onto 18 nm diameter colloidal Au monolayer.

Interparticle spacing in preformed Au monolayers can be further reduced by chemical deposition of an Ag coating; increased interparticle coupling because of decreased spacing and concomitant changes in dielectric properties lead to a dramatic increase in SERS activity. The optical and SERS spectra before and after deposition of Ag onto 18 nm diameter colloidal Au are shown in FIG. 5. Initially, relatively large interparticle spacing is indicated by the absence of a collective particle surface plasmon band in the ultraviolet-visible and by a weakly enhanced SERS spectrum for adsorbed para-nitrosodimethylaniline (p-NDMA). Silver deposition causes a large increase in extinction at all wavelengths as well as a shift in $\lambda_{max}$ from 520 to 386 nm. The shift in energy of and increased extinction at $\lambda_{max}$ concur with expectations based on a computer algorithm for predicting the optical properties of isolated coated particles [C. Bohren and D. R. Huffman, *Absorption and Scattering of Light by Small Particles* (Wiley, New York, 1983)]; best agreement between the experimental and model data is reached with a 4-nm Ag coat (to make 26-nm diameter particles) [The optical constants for Au and Ag were taken from R. H. Morriss and L. F. Collins, *J. Chem. Phys.* 41, 3357 (1961). These values were fit to exponential curves to generate continuous values between 300 and 700 nm]. The exceptional SERS activity (enhancement factor=105) [an enhancement factor (EF) of 5.7×10$^5$ was calculated for the Ag-coated surface by comparing the ratios of background-corrected intensities for a SERS spectrum and a solution spectrum in units of counts s$^{-1}$ watt$^{-1}$ molecule$^{-1}$, and averaging the EF values obtained for six different common peaks—low signal/noise precluded calculation of accurate EFs for the as prepared Au sample] of these substrates reflects optimization of the Ag coating thickness for this particular particle size and spacing of colloidal Au—even greater enhancements may be possible with other combinations.

FIG. 5 shows the effect of Ag coating on the uv-vis and SERS spectra of preformed Au colloid monolayers. The initial substrates were prepared as in FIG. 2, except that the organic film was formed from reaction with 2-(trimethoxysilyl)ethyl-2-pyridine (PETMS) for 24 hours. Silver coating was performed by immersing Au colloid monolayers into a 1:1 mixture of LI Silver enhancer and initiator solutions (Nanoprobes Inc., Stony Brook, N.Y.) for 13 min. The SERS spectra were of 0.5 mM p-NDMA solutions in CH$_3$OH. Optical spectra (inset) were measured in H$_2$O. Instrumental parameters were described in FIG. 2. When Ag is deposited from the plating solution onto a PETMS-derived polymer on glass in the absence of colloidal Au, no SERS intensity could be observed for the same p-NDMA solution, irrespective of coating time.

More detailed characterization of these surfaces follows. The top panel of FIG. 6 shows optical spectra for solutions of isolated and aggregated 13-nm diameter colloidal Au particles in H$_2$O. The unaggregated sol, which has a particle concentration of 17 nM, has a $\lambda_{max}$ of 520 nm. The physical nature of this surface plasmon mode, which gives colloidal Au its characteristic intense burgundy color, is well-understood, as are its dependence on particle size and shape. When the interparticle repulsive forces are sufficiently screened by molecular adsorption, irreversible aggregation occurs and generates a new red-shifted feature in the optical spectrum centered between 600–800 nm. The intensity and $\lambda_{max}$ of this feature scale with the extent of aggregation, with large aggregates exhibiting increased extinction and red-shifted peaks. This "aggregated" band results from coupling of surface plasmons between closely-spaced particles. It has been amply demonstrated, both theoretically and experimentally, that the SERS-activity of aggregated colloidal Au arises from this interparticle coupling. In aggregated sols, the particles are physically connected, but it is important to note that direct contact is not needed to observe collective plasmon modes: as long as the spacing between particles is small compared to the wavelength of light, these collective plasmon modes can be observed. Uv-vis is thus particularly well-suited for analyzing our samples, since the optical spectra of Au colloid monolayers on transparent substrates is easily measured. The same cannot be said of most SERS substrates with a notable exception being those prepared by Roark et al. [Roark, S. E.; Rowlen, K. L. *Appl. Spectrosc.* 1992, 46, 1759–61; Roark, Shane E.; Rowlen, K. L. *Chem. Phys. Lett.* 1993, 212, 50; Roark, Shane E.; Rowlen, K. L. *Anal. Chem.* 1994, 66, 261–70]. Moreover, colloid self-assembly provides a means of tuning surface optical properties through control of interparticle spacings.

The diversity of optical properties attainable through self-assembly of colloidal Au is illustrated in the bottom panel of FIG. 6. Use of two different organosilanes and two sizes of colloidal Au particles yields four distinct surfaces, as evidenced by different optical spectra. In comparison to the data in the top panel, it is clear that interparticle coupling is not as pronounced as for aggregated colloidal solutions. Using 13-nm diameter particles at 0.15 monolayer coverage, there are roughly $1 \times 10^{11}$ particles in a 1 cm$^2$ monolayer which, using a 15-nm slab thickness, are in a volume of $15 \times 10^{-10}$ liters. This translates to a surface concentration of $1 \times 10^{-4}$ M, versus 17 nM in solution. Despite this 4 order-of-magnitude increase in concentration (one that cannot be maintained in solution without aggregation), the particles remain distinct; this lack of surface aggregation is additional strong evidence for specific interactions between the surface of Au and the polymer functional groups and the high stability suggests that multiple linkages must be present. These data are reinforced by the absence of Au or Ag immobilization on polymers derived from trimethoxypropylsilane, which lacks a high-affinity functional group. The key point is that the polymer-particle interaction, an adjustable parameter, controls the particle density, which in turn dictates the optical properties.

Figure 6A:
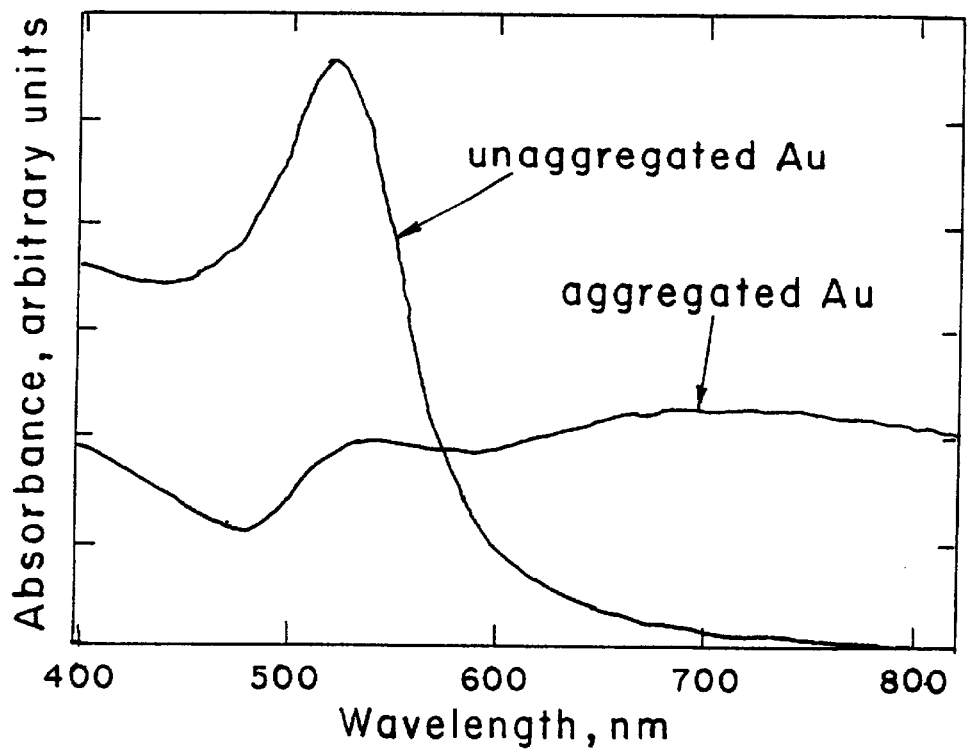
FIG. 6A shows optical spectra for solutions of isolated and aggregated 13 nm colloidal Au particles in $H_2O$.
Figure 6B:
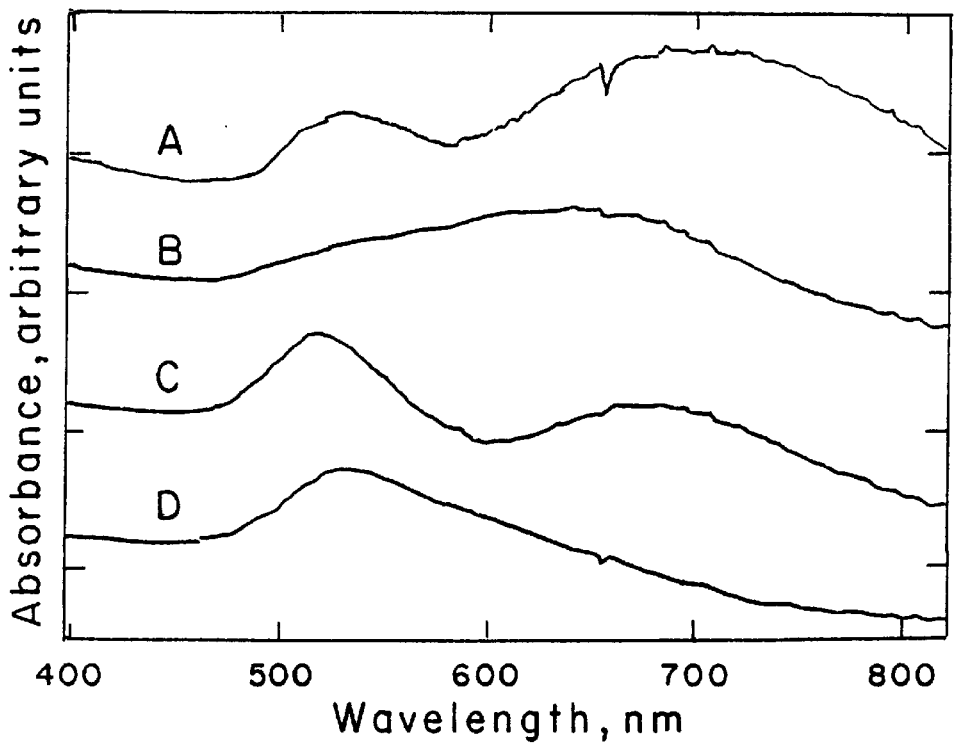
FIG. 6B illustrates the diversity of optical properties attainable through the method of the present invention.

FIG. 6A shows absorbance spectra for solutions of Au colloid (13 nm diameter). Unaggregated Au has a $\lambda_{max}$ at 520 nm, while aggregated Au exhibits a second, red-shifted absorbance centered at 700 nm. The sol was aggregated via addition of a small volume of concentrated NaCl solution. FIG. 6B shows absorbance spectra of quartz slides derivatized for 14 h in neat silane and for 24 h in colloidal Au: (A) APTMS, 30 nm Au; (B) APTMS, 13 nm Au; (C) MPMDMS, 30 nm Au; (D) MPMDMS, 13 nm Au.

Thus, for surfaces with the same polymer and containing a single size of particle, difference in optical properties must be attributed to differences in coverage (and therefore, average interparticle spacing). For example, spectra B and D are of immobilized 13 nm-diameter Au on quartz substrates derivatized with amino (APTMS)- and sulfhydryl (MPMDMS)-functionalized siloxane polymers, respectively. Relatively strong interparticle coupling is found in B, as evidenced by the presence of the collective surface plasmon absorbance feature, but is absent (or significantly weaker) in D. Since the area probed by the uv-vis beam is constant, and since the Au particle coating is homogenous over the entire surface, the stronger interparticle coupling results from an increased particle density. Whether this difference is attributable to a higher concentration of pendant functional groups in surface-confined APTMS than for MPMDMS, an increased affinity of Au for amine over sulfhydryl, or some other factor is under investigation.

These surfaces are fundamentally different from those prepared by evaporation of drop-coated colloidal Au solutions. Evaporated substrates exhibit complete colloid aggregation, sometimes to the extent of producing films that to the eye look like bulk Au. In contrast, the protocol described herein involves no bulk aggregation on the surface. Furthermore, with adequate rinsing between the polymer formation and colloid derivatization steps, there is no aggregation of particles in solution; immersion of the polymer-functionalized substrate into a colloidal Au solution, and subsequent removal of the colloid-derivatized surface, does not appreciably change the optical spectrum of the colloidal Au solution. We have also shown that colloid immobilization is not a sedimentation reaction by performing derivatizations upside down. Thus, immobilization of colloids on a polymer-functionalized glass substrate suspended upside down in solution yields colloidal surfaces indistinguishable from those obtained by complete immersion. Similarly, polymer-coated TEM grids can be derivatized with Au by flotation on aqueous colloidal solutions.

Figure 7:
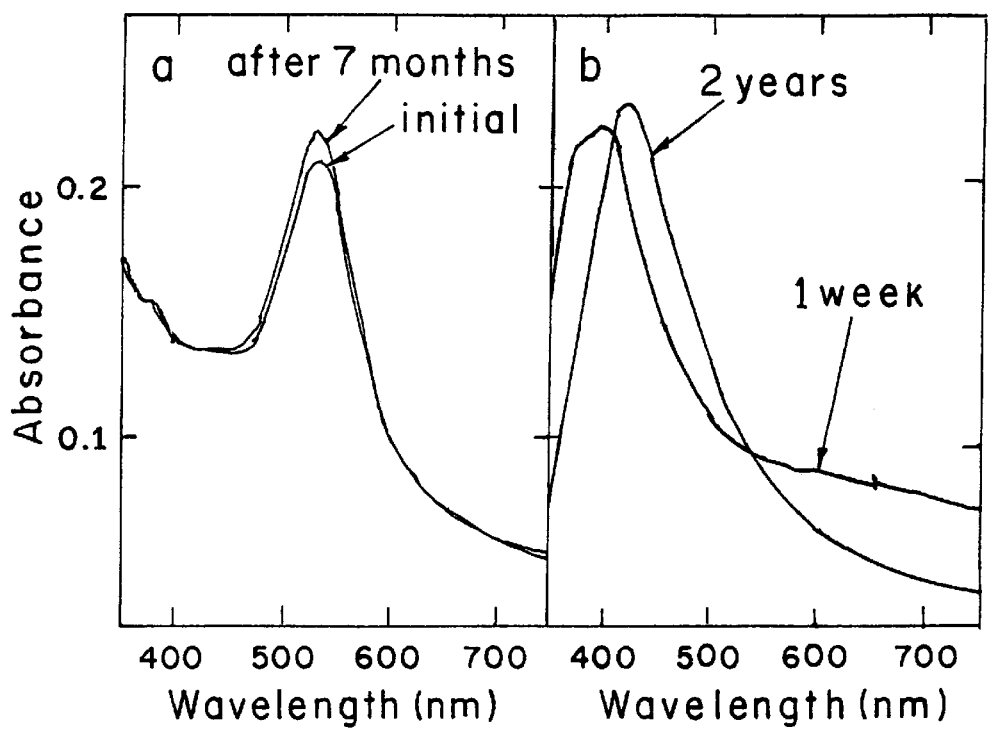
FIG. 7 illustrates the optical stability of the Au colloid-based monolayers of the present invention.

Once attached, the binding of colloidal Au to derivatized surfaces is extremely strong and essentially irreversible. There is very little change in the optical spectrum of an Au colloid-based monolayer after storgage for 7 months in H$_2$O (FIG. 7). Ag-based surfaces are also very durable, with no loss of particles over 2 years. For Ag, a shift of $\lambda_{max}$ from 396 to 420 nm may reflect particle aging, as has previously been shown for Ag colloids [Henglein, A. *J. Phys. Chem.* 1993, 97, 5457–71 and references therein. An alternative explanation for the shift is that bacterial growth in solution, against which no precautions were taken, leads to adsorption of protein on the particle surface (see FIG. 3)]. More importantly, these surfaces are rugged enough to survive exposure to appreciable concentrations of aggregating agents. Thus, exposure of an MPMDMS-based Au colloid surface to 5 mM mercaptoethanol does not alter the optical spectrum, indicating that particle aggregation has not taken place (data not shown). It is significant that the same concentration of aqueous mercaptoethanol instantaneously aggregates colloidal Au and Ag in solution. The high durability of these substrates is further manifested by their resistance toward ligand exchange: solution RS$^-$does not displace surface RS$^-$/Au bonds. Indeed, neat mercaptoethanol is needed to effect particle removal. Likewise, immersion of an Au-coated substrate into a solution of H$_2$O at 75° C. for a period of one hour had no effect on the optical spectrum. Equivalent stabilities are found for surfaces based on NH$_2$-Au linkages.

FIG. 7A shows absorbance spectra for a glass slide derivatized for 24 h in APTMS (diluted 1:4 with CH$_3$OH) and for 11 days in colloidal Au (13 nm). FIG. 7B shows absorbance spectra for a glass slide derivatized for 14 h in neat MPMDMS and for 1 week in colloidal Ag. After the initial optical spectra were recorded, slides were stored in H$_2$O until the final spectra were taken.

Figure 8:
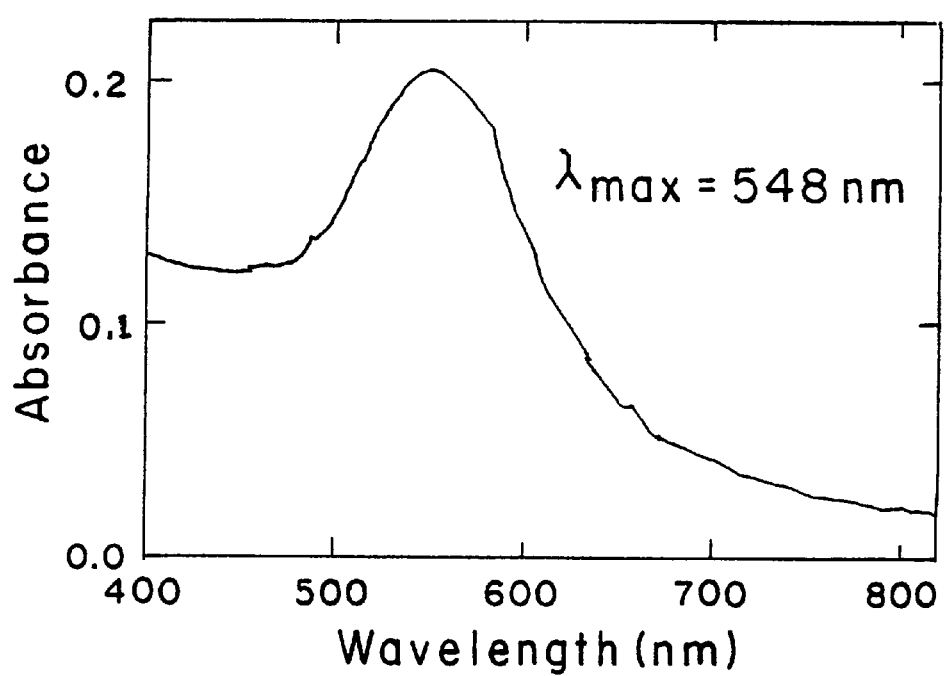
FIG. 8 shows the optical spectrum for a MP-biocytin coated quartz slide containing a monolayer of Au derivatized with BSA and streptavidin.

Surfaces based on non-covalent interactions (FIG. 1) possess optical properties completely analogous to those prepared by covalent attachment (FIG. 8). An important aspect of these data and of the concept described in FIG. 1 is that the biological activity (i.e. biotin binding) of streptavidin adsorbed on colloidal Au is necessarily retained: unmodified Au particles and particles coated completely with a protein that doesn't specifically bind biotin (i.e. BSA) do not lead to surface formation in the presence of biotinylated substrates. The retention of biological function contrasts sharply with streptavidin adsorbed at bulk Au surfaces, for which biological activity is compromised [Ebersole, R. C.; Miller, J. A.; Moran, J. R.; Ward, M. D. *J. Am. Chem. Soc.* 1990, 112, 3239–41]. The use of colloidal Au as a histochemical and cytochemical marker is based on the tendency of proteins adsorbed to small Au particles to retain their biological function. A major advantages of these surfaces, then, is their biocompatibility. Because they are composed of isolated colloidal particles, the behavior of the surface mirrors the behavior of particles in solution. The creation of macroscopic metal surfaces with high, nanometer-scale biocompatibility is important for biosensor applications, and reinforces the importance of maintaining some interparticle spacing, for only under these conditions can single particle behavior toward biomolecules be assured. Of course, the biomolecule itself may be the spacer . A final comment on FIG. 1 concerns the use of a coating protein to completely isolate Au particles. For the data in FIG. 8, BSA was used, meaning that each particle had multiple BSA molecules adsorbed for each streptavidin bound. (Note the peak shift of roughly 20 nm for $\lambda_{max}$, reflecting a change in local dielectric constant of proteins relative to H$_2$O.) However, this choice is arbitrary; it is possible to prepare particle-based Au surfaces where each particle is pre-coated with a protein of interest.

Transmission Electron Microscopy

Figure 9A:
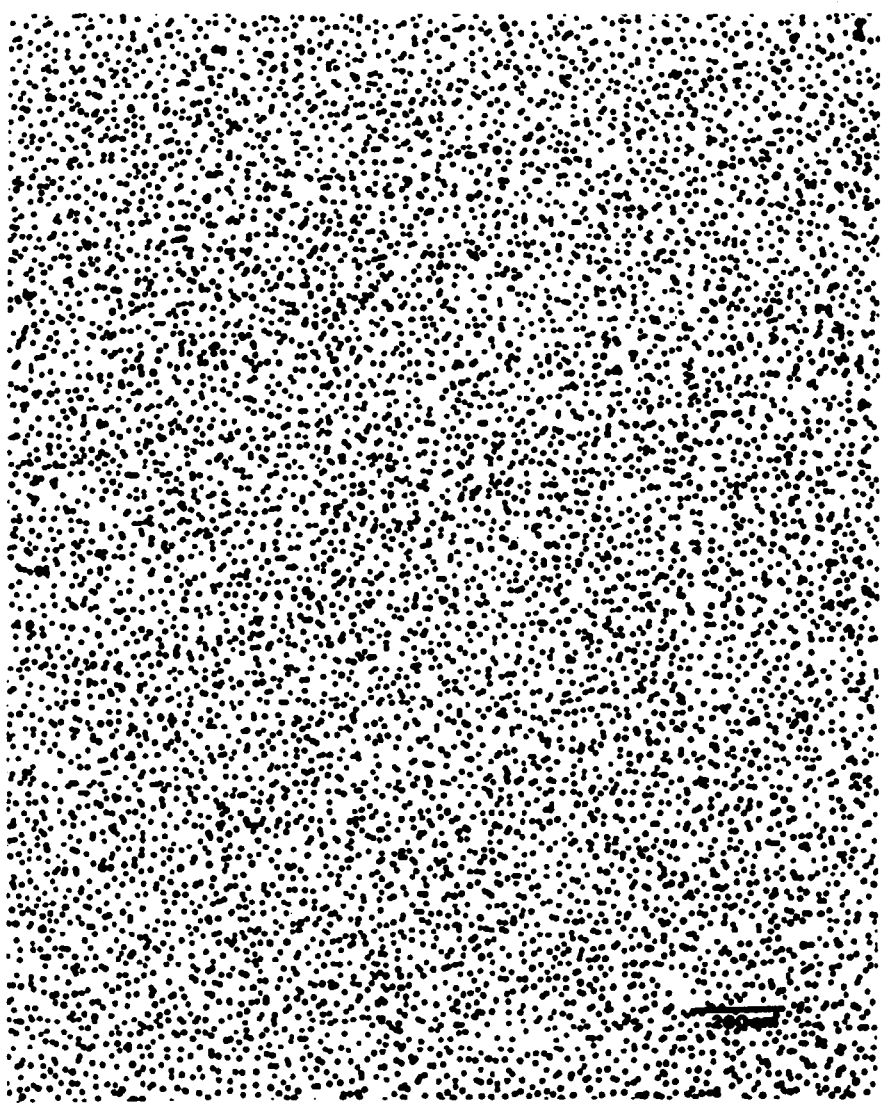
FIGS. 9A–9B show TEM micrographs of a colloidal Au surface prepared by the method of the present invention.
Figure 9B:
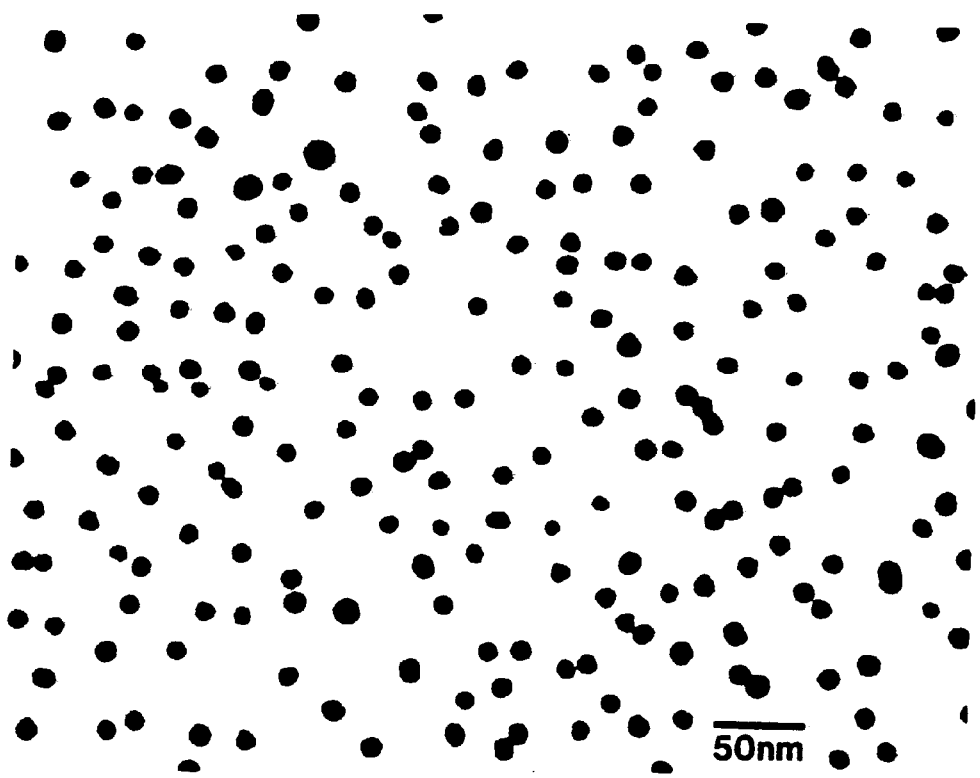

Direct evidence concerning the morphology and interparticle spacing comes from transmission electron microscopy studies of colloidal Au bound to polymers on TEM grids. These were prepared using commercially available formvar-coated Cu TEM grids possessing a thin sputter-coated overlayer of $SiO_1$. Careful treatment of these fragile surfaces with organosilane followed by colloidal Au yielded surfaces that could be directly imaged. FIG. 9A shows two magnifications of a surface derivatized in this manner with 13-nm colloidal Au. The areas shown in these micrographs are roughly 4.0 mm² for the top panel and 0.2 mm² for the bottom panel, and are representative of the entire sample. FIGS. 9, 9A & 9B show TEM micrographs of a colloidal Au surface prepared by derivatizing an $SiO_x$-coated TEM grid for 2.5 h in neat CPDMMS and for 12 h in 13 nm Au colloid. Areas depicted are approximately as follows: (top) 4.0 mm², (bottom) 0.2 mm².

Examination of these images verifies several critical aspects of the strategy delineated by FIG. 1: (1) there is a single two-dimensional submonolayer of colloidal Au; (2) the particles are closely spaced but not aggregated in two dimensions; (3) the particle coverage is uniform over areas macroscopic compared to the particle size; (4) the roughness is uniform and defined solely by the particle diameter; and (5) there appears to be a limitation to the number of particles that can be bound per unit area, with only 15%–20% of the surface covered. The observed distribution of particles extends over macroscopic areas, i.e. 3 mm×3 mm, the size of the TEM samples that we typically prepare.

Figure 9C:
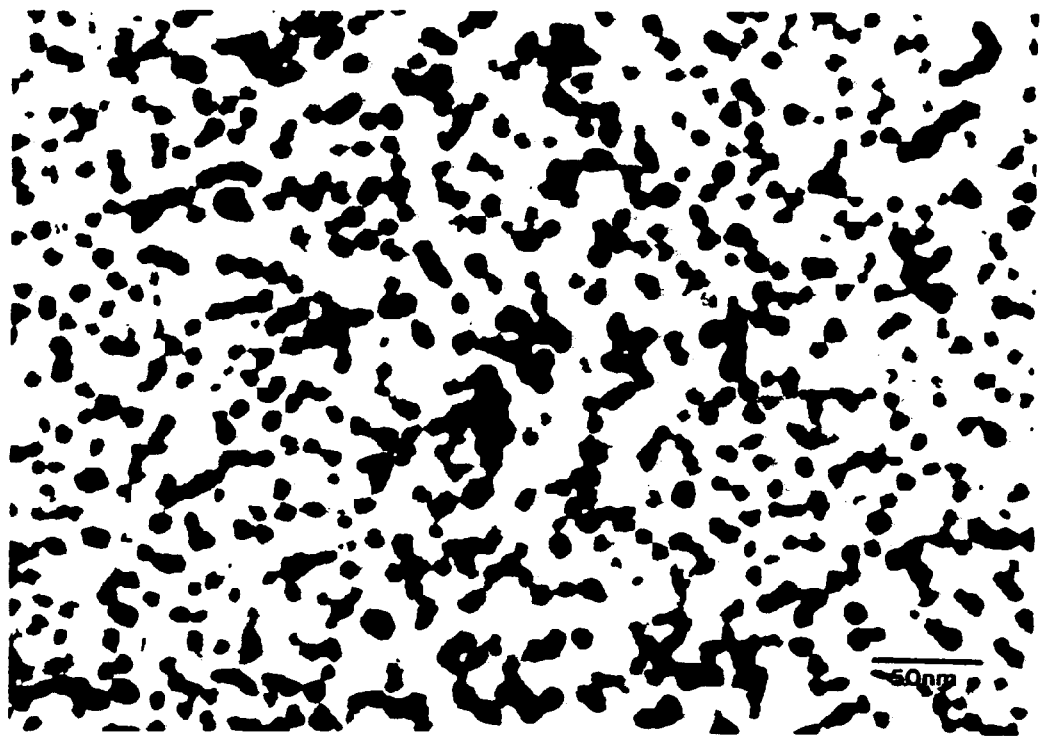
FIG. 9C shows a TEM micrograph of a formvar-coated TEM grid which was floated in colloidal Au for 2 days (not the method of the present invention).

It is well-known that aggregation of colloidal Au produces fractal clusters and strings. In the Creighton group's groundbreaking work on colloid SERS, two-dimensional strings of SERS-active particles were imaged by TEM [Jeanmaire, D. L.; Van Duyne, R. P. *J. Electroanal. Chem.* 1977, 84, 1–20]. Such species are not seen here, and the small percentage of dimers and trimers are invariably found in colloidal Au solutions as prepared. Weitz and co-workers have characterized the fractal dimension of aggregated Au and correlated it to SERS activity [Weitz, D. A.; Lin, M. Y. *Surf. Sci.* 1985, 158, 147–64]. Again, these large aggregates are not seen in images of carefully prepared surfaces. By way of contrast, FIG. 9C depicts a TEM image of colloidal Au on a non-functionalized, formvar-coated grid. Three-dimensional clusters of particles are clearly present in addition to isolated particles; the inability to achieve a good focus further signifies the existence of multiple layers of colloidal particles. Such species are not observed on the grids from which the data in FIGS. 9A and 9B was extracted. Rather, observation of closely-spaced, predominantly unaggregated colloidal particles confirms the arguments made above based on optical spectroscopy. The fact that all the colloidal particles are confined to nearly a single plane, as evidenced by good focus over large areas, suggests that for these surfaces, the roughness of the underlying organosilane film and/or substrate is comparable to the particle diameter or smaller. In accord with this notion, several studies of organosilane polymer films on smooth surfaces indicate a thickness <20 Å [Dressick, W. J.; Dulcey, C. S.; Georger, J. H., Jr.; Calabrese, G. S.; Calvert, J. M. *J. Electrochem. Soc.* 1994, 141, 210–20; Karrasch, S.; Dolder, M.; Schabert, F.; Ramsden, J.; Engel, A. *Biophys. J.* 1993, 65, 2437–46; Nakagawa, T.; Ogawa, K.; Kurumizawa, T. *Langmuir* 1994, 10, 525–9].

The tendency toward even spacing between particles observed in FIG. 8 results from electrostatic factors. It is known that colloidal particles are negatively charged and thus naturally repel one another, and that aggregation occurs only under conditions where this interparticle repulsion is screened. Within this framework, the protocol described here is self-assembly, in that long range order arises from secondary interactions between individual particles, as opposed to particle-surface interactions.

Surface Enhanced Raman Scattering (SERS)

Figure 10A:
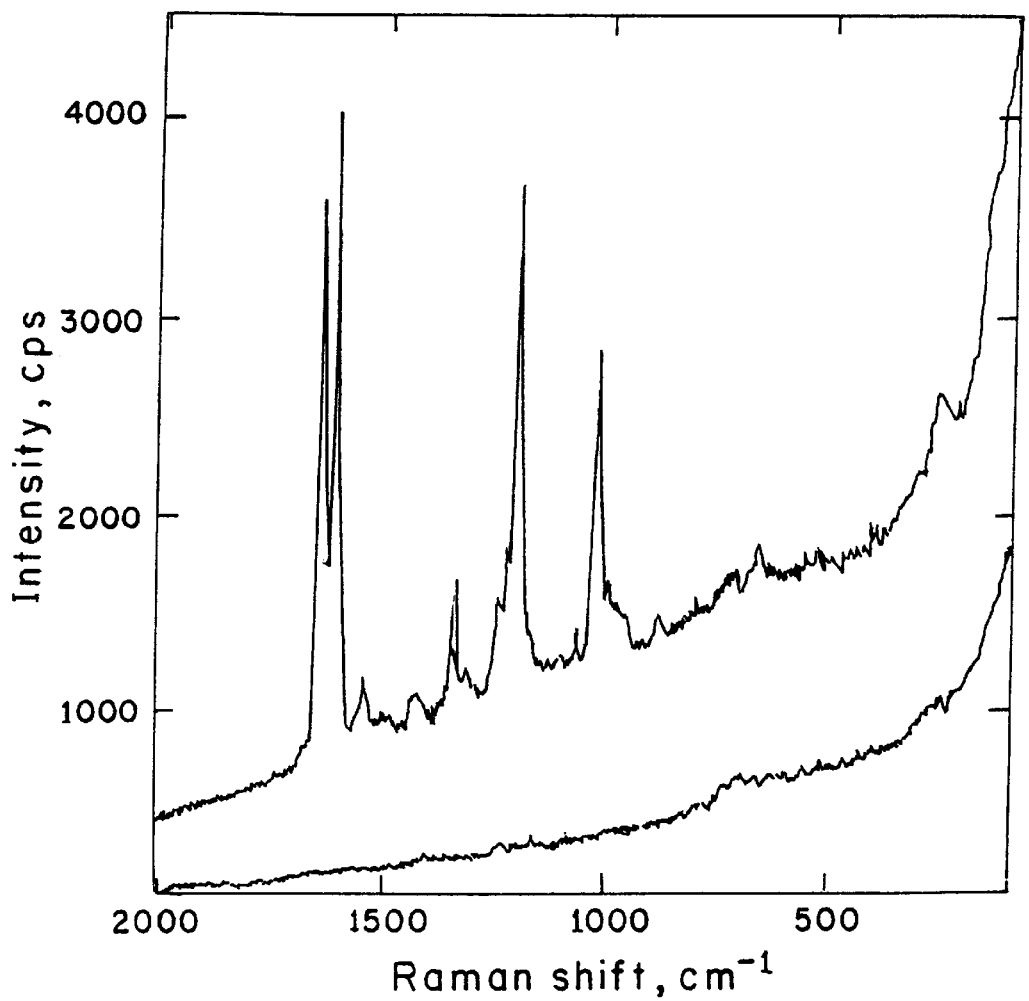
FIG. 10A shows a SERS spectrum of BPE drop-coated on a colloid Au monolayer on a functionalized TEM grid, as well as the SERS spectrum of the adsorbate-free surface.

One of the principle objectives of assembly of macroscopic metal surfaces exhibiting controlled roughness is to prepare well-defined, reproducible SERS-active substrates. The optical spectra show that the particle spacing is small compared to 1, suggesting that these particle arrays should be SERS-active. FIG. 10A shows the SERS spectrum of 5 nmol of BPE drop-coated onto a colloid monolayer on a functionalized TEM grid, as well as the SERS spectrum of the adsorbate-free surface. These data are extremely significant because they were obtained on the same type of surface imaged by TEM in FIG. 8. In the absence of adsorbate, no major features are observed in the Raman spectrum, indicating SERS from the polymer underlayer is weak. Typically, a low energy mode is observed for the S-Au vibration from MPMDMS-derived films, but little else is easily discerned.

Figure 10B:
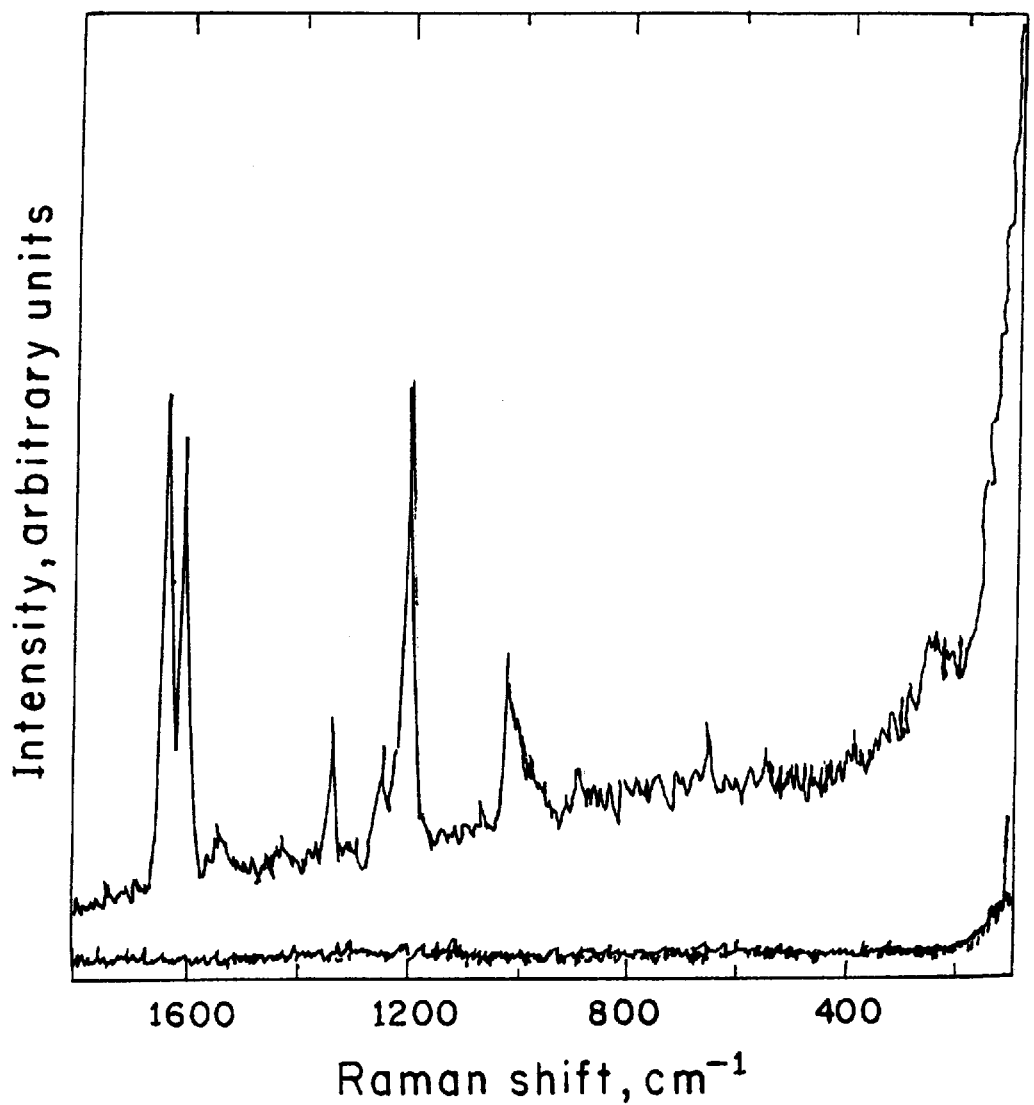
FIG. 10B shows a SERS spectrum of BPE drop-coated on a colloid Au monolayer on a $HO_2C(CH_2)_{16}SH/Au/Cr/Si$ substrate, as well as the SERS spectrum of the adsorbate-free surface.

FIG. 10A shows SERS spectrum of 5 ml of 1 mM BPE drop-coated onto an $SiO_x$ coated TEM grid derivatized with MPMDMS and 10 nm colloidal Au. Excitation source: 647.1 nm, 100 mW; 2 cm⁻¹ step, 2 s integration; 5 cm⁻¹ bandpass. The bottom spectrum was taken of the substrate surface prior to adsorption of BPE. The surface topography was identical to that depicted in FIG. 2. FIG. 10B shows SERS spectrum of BPE (10 ml, 1 mM in $CH_3OH$) drop-coated onto a colloidal Au (10 nm diameter) monolayer prepared on a $HO_2C(CH_2)_{18}SH/Au/Cr/Si$ substrate (upper). Prior to adsorption of BPE, a background spectrum of the colloidal Au substrate was run (lower). Excitation source: 647.1 nm; 150 mW (BPE), 100 mW (background); 2 cm⁻¹ step, 1 s integration; 5 cm⁻¹ bandpass.

It is important to understand the factors responsible for the observed SERS behavior of these substrates: why do we see BPE and not the polymer underlayer? Most SERS studies of polymers show a number of polymer-related bands. However, in those studies, the polymers completely surrounded the colloidal particles, while in this work, if the idealized geometry in Scheme I is reasonable (as the TEM data in FIG. 8 suggest is the case), only a small fraction of the colloid surface contacts polymer. For a particle with diameter=2r, the fraction of a sphere's surface area covered by a polymer with x nm vertical flexibility (over a horizontal distance 2r) is equal to:

$$\frac{\cos^{-1}[(r-x)/r]}{p} \tag{1}$$

In our system, using r=6 nm and x=1 nm (a vast overestimate, considering the length of the —$CH_2CH_2CH_2A$ tail is itself <1 nm), the fraction of total surface area exposed to polymer is 0.186. In other words, the ratio of adsorbate molecules at monolayer coverage to polymer tails is at minimum 5:1, and more likely closer to 10:1.

Another factor influencing the SERS enhancement is the Raman scattering cross-section. BPE is an exceptionally strong scatterer, while alkanes yield very weak Raman spectra. Bryant et al. have measured SERS spectra of octadecanthiols on Au foil; using a CCD, very long (10 min)

integration times were required. A third consideration is the magnitude the electric fields responsible for the electromagnetic enhancement. The largest fields are expected to occur in the plane of the particles, not in the plane normal to the substrate, i.e. Raman spectra of molecules adsorbed in this region are enhanced to a greater extent than those adsorbed elsewhere, and from our calculations above, only BPE can access this region. Finally, chemical enhancement effects in SERS certainly favor observation of enhanced Raman scattering from the nitrogen-containing BPE versus an alkane. The combination of these factors all favor observation of BPE SERS, and help explain the consistently observed finding that, over the region between 400–1700 $cm^{-1}$, very weak or no SERS spectra are seen for underlying films. A benefit of these substrates is thus the lack of background spectra, simplifying the data acquisition process. On the other hand, these substrates, like many others previously described, may not be sufficiently enhancing to measure Raman spectra for weak scatterers or poor adsorbates.

Because the Raman intensity of BPE adsorbed onto organosilane-coated glass slides is too small for us to measure, we crudely estimated how enhancing these surfaces are by comparing the solution concentration [x] of BPE needed to yield the same normal Raman spectrum as we obtained for a BPE concentration [y] in the presence of an Au colloid monolayer. Typically, $x/y \geq 10^4$. This number is in line with enhancements measured at roughened Au electrodes. The spectra yielding these enhancement factors (data not shown) are less than a factor of ten more intense than the data in FIG. 10A. Thus, enhancement factors of >1000 can routinely be obtained from arrays of closely spaced but non-contacting particles. Importantly, identical spectra are obtained on substrates in which BPE was adsorbed from solution; in fact, our experiments are routinely carried out in this fashion.

Below are experimental details associated with colloid monolayer preparation:

Materials. The following materials were obtained from Aldrich: $HAuCl_4 \cdot 3H_2O$, $AgNO_3$, trisodium citrate dihydrate, trans-1,2 bis(4-pyridyl)ethylene (BPE), and trimethoxy-propylsilane. The following organosilanes were obtained from Hüls America, Inc., and used as received: (3-aminopropyl)trimethoxysilane (APTMS), (3-cyanopropyldimethyl)methoxysilane (CPDMMS), (3-mercaptopropylmethyl)dimethoxysilane (MPMDMS), and 3-cyanopropyltriethoxysilane (CPTES). Concentrated HCl, $HNO_3$, and $H_2SO_4$ were purchased from J. T. Baker Inc., and 30% $H_2O_2$ was obtained from VWR. $CH_3OH$ (spectrophotometric grade) was obtained from EM Science; all $H_2O$ was 18 MW, distilled through a Barnstead Nanopure water purification system. Streptavidin, bovine serum albumin (BSA), and 3-(N-maleimidopropionyl)biocytin (MP-biocytin) were purchased from Sigma. BPE was recrystallized several times from a mixture of $H_2O$ and $CH_3OH$; the other materials were used as received. Substrates were obtained as follows: glass and quartz microscope slides from Fisher Scientific and Technical Glass Products, respectively; $SiO_x$-coated TEM grids from Ted Pella, Inc.; and self-assembled monolayers (SAMs) of $HS(CH_2)_{18}CO_2H$ on Au foil from literature procedures [Bain, C. D.; Troughton, E. B.; Tao, Y.-T.; Evall, J.; Whitesides, G. M.; Nuzzo, R. G. *J. Am. Chem. Soc.* 1989, 111, 321–35].

Colloid Preparation. All glassware used in these preparations was thoroughly cleaned in aqua regia (3 parts HCl, 1 part $HNO_3$), rinsed in triply-distilled $H_2O$, and oven-dried prior to use. Au colloids were prepared according to Frens [Frens, G. *Nature Phys. Sci.* 1973, 241, 20–2] or Sutherland [Sutherland, W. S.; Winefordner, J. D. *J. Colloid. Interface Sci.* 1992, 48, 12941] with slight modifications. The following stock solutions were prepared from triply-distilled $H_2O$ that had been filtered through a 0.8 mm membrane filter (Gelman Scientific): 1% $HAuCl_4$, 38.8 mM sodium citrate, and 1% sodium citrate. Other solutions were made fresh as needed using triply-distilled, filtered $H_2O$. Two typical Au preparations and one Ag preparation are described below.

Preparation I: Using a 1 L round bottom flask equipped with a condenser, 500 ml of 1 mM $HAuCl_4$ was brought to a rolling boil with vigorous stirring. Rapid addition of 50 ml of 38.8 mM sodium citrate to the vortex of the solution resulted in a color change from pale yellow to burgundy. Boiling was continued for 10 minutes; the heating mantle was then removed, and stirring was continued for an additional 15 minutes. After the solution reached room temperature, it was filtered through a 0.8 mm Gelman Membrane filter. The resulting solution of colloidal particles was characterized by an absorption maximum at 520 nm. Transmission electron microscopy (TEM) indicated a particle size of 13 nm±1.7 nm (100 particles sampled). Preparation II: In a 1 L round bottom flask equipped with a condenser, 500 ml of 0.01% $HAuCl_4$ was brought to a boil with vigorous stirring. To this solution was added 7.5 ml of 1% sodium citrate. The solution turned blue within 25 s; the final color change to red-violet occurred 70 s later. Boiling continued for an additional 10 min., the heating source was removed, and the colloid was stirred for another 15 min. TEM data indicated an average diameter of 18 nm±4.6 nm (89 particles sampled). Particle diameter was varied by adding larger or smaller amounts of sodium citrate to decrease or increase the particle size.

Ag colloid was prepared according to Lee and Meisel [Lee, P. C.; Meisel, D. *J. Phys. Chem.* 1982, 86, 3391–3395]. Using a heating plate and a 1 L flask, a solution of 90 mg AgNO3 in 500 ml of triply distilled $H_2O$ was brought to boiling with rapid stirring. To this solution was added 10 ml of 1% sodium citrate. Boiling continued for 30 min, after which time the flask was removed from the heat source, and the solution was diluted with triply distilled $H_2O$ to obtain a final volume of 420 ml.

All colloids were stored at room temperature in dark bottles and were generally used within 1–2 months after preparation. Samples for particle sizing by TEM were prepared by drop coating 10 ml of the colloid onto a formvar-coated Cu grid and allowing the sample to dry. Average sizes were determined by measuring diameters along a consistent axis throughout the sample.

Protein-Colloid Conjugates. Streptavidin-labelled Au particles were prepared using modifications of literature protocols [Liesi, P.; Julien, J.-P.; Vilja, P.; Grosveld, F.; Rechanrdt, L. *J. Histochem. Cytochem.* 1986, 34, 923]. To 25 ml of colloidal Au (preparation I) were added 0.725 ml of streptavidin (0.34 mg/ml in triply distilled $H_2O$) and 0.241 ml of BSA (7.24 mg/ml in triply distilled $H_2O$). The protein-Au conjugates were observed to sediment within 24 hours.

Surface Derivatization. Substrates were cleaned prior to derivatization as follows: glass and quartz, cut to dimensions of approximately 2 cm×0.7 cm, were cleaned for 10 minutes in a bath consisting of 4 parts $H_2SO_4$ to 1 part 30% $H_2O_2$ at 60° C. The samples were rinsed in spectrophotometric grade $CH_3OH$ and stored in this solvent until needed. $SiO_x$-coated TEM grids were cleaned in an ozone plasma for 30 min using a home-built instrument. Cleaning often preceded use of the grids by several weeks; during this period, the grids were stored in TEM grid holders in air.

Derivatization of glass and quartz substrates with alkoxysilanes was accomplished in the following manner: Clean substrates were submerged into vials of silane diluted 1 part to 4 parts with spectrophotometric grade $CH_3OH$. After a period of 24 h, the substrates were removed and rinsed profusely with $CH_3OH$ to remove unbound monomer from the surface. At this point, silanized substrates were stored in $CH_3OH$ until needed. Prior to derivatization with colloidal Au, the substrates were rinsed with $H_2O$; they were then immersed in vials of colloidal Au for 24 h. A final $H_2O$ rinse concluded the derivatization process. Similarly, carboxyl-terminated SAMs prepared on Au-coated silicon substrates were immersed in colloidal Au solutions for several days. The substrates were stored in $H_2O$ until needed for analysis.

Due to their inherent fragility and small size, greater care was required for the derivatization of TEM grids. Specifically, the $SiO_x$-coated TEM grids were immersed in neat silane for 3 h, followed by extensive methanol rinses and a $H_2O$ rinse. The rinsing was accomplished by pipetting solvent across the grid surface, or by swishing the grid back and forth in a vial of solvent. Effort was made to minimize the solvent flow perpendicular to the grid face in order to better preserve the formvar film. Finally, the grids were floated on a colloid solution for 12 h. Samples were rinsed with $H_2O$ and allowed to air dry on filter paper prior to analysis.

Sample Preparation. Two methods were employed for mounting the substrates for SERS detection. The first method involved mounting the substrate via double-sided tape to a black mount positioned in the laser beam (TEM grids, SAM substrate). In the second, the substrate (glass or quartz) was supported in the front of a quartz cuvette by means of a teflon block whose height was only ⅓ that of the sample. This cuvette could be filled with solvent or empty. The cuvette rested in a snug, home-built cuvette holder. Both sample configurations were mounted on a stage such that the sample position could be adjusted in all three dimensions. For measurements carried out in air, solutions of BPE in $CH_3OH$ were drop-coated onto the substrate surface and allowed to evaporate; alternatively, the cuvettes were placed in cuvettes containing known concentrations of BPE.

Instrumentation. SERS spectra were obtained with a Coherent $Kr^+$ ion laser, model 3000K, operated at 647.1 nm in $TEM_{00}$. Spectral scanning and detection were accomplished through the use of a Spex Model 1404 scanning double monochromator with a pair of 1800 grooves/mm gratings and a thermoelectrically-cooled Hamamatsu R928 photomultiplier tube housed in a Products for Research casing. Monochromator entrance and exit slits were typically set at 700 mm, and center slits were set at 1400 mm to yield an effective band pass of 5 $cm^{-1}$. Grating movement and spectral acquisition were controlled using the DM3000 software provided by Spex. Plasma lines were filtered out of the incident laser beam through the use of a band pass filter (Ealing ElectroOptics) or a pre-monochromator tuned to the 647 nm line (Optometrics). The laser beam was focused onto the substrate sample at an angle of <30° from the surface normal. Scattered radiation was collected and collimated with a Minolta 50 mm camera lens (f#1.2) and focused through a polarization scrambler (Spex) onto the entrance slits of the monochromator.

Absorption spectra were obtained using a Hewlett-Packard 8452A diode array spectrophotometer (2 nm spectral resolution, 1 s integration time). Again, substrates in quartz cuvettes were maintained in an upright position through the use of a teflon block. Transmission electron microscopy was performed on a JEOL Model 1200 EXII instrument operating at 80 kV accelerating voltage; the images were not manipulated, altered, or enhanced in any way.

Below are eight (8) further examples of colloid monolayer experimental protocols:

EXAMPLE 1

Surfaces Made From Seeded Colloidal Au Particles

Glass slides (2.5 cm×0.8 cm×1 mm) were cleaned in a mixture of $HCl:HNO_3$ (3:1). Slides were rinsed in $H_2O$ and $CH_3OH$ prior to derivatization for 18 h in a solution of aminopropyltrimethoxysilane (diluted 1:5 in $CH_3OH$). The derivatized surfaces were rinsed extensively in $CH_3OH$ and $H_2O$ prior to immersion in solutions of colloidal are described below. After 24 hours, the colloid derivatization was complete.

Au nuclei ("seeds") were prepared by adding 1 ml of 1% $Na_3$ citrate to a vigorously stirring solutions of 0.01% $HAuCl_4$. After 1 min., 1 ml of a solution of composition 0.075% $NaBH_4$ and 1% $Na_3$ citrate was added. Reaction continued for five minutes. The solution of nuclei was stored at 4° C. until needed.

The first seeded colloid was prepared by refluxing 1 ml of 1% $HAuCL_4.3H_2O$ with 100 ml of 18MΩwater with vigorous stirring. 0.4 ml of 1% $Na_3Citrate$ and 30 µl of the above described nuclei was added rapidly and boiled for an additional 15 minutes followed by cooling to RT. The resulting colloid was stored in a dark bottle.

A second seeded colloid was prepared by an identical method using 15 µl of nuclei instead of 30 µl.

| Colloid | Major | Minor | Std. Dev. | # of Part. |
|---|---|---|---|---|
| Nuclei | 2.64 | 2.03 | 1.04 | 131 |
| Seeded #1 | 52.7 | 43.7 | 5.24 | 70 |
| Seeded #2 | 93.4 | 68.0 | 20.0 | 16 |

Figure 11:
FIGS. 11–13 are TEM images of the colloidal particles prepared in accordance with example 1.
Figure 12:
Figure 13:
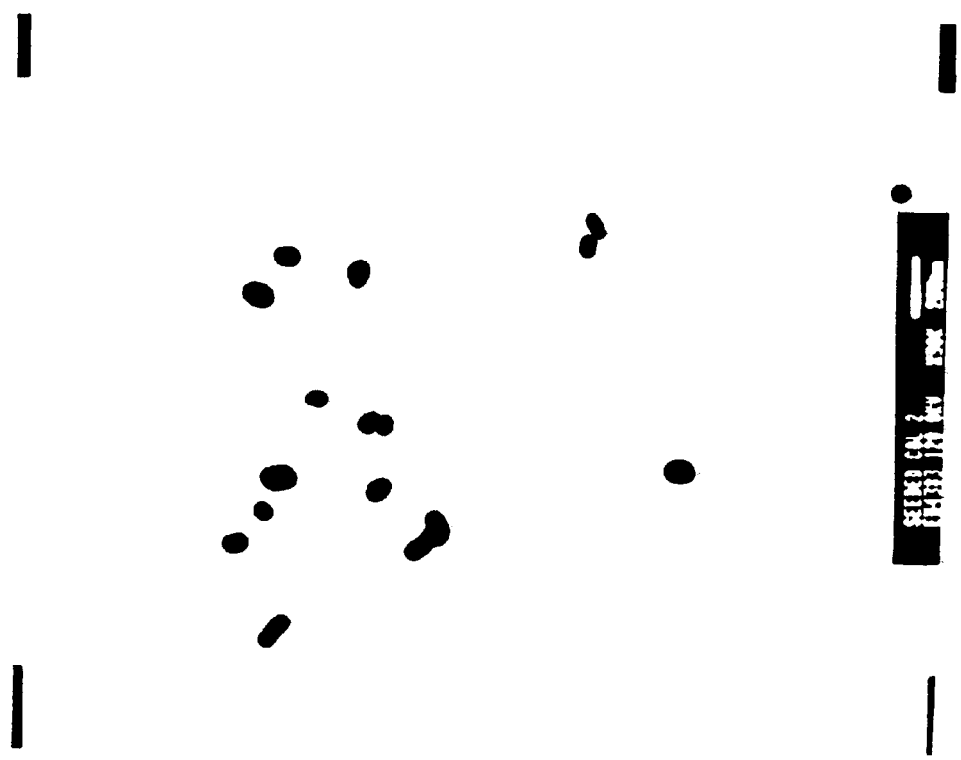
Figure 14:
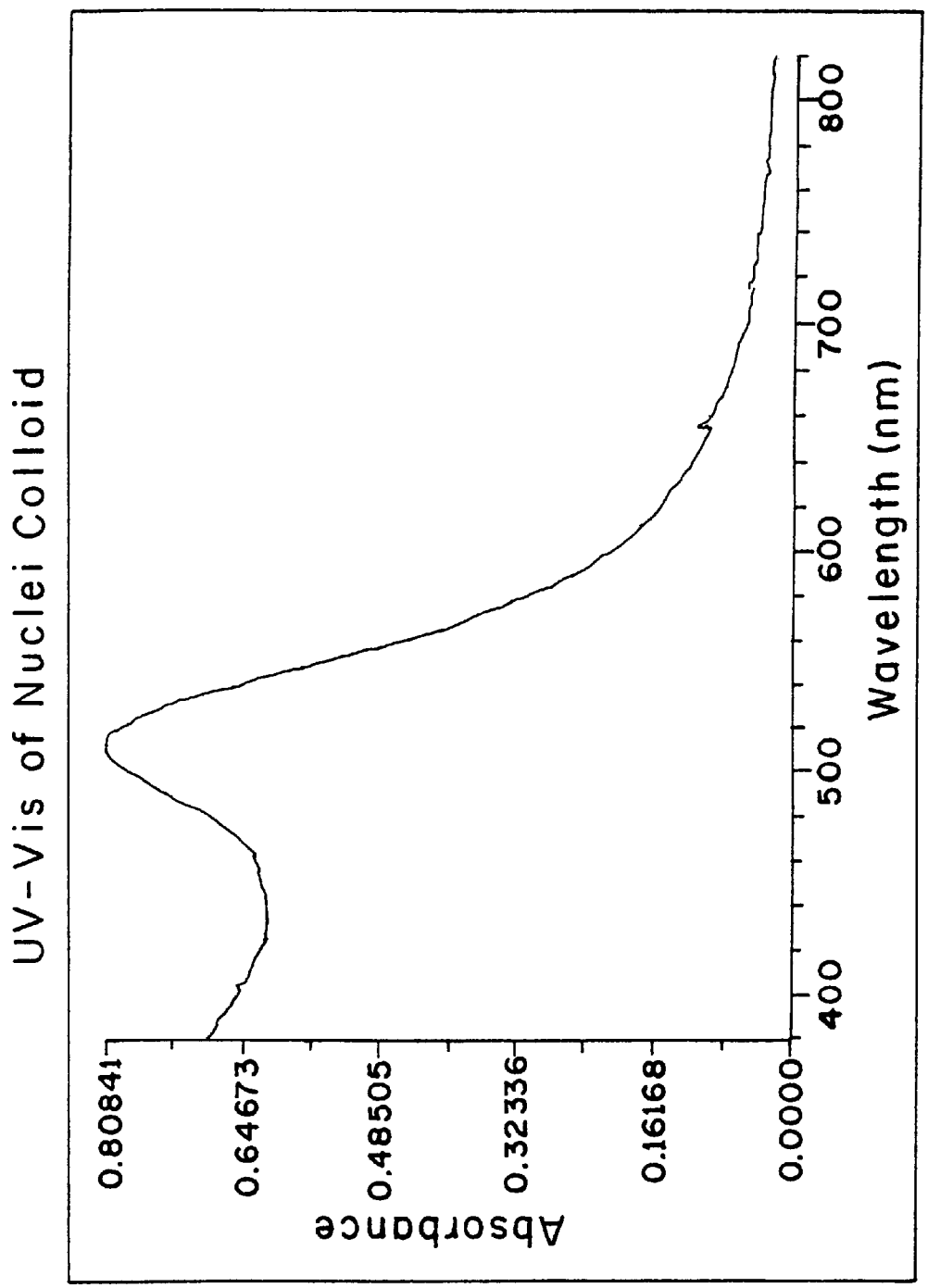
FIG. 14 is the solution optical spectrum of the seed nuclei of example 1.
Figure 15:
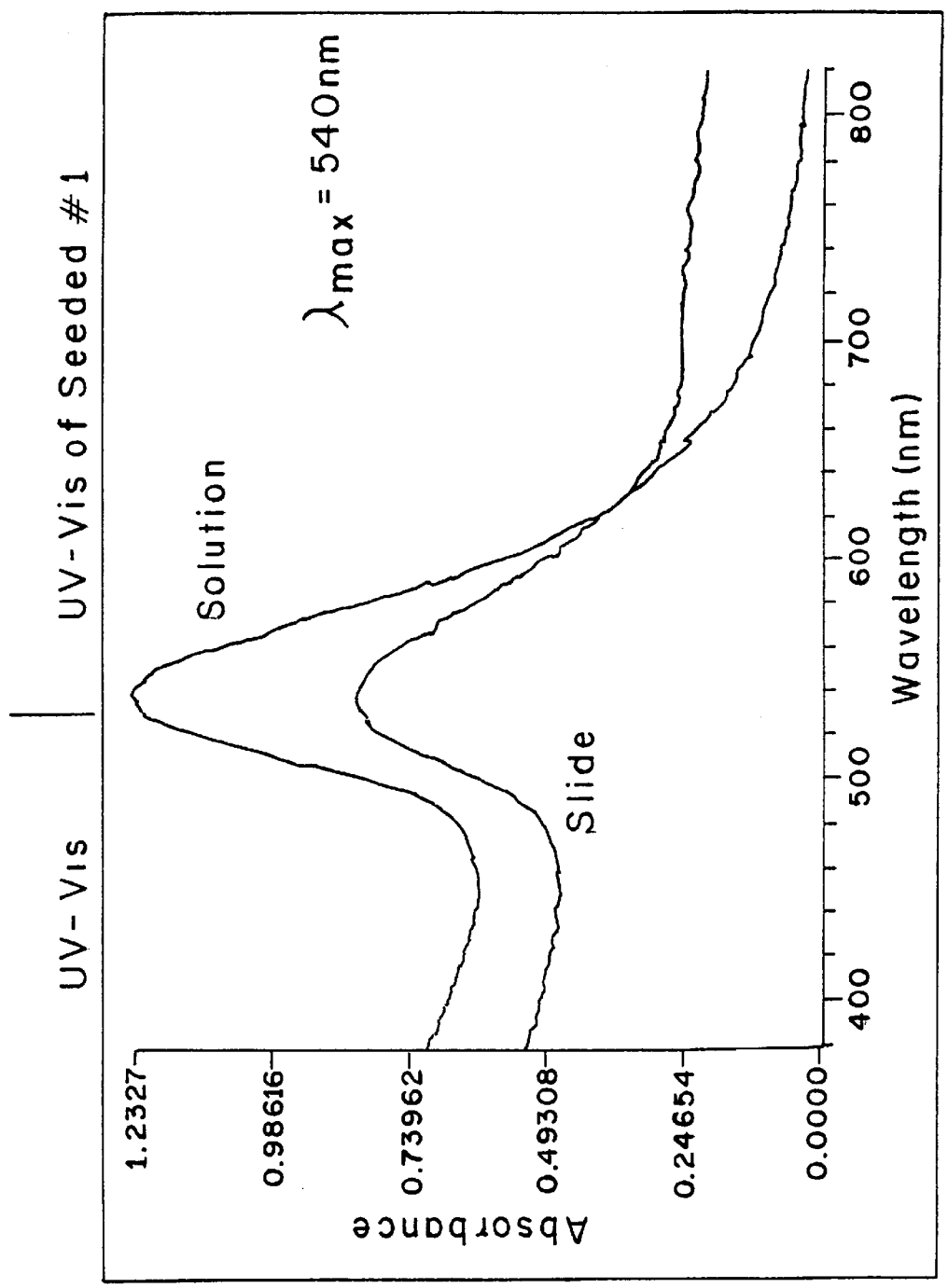
FIGS. 15–16 are uv-vis spectra of the larger particles derivatized on glass substrates and of the larger particles in solution as described in example 1.
Figure 16:
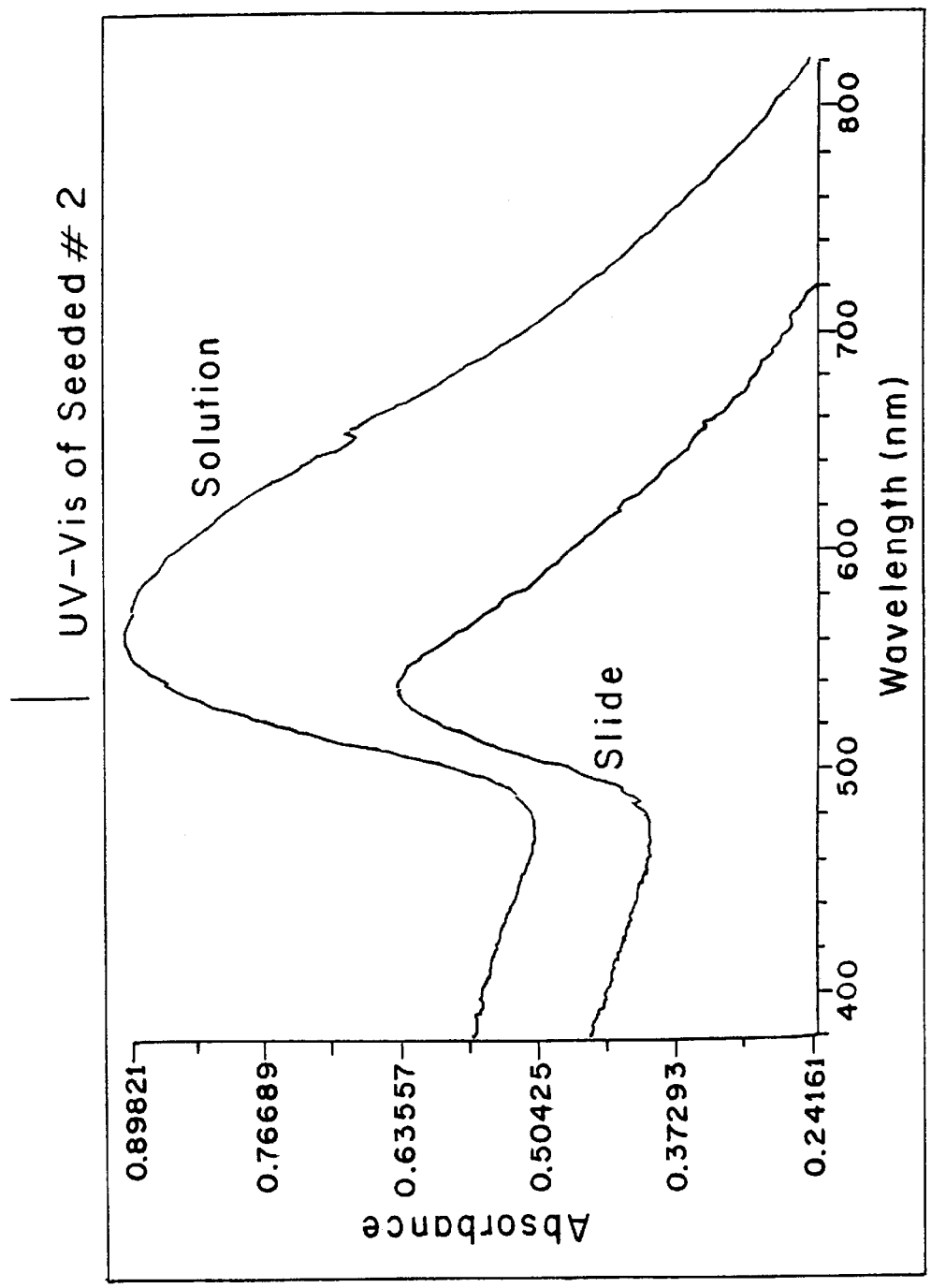

FIGS. 11–13 are TEM images of the particles. FIGS. 14 is the solution optical spectrum of the seed nuclei. FIGS. 15–16 are the uv-vis spectra of the larger particles derivatized on glass substrates and of the larger particles in solution.

EXAMPLE 2

Preparation of 2-layer Colloid Surfaces

Once a colloid monolayer is formed, it is possible to produce a multi-layered material by introducing a chemical linking agent and a second layer of particle. Possible linkers include 4,4'-bis-pyridylethylene, 4,4'bipyridyl, p-xylenedithiol, and mecaptoethylamine. Experimental protocol for preparation of a typical surface follows.

Figure 17:
FIG. 17 shows a TEM image of the colloidal surface in example 2 after the first layer of colloidal particles has been applied.
Figure 18:
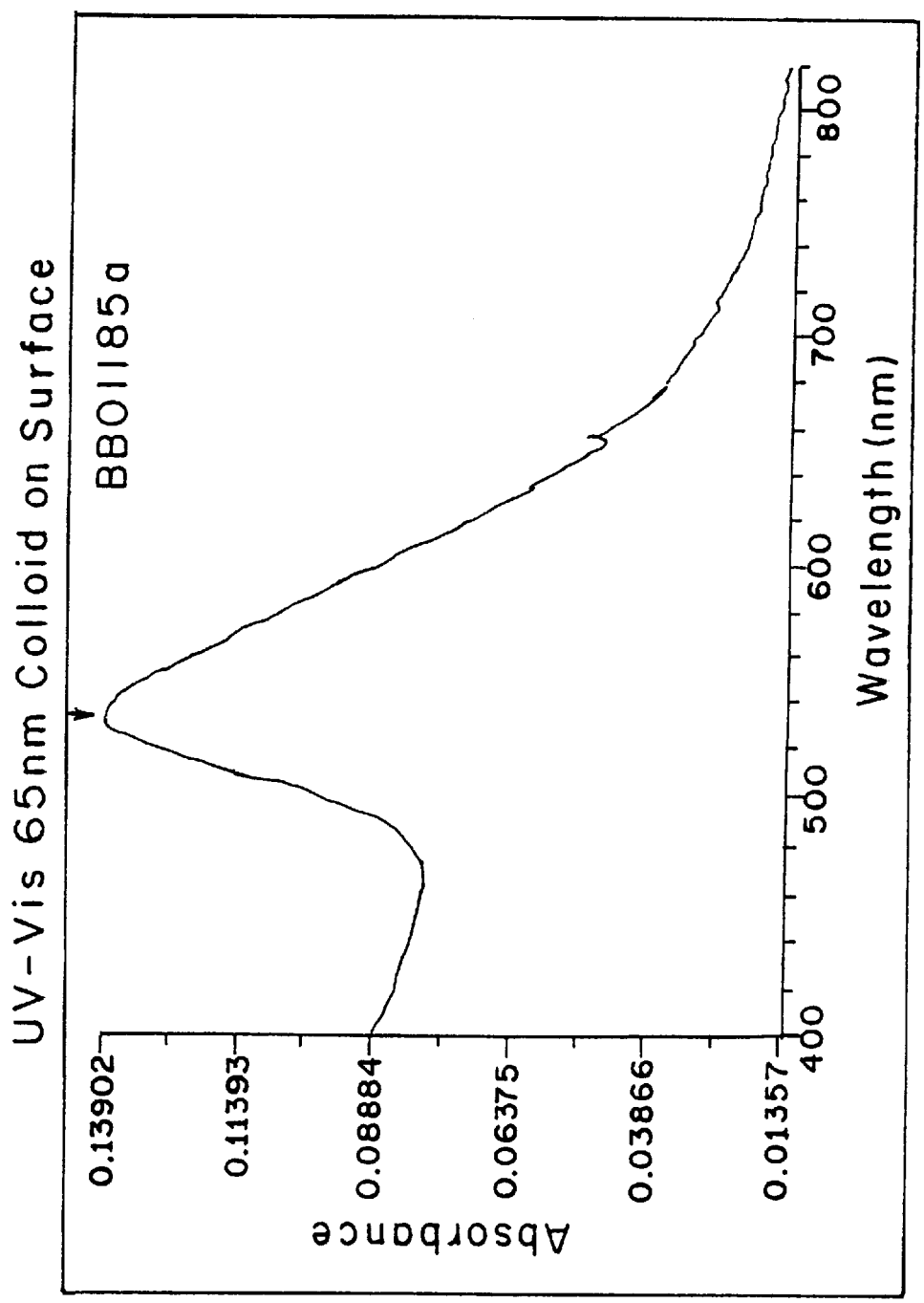
FIG. 18 shows an optical spectrum of the colloid surface in example 2 after the first layer of colloidal particles has been applied.
Figure 19:
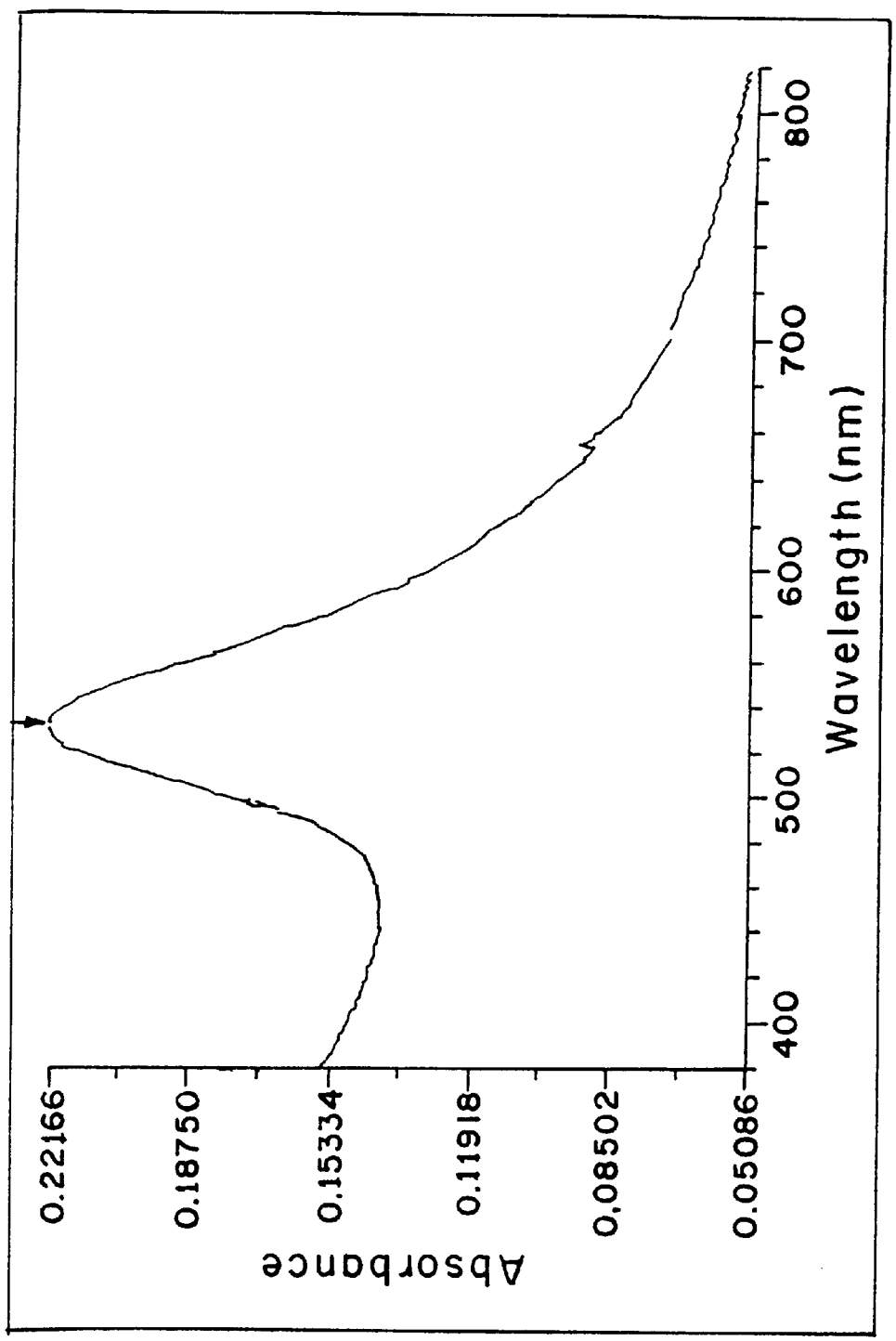
FIG. 19 shows an optical spectrum of the colloid surface in example 2 after the second layer of colloidal particles has been applied.

Glass slide surfaces, approximately 2 $cm^2$, were washed first in a solution of $HCl:HNO_3$ (3:1) followed by an $H_2O$ rinse and cleaning in a mixture of 30% $H_2O_2:H_2SO_4$ (1:4). The cleaned slides were placed in about 3 mL of a 1:10 solution of aminopropyltrimethylsiloxane (APTMS) in methanol for 1 hour. The slides were rinsed with water and placed in about 3 mL of a 7.0 $10^{-12}$ M colloid solution overnight. These particles had the following shape: 65.8 nm major axis, and 49.3 nm minor axis. The slides were again rinsed with water, and stored in water. A TEM image of the particles is shown in FIG. 17. The resulting optical spectrum is shown in FIG. 18. This surface was immersed for 5 minutes in 1 mM mercaptoethylamine in water and rinsed. This surface was then immersed in a 17 nM solution of 12 nm colloidal Au particles for 15 minutes. FIG. 19 is the resulting optical spectrum.

EXAMPLE 3

Protein Coated Au Colloid Monolayers

Quartz surfaces which had been cleaned in a mixture of $H_2SO_4$:$H_2O_2$ (4:1) were derivatized in neat silane solution for 2 days. After rinsing these surfaces in spectrophotometric grade $CH_3OH$, they were placed in a solution of 3-(N-maleimidopropionyl)-biocytin (0.31 mg/ml in 0.05M Tris buffer containing 0.1% BSA) for 18 h. Slides were rinsed in $H_2O$ and placed in solutions of the Au probe described below. The protein-Au probes had been aged for 1 hour prior to coating the slides; slides remained in solution overnight and were removed when the colloidal particles sedimented. Little to no coating was achieved in the first 5 h of exposure to the Au probes; optical spectra taken after the colloid sedimented indicated Au coating on all of the silane/biocytin surfaces employed, with $\lambda_{max}$=550 nm.

Protein-coated Au probes were prepared as follows: To 25 ml of a citrate-prepared Au colloid (12 nm diameter, 17 nM) was added 0.725 ml of streptavidin (0.34 mg/ml in triply distilled $H_2O$) and 0.241 ml of BSA (7.24 mg/ml in triply distilled $H_2O$). Within 4 hours, this solution showed some aggregation/sedimentation of particles, but particles were easily resuspended with shaking the solution. However, within 24 h, the particles had sedimented completely and could not be resuspended.

Quartz surfaces which had been cleaned in a mixture of $H_2SO_4$:$H_2O_2$ (4:1) were derivatized in neat silane solution for 2 days. After rinsing these surfaces in spectrophotometric grade $CH_3OH$, they were placed in a solution of 3-(N-maleimidopropionyl)-biocytin (0.31 mg/ml in 0.05M Tris buffer containing 0.1% BSA) for 18 h. Exposure of this surface to a streptavidin-coated Au colloid resulted in surface formation.

Figure 20:
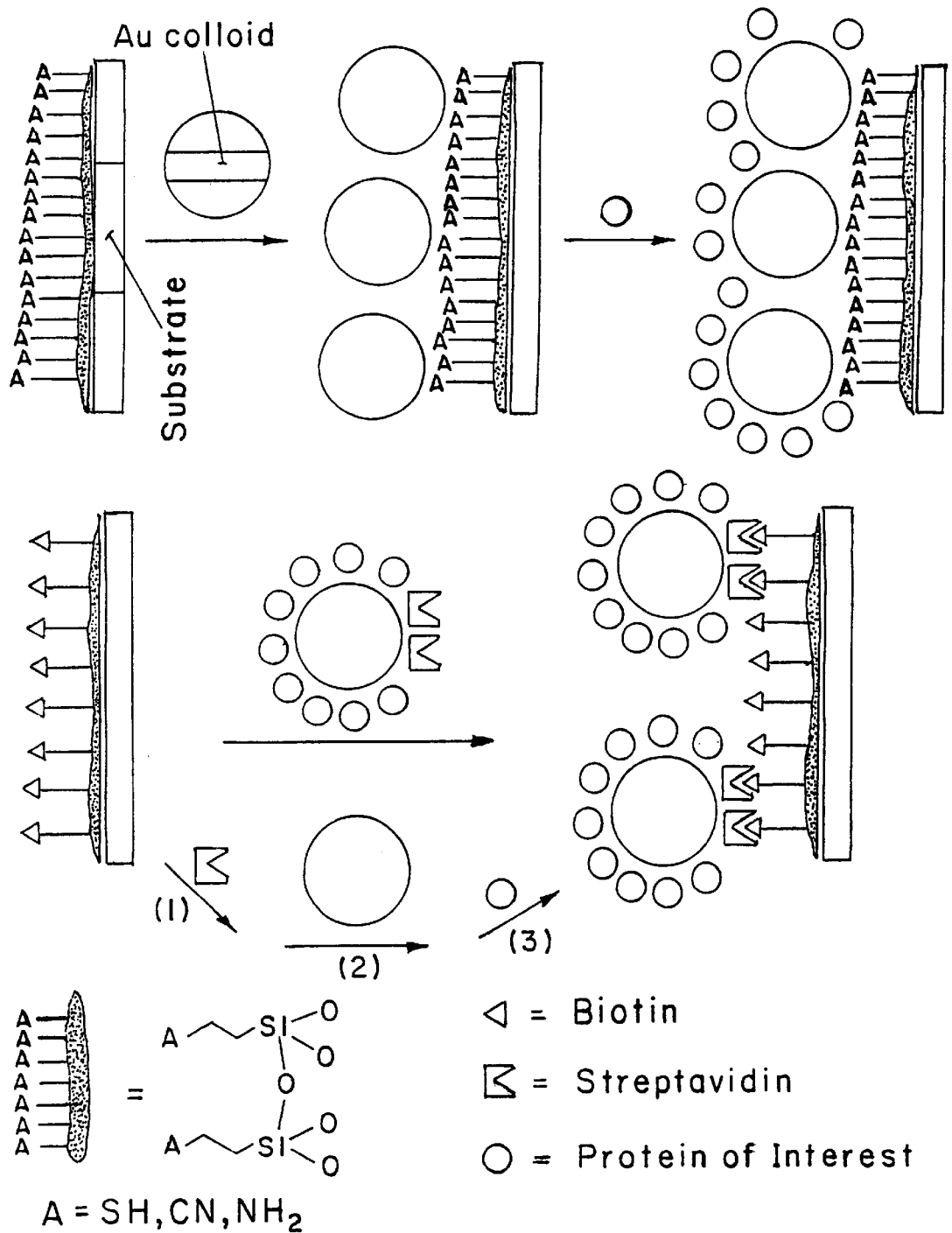
FIG. 20 shows non-covalent colloidal approaches to protein coated metal surfaces.
Figure 21:
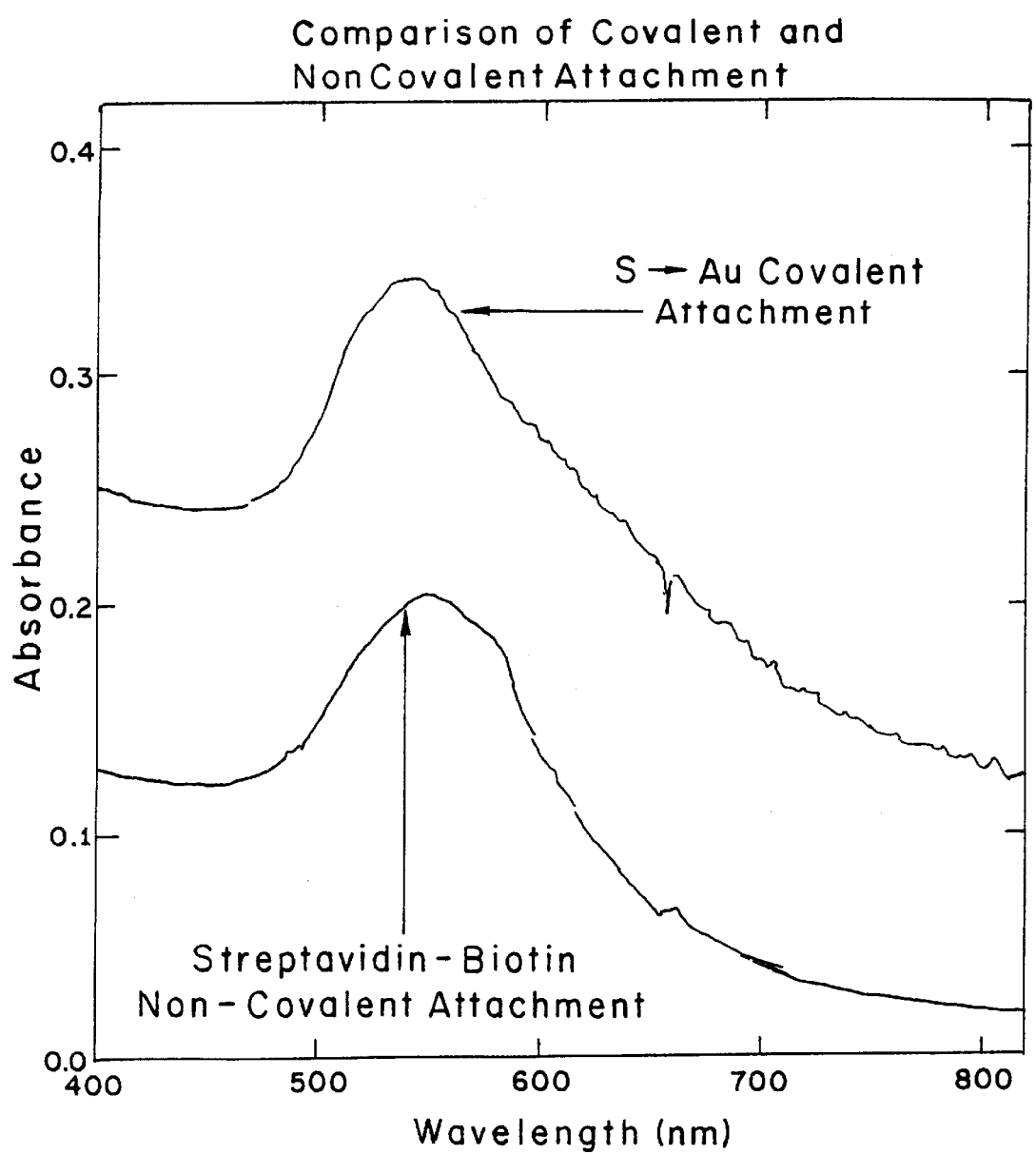
FIG. 21 is a comparison of the optical properties of covalent and non-covalent attachment.

FIG. 20 shows the strategies available for non-covalent attachment of colloids to surfaces, and how these strategies can be utilized to bind biomolecules to metals in a biocompatible fashion. FIG. 21 compares the coverages by covalent and non-covalent methods.

EXAMPLE 4

Detailed Experimental Protocols for the Production of Ag-coated Au Colloid Monolayers by Chemical or Electrochemial Reduction Materials The following materials were obtained form Aldrich: $HAuCl_4 \cdot 3H_2O$, $Na_2SO_4$, trisodium citrate dihydrate, pyridine, and N,N-dimethyl4-nitrosoaniline (p-NDMA). The following organosilanes were obtained from Hüls America, Inc.: 2-(diphenylphosphino)-ethyltriethoxysilane (DPPETES), 3-aminopropyltrimethoxysilane (APTMS), mercaptopropylmethyldimethoxysilane (MPMDMS) and 2-(trimethoxysilyl)ethyl-2-pyridine (PETMS). KCl, HCl, and $HNO_3$ were obtained from J. T. Baker. $Ru(NH_3)_6Cl_3$ was obtained from Johnson Matthey. Li Silver was obtained from Nanoprobes, Inc. Methanol (spectrophotometric grade) was obtained from EM Sciences. All chemicals were used as received. All $H_2O$ was 18 MΩ, distilled through a Barnstead Nanopure water purification system. Single component Ag epoxy was obtained from Epoxy Technologies, Inc and white expoxy was epoxi-patch from The Dexter Corporation. Glass microscope slides were obtained from Fisher Scientific, quartz slides from Technical Glass Products, and In-doped $SnO_2$ from PPG Industries, Inc.

Colloid Preparation

Colloidal Au particles of 18 nm±1 nm and 12 nm were prepared as described previously. The sols were characterized by optical spectroscopy.

Surface Derivitization

Glass and quartz microscope slides were cut to 25 mm×9 mm prior to cleaning in a bath of 4 parts $H_2SO_4$ to 1 part 30% $H_2O_2$ at 60° C. After rinsing in $H_2O_1$ slides were cleaned in a bath of 3:1 HCl:$HNO_3$. Slides were rinsed in $H_2O$ and stored in $CH_3OH$ until needed. Clean surfaces were placed in 2% (by volume) 2(diphenylphosphino) ethyltriethoxysilane or 2-pyridylethyltriethoxysilane in $CH_3OH$. Solutions were shaken vigorously and reacted for 24 hours. Substrates were then removed from solution and rinsed thoroughly in $CH_3OH$, then rinsed and stored in water. Silanized surfaces were immersed colloidal Au for 24 hours. Surfaces were then removed, rinsed several times in $H_2O$ and stored in $H_2O$. In-doped $SnO_2$ was cut to an approximate area of 3.0 $cm^2$. Copper wire was adhered to the $SnO_2$ with Ag epoxy. The copper wire was encased in glass tubing and sealed with white Epoxy-Patch The contact area was covered with a white epoxy. The electrodes were sonicated in neat reagent grade acetone, soap solution, and $H_2O$ for approximately 15 minutes each, then were soaked in approximately 3 M NaOH for over 2 hours. Clean electrodes were placed in aqueous APTMS (1% by wt.) for 5 minutes. Silanized electrodes were then rinsed with $H_2O$ and dried for 48 hours. The electrodes were placed in the Au colloid solution for 2 hours. Colloid-coated electrodes were then rinsed and stored in $H_2O$. The other $SnO_2$ samples were placed in neat MPMDMS for approximately 5 hours. The substrate was rinsed with $CH_3OH$ and air dried. The polymer-coated substrate was then placed into fresh Au colloid for at least 8 hours for high coverage $SnO_2$. The Au colloid-coated substrate was removed, rinsed with triply-distilled $H_2O$, and air dried.

Electrode Characterization

A 5 mM $Ru(NH_2)_6Cl_3$ in 0.1 M $Na_2SO_4$ was degassed with $N_2$ for over 15 minutes prior to analysis. An SCE was used as a reference electrode and Pt gauze was used as the counter electrode in all measurements.

Sample Preparation

Li Silver Reduction

Ag was reduced onto the colloid-coated slides by immersing the substrates in a solution of equal volumes of LI Silver enhancer and initiator solutions. Reaction time was varied between 5 and 30 minutes. Surfaces were then rinsed and stored in $H_2O$.

Ag Deposition

An electrolyte solution of 1 mM $Ag_2SO_4$ and 0.1 M $Na_2SO_4$ was degassed with $N_2$ for at least 15 minutes prior to the electrochemical deposition. A Pt gauze electrode was used as a counter electrode. A cyclic voltammogram was first done with the electrode scanning from 1.0 V to 0.0 V vs SCE at 50 mV/sec. A constant potential was applied to the electrode until a predetermined number of Coulombs had been counted. The cyclic voltammogram and the reduction of Ag were both done in the same solution under a blanket of $N_2$. The electrodes were then removed, UV-Vis spectra were collected, and the electrodes were stored in $H_2O$.

Surface Characterization

SERS of 0.5 M pyridine/0.1 M KCl solution on the electrodes were performed. The potentials were obtained with a Pt counter electrode and a SCE reference electrode and were varied from 0.0 V to −0.9 V. SERS of the Li Silver was done on 0.5 mM p-NDMA in $CH_3OH$. Experiments were performed with 632.8 nm excitation, 7.5 $cm^{-1}$ bandpass, 0.5 $cm^{-1}$ steps and 1 second integration.

Instrumentation

SERS spectra were obtained with a Spectra-Physics Model 127 HeNe ion laser operated at 632.8 nm. Raman spectra were acquired with a Spex Model 1403 scanning double monochromatic with a pair of 1800 groove/mm gratings and thermoelectrically-cooled Hamamatsu photomultiplier tube housed in a Products for Research casing. Monochromator entrance and exit slits were set for a spectral bandpass of 7.5 $cm^{-1}$. Spectral acquisition and grating movement were controlled via the DM3000 software provided by Spex. Plasma lines were filtered out of the incident beam through a band pass filter (Ealing ElectroOptics.) Incident light was focused at an angle ~<30° to the surface normal. Scattered radiation was collected and collimated with a Minolta 50 mm camera lens (f/#1.2) and focused through a polarization scrambler (Spex) onto the entrance slits of the monochromator. Substrates were supported by Teflon block (⅓ of sample height) in a quartz cuvette. The cuvette holder rested on a home-built stage adjustable in all three dimensions.

Optical spectra were obtained using a Hewlett-Packard 8452A diode array spectrophotometer with a 2 nm spectral resolution and 1 s integration time. Samples were supported in the cuvettes by use of the teflon block described above.

The cyclic voltammograms of the $Ru(NH_3)_6Cl_3$ were done on a Cypress Systems CS87 potentiostat. The cyclic voltammograms and the Ag deposition were carried out using an EG&G PAR 173/175 combination programmer/potentiostat, and recorded by a NGI Servogor 790 XY recorder. Ag deposition was monitored using a Linseis L6512B strip chart recorder. The potential during the Raman scans was held constant by a BAS CV27 potentiostat.

Atomic Force Microscopy (AFM) was performed on a Digital Instruments Nanoscope III Multimode AFM in tapping mode. The samples were cut to approximately 1 cm×1 cm and allowed to air dry. The scan size was 1.00 μm, and scan rate was 0.9988 Hz. X and Y axes are 1 μm with 0.2 μm divisions, and all the z-axis are 300 nm.

Figure 22:
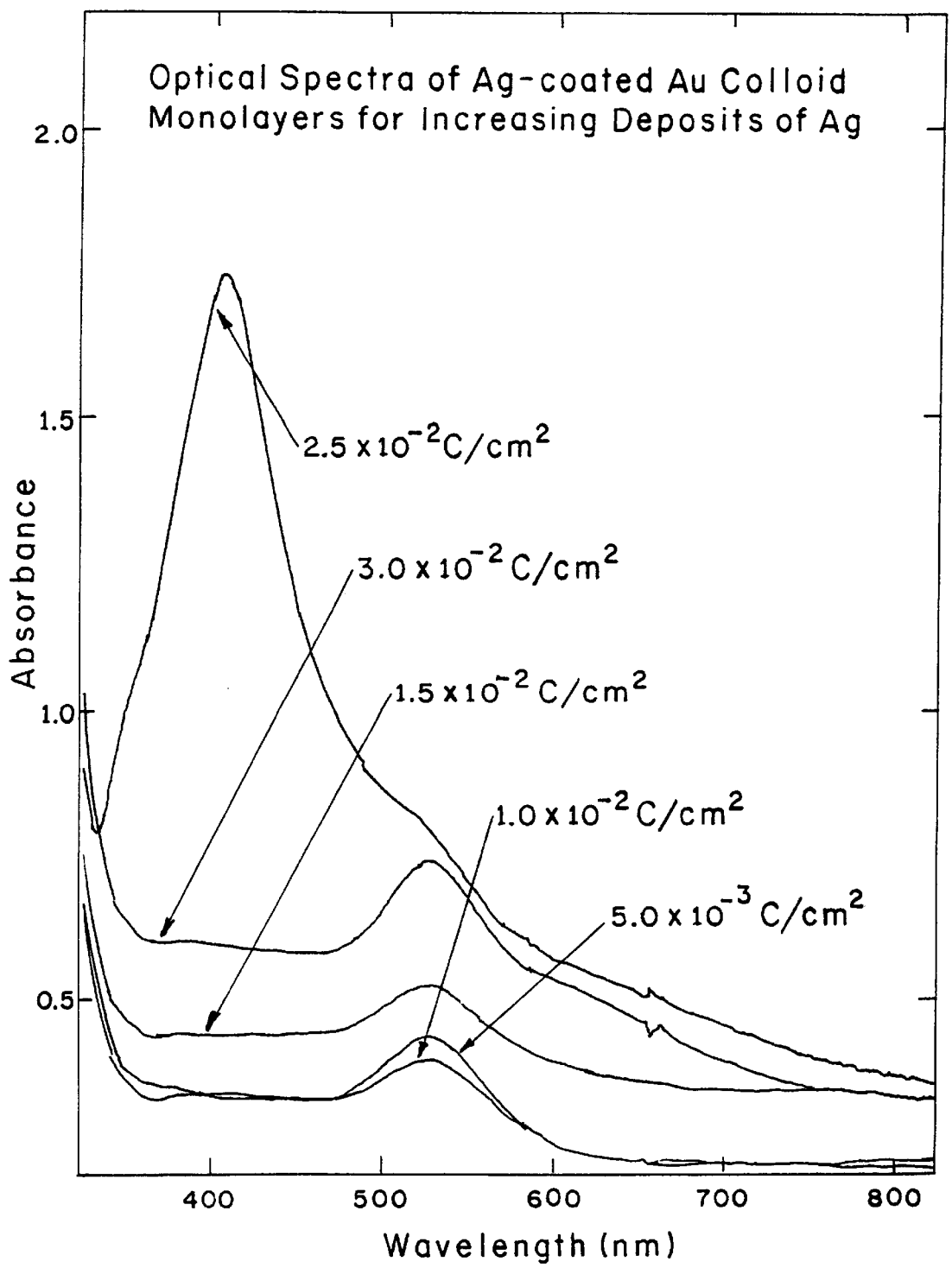
FIG. 22 shows the changes in optical spectra upon electrochemical reduction of $Ag^+$ ions onto Au colloid monolayers in accordance with example 4.
Figure 23:
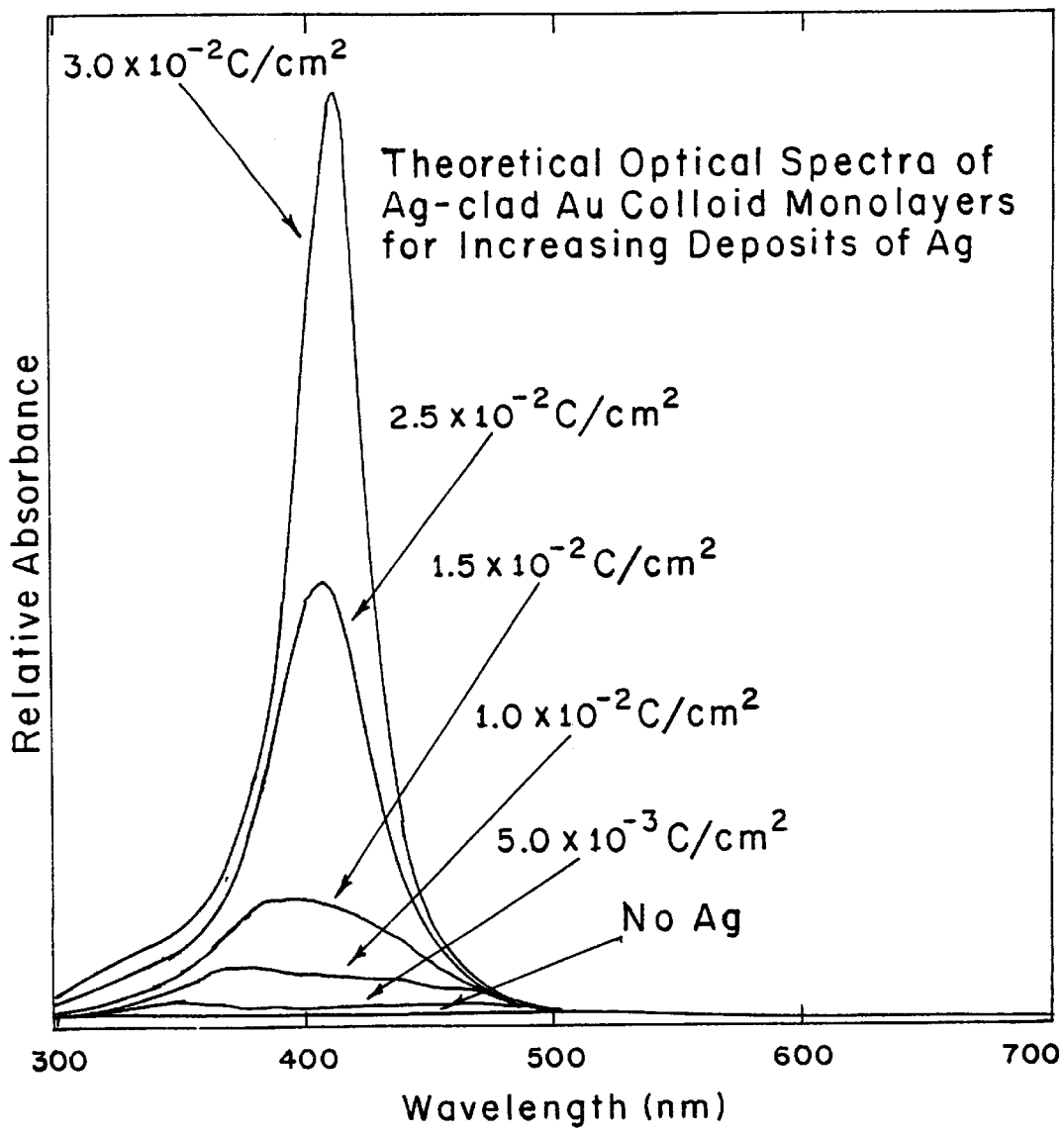
FIG. 23 shows theoretical modeling of the expected change in optical spectra of Ag-clad Au colloid monolayers for increasing deposits of Ag.
Figure 24A:
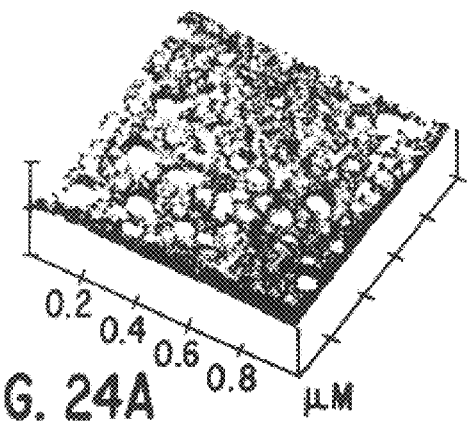
FIG. 24 shows AFM characterization of these surfaces described in example 4.
Figure 24B:
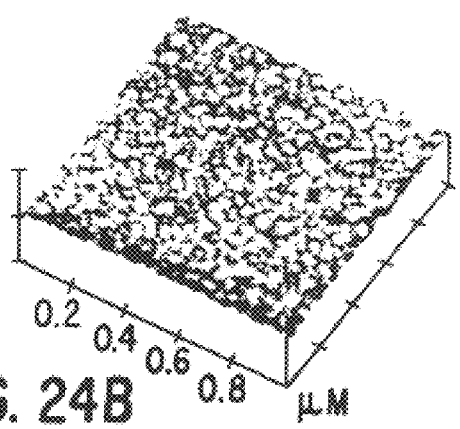
Figure 24D:
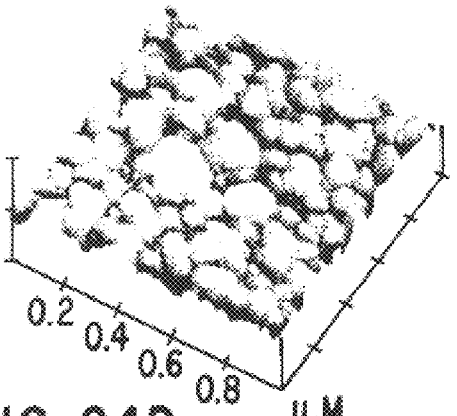
Figure 24C:
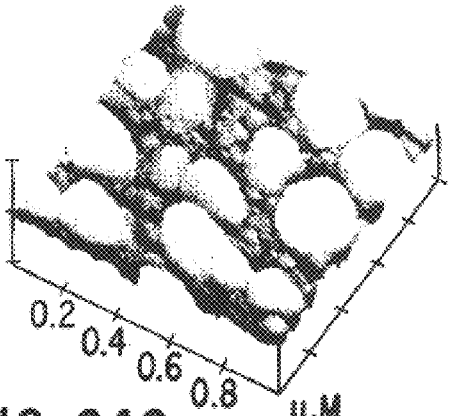
Figure 24E:
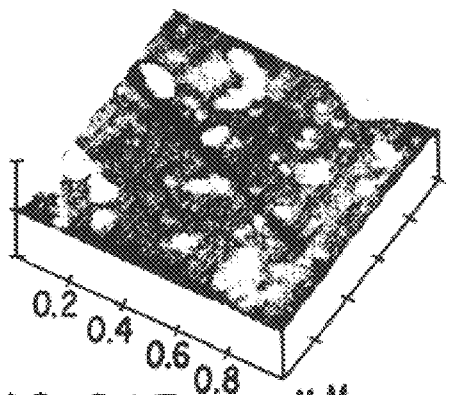
Figure 25:
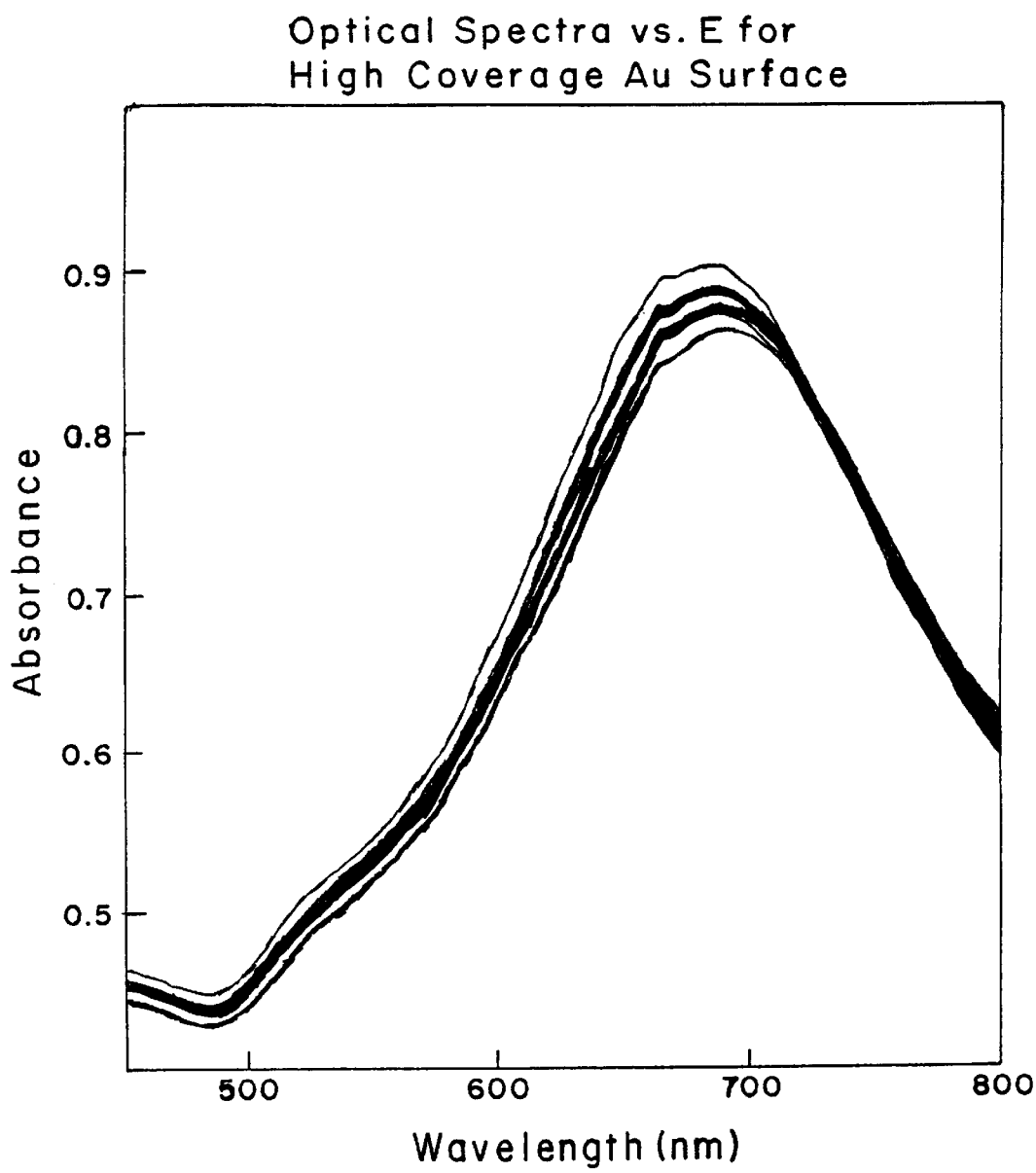
FIG. 25 shows optical spectra as a function of electrochemical potential (E) for a surface with high Au coverage.
Figure 26:
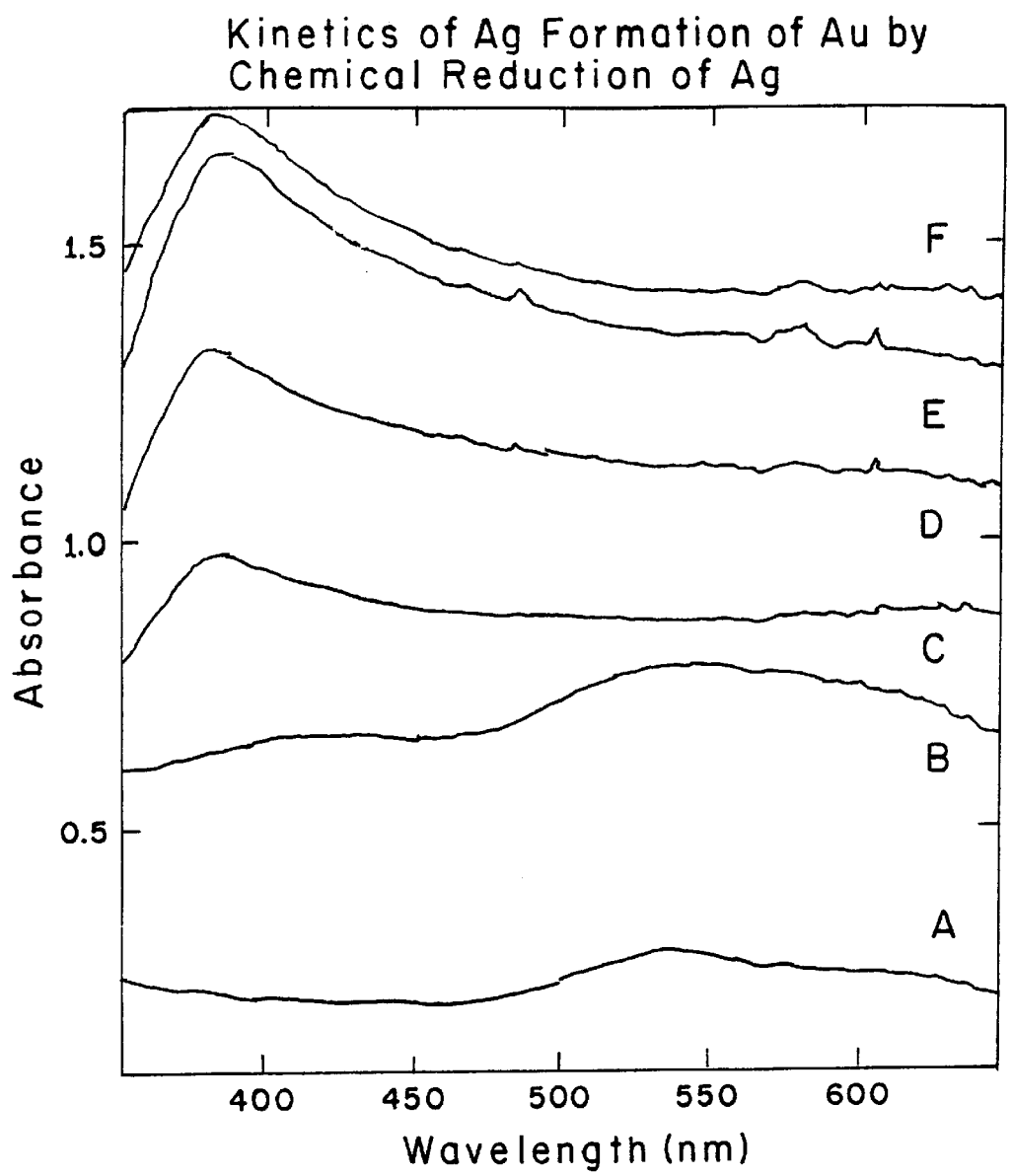
FIG. 26 shows the changes in optical properties accompanying chemical deposition of Ag onto preformed Au colloid monolayers.

FIG. 22 show the changes in optical spectra upon electrochemical reduction of Ag ions onto Au colloid monolayers. FIG. 23 shows theoretical modeling of the expected changes, showing that the Ag is selectively deposited on the Ag surface. FIG. 24 shows AFM characterization of these surfaces. FIG. 25 shows optical spectra as a function of electrochemical potential (E) for a surface with high Au coverage (from 0 to −1 V vs. SCE), showing that these surfaces are stable under electrochemical conditions. FIG. 26 shows the changes in optical properties accompanying chemical deposition of Ag onto preformed Au colloid monolayers.

EXAMPLE 5

Figure 27:
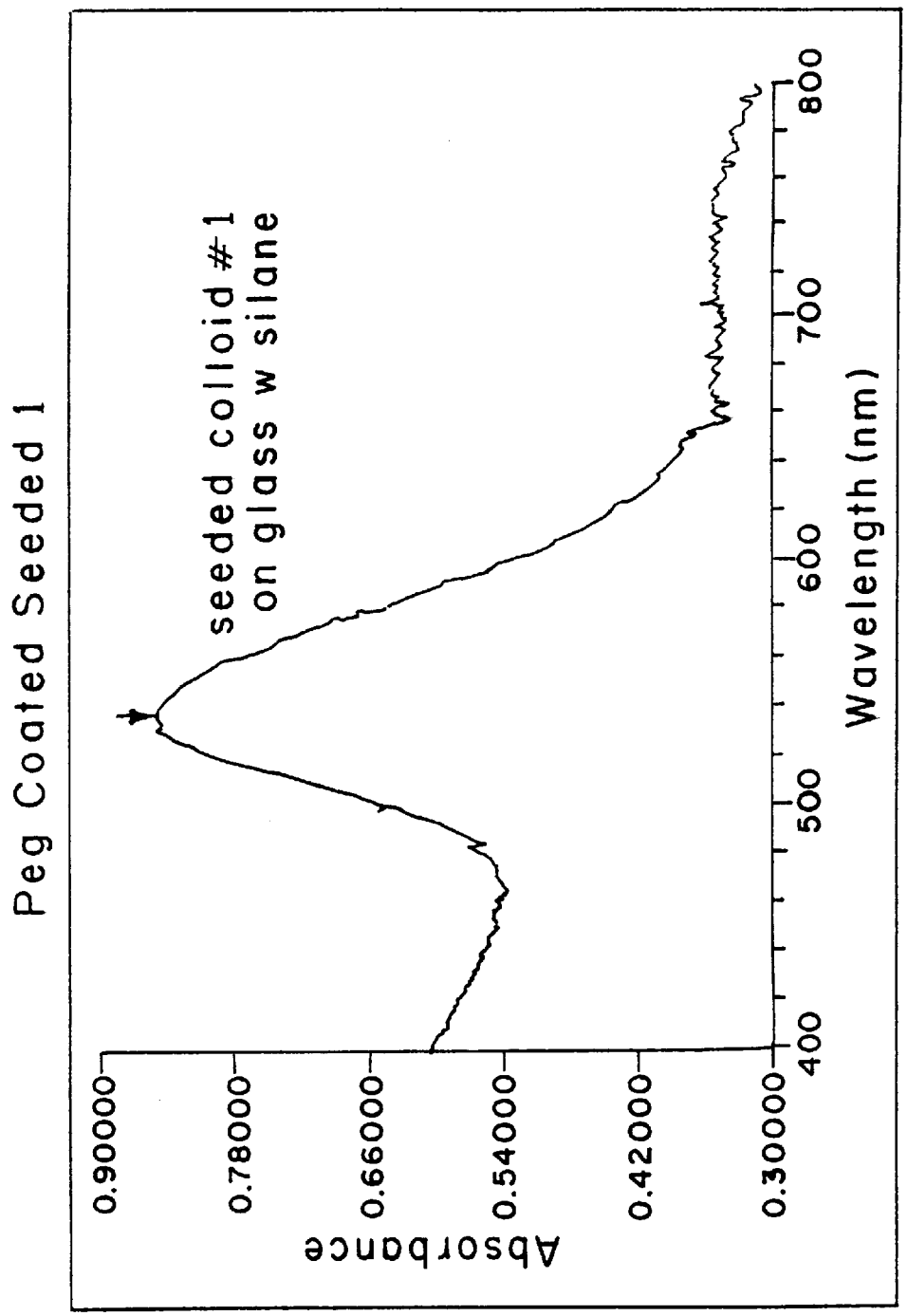
FIG. 27 shows the uv-vis optical properties of a surface coated with colloidal metal particles that were stabilized with PEG.

Large colloids can be stabilized by addition of polyethyleneglycol (PEG). This does not preclude derivatization on surfaces. For example, colloidal solutions were stabilized by the addition of fresh 1% PEG (mw 20,000 Fluka) until the final PEG concentration was 0.1%. The colloidal solution was then centrifuged in glass test tubes at 3000×G for 15 Minutes to pellet the colloid. The supernatant was removed and the colloid was resuspended in distilled $H_2O$. This resuspended colloid was then adsorbed on to silanized surfaces as described elsewhere. The resulting surface was characterized by uv-vis in FIG. 27.

EXAMPLE 6

Preparation of 2.5 nm Au Particles on thin Layers of Inorganic Oxides Coated with Organic Polymers.

Figure 28:
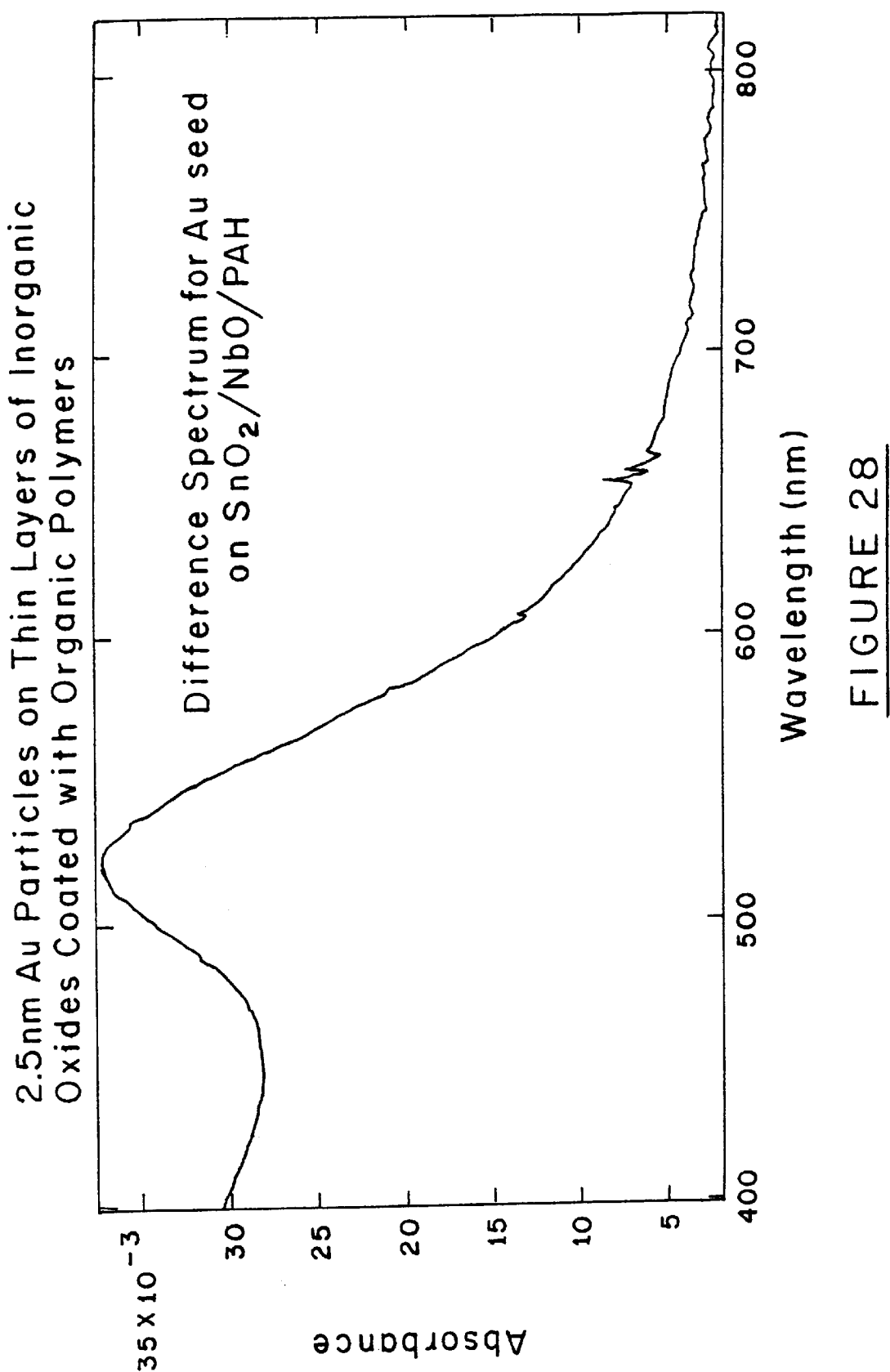
FIG. 28 shows the optical spectrum of a substrate coated with poly(allylamine) hydrochloride and immersed in a solution of colloidal Au.

Indium-doped $SnO_2$, cut to dimensions of 1 cm by 1 cm, was cleaned as follows: surfaces were sonicated for 15 min each in soapy water, 3 changes of triply distilled $H_2O$, and acetone. After the surfaces were rinsed in $H_2O$, they were soaked in 3 M NaOH for 1.5 h. Substrates were stored in $H_2O$ until needed for further derivatization. The $SnO_2$ was derivatized with alternating layers of $K_2Nb_6O_{17}$ and poly (allylamine) hydrochloride (PAH) as decribed elsewhere [Keller et al, JACS, 116, 8817]. PAH-coated surfaces were immersed in a solution of colloidal Au (x nm±y nm) for 28 h. Substrates were then rinsed and stored in $H_2O$. The optical spectrum in FIG. 28 shows the presence of Au particles on the surface.

EXAMPLE 7

Preparation of a 12 nm Au Colloid Monolayer on $SnO_2$ Electrode Preparation

Pyrolytically deposited Sb doped $SnO_2$ (R=100 ohm $cm^2$) on glass 3 mm thick was purchased from Delta Technology Lmtd. The $SnO_2$ on glass was cut into pieces of the size 2 $cm^2$, piranah washed and sonicated in triply distilled $H_2O$ for 15 min. Contact to the $SnO_2$ was made with Ag epoxy. Cu wire encased in 3 mm glass tubing was used as the lead. The Ag epoxy was covered with white epoxi patch (Dexter Corporation). Electrodes were sonocated in triply distilled $H_2O$ for 15 min. prior to use.

Figure 29:
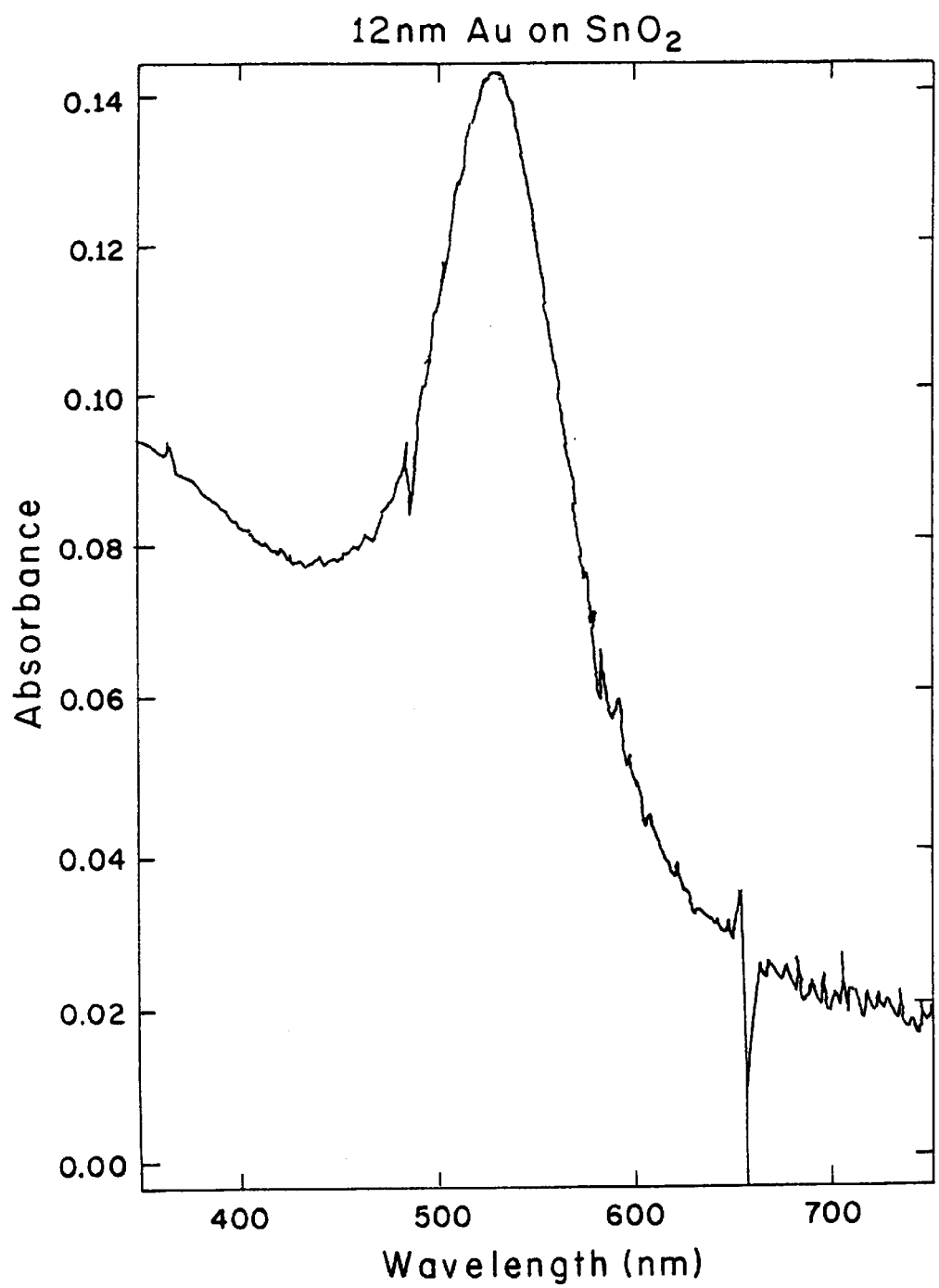
FIG. 29 shows the optical spectrum of a colloid monolayer on $SnO_2$ electrode.

The clean electrodes were placed in 3 M NaOH for five hours, rinsed in $H_2O$, placed in 1% (by weight) aqueous APMDES for 10–15 minutes, and then rinsed with $H_2O$. The electrodes were allowed to dry at room temperature for 2 days. The electrodes were placed in a solution of Au colloid for 3 hours, 20 min., rinsed with $H_2O$, and stored in $H_2O$. An optical spectrum is shown in FIG. 29.

The Au and Ag colloid-based surfaces have many of the best attributes of previously described SERS substrates (uniform particle size, electrochemical addressability, and large enhancement factors), and a combination of other features few surfaces can match (ease of characterization, no geometric constraints, low cost, and very high intra- and inter-sample reproducibility). When the substrate is optically transparent in the visible, uv-vis can be used to assess particle coverage and spacing. These substrates are strongly active for SERS using 647.1 nm excitation, as are those prepared on glass and quartz slides. These advantages, coupled with the ability to vary particle size, spacing, and the nature of the monolayer support suggest a rich use for these materials in fundamental and applied studies. For example, no theoretical model correlating SERS activity with particle size or spacing has ever been quantitatively tested; metal colloid monolayers should allow such experiments to be carried out. The flexibility and control available through this method are noteworthy. Particle size, particle-polymer interactions, and the physical and chemical properties of the underlying substrate can all be manipulated to control the nanoscale architecture produced. The solution-based assembly protocol makes substrate fabrication routine; it also removes virtually all constraints on substrate size/shape. Therefore, Au colloid monolayers can be prepared on substrates that allow facile characterization, including macroscopic glass/quartz slides and TEM grids. Most importantly, SERS can now be considered for applications in which preparation of multiple high-quality substrates was previously viewed as an insurmountable barrier.

Additional Applications of the Inventive Metal Colloid Monolayers

A Method for the Detection and Analysis of a Chemical Compound Dispersed in a Carrier The improved SERS substrates, as described above, enable Raman spectroscopy to be used as a practical method for detecting and analysing carrier-borne chemical compounds, specifically water-borne pesticides, herbicides and other agrochemicals. In addition, they can be used to detect disinfection-generated pollutants in water, such as haloacetic acids. They can also be used to detect, in air, any vapor-phase compounds possessing Raman-active modes, such as explosives, fragrances and the like, in extremely low concentrations.

Background

The widespread use of pesticides in modern agriculture leads inexorably to their appearance in water, and such contamination continues to be an significant threat to water quality. Accordingly, determination of pesticide levels in aqueous samples is a necessary and ubiquitous analytical procedure, and there is an increasing need for rapid, simple, reliable, and pollution-free methods of determining these pesticide levels. Organophosphorous pesticides (OPPs), while not as persistent as other organic compounds used in agriculture, are nevertheless monitored quite carefully, in large part due to their extreme toxicity. Indeed, the National Pesticide Survey (NPS) included 43 different OPPs or OPP degradation products, and left out numerous more because of their instability.

A tremendous amount of published work is concerned with analysis of these compounds, using a compendium of analytical methods. One method previously used relied on the determination of nitrogen/phosphorous (N/P)-containing pesticides in ground water by GC with an N/P detector, using methyl t-butyl ether as the final extraction solvent. For obvious reasons, there is tremendous pressure to reduce or completely eliminate the use of organic solvents in the liquid-liquid extraction (LLE) step. Recently discussed methods for doing so include thin-layer chromatography, gas chromatography (with nitrogen-phosphorous, flame photometric, or mass spectrometric detection), liquid chromatography (with electrochemical, uv diode array, or fluorescence detection), and inhibition of cholinesterase biosensors. In most cases, there is an emphasis on solid-phase extraction (SPE) methods using disks or cartridges, simultaneously eliminating the need for LLE and providing a sample concentration mechanism; in recent reports, the SPE step has been fused to the separation step to yield "on-line" methods. It should be noted, however, that humic acids, clays, and pH have been shown to impact SPE extraction efficiency for several organopesticides. Moreover, several OPPs have been shown to completely degrade on SPE precolumns at 4° C. A reasonable alternative to SPE is accelerated solvent extraction, a technique that reduces the volumes of conventional liquid solvents by the use of increased temperature and pressure.

A second thrust, relevant to the entire field of pesticide analysis, is the recent proliferation of portable instrumentation. The rationale for development of these instruments is the ability to make analytical measurements on-site, a critical component of the emerging national water quality monitoring program. These new instrument and protocols place a premium on "operational simplicity", with the basis of the analytical method typically resting on a single measured parameter, and sometimes even a yes-no response.

A good example of this approach is a recently introduced portable analysis kit for a number of pesticides, including chlorpyrifos, based on a competitive immunoassay, a technique in which labeled and unlabeled analytes compete for binding sites on immobilized antibodies-which in this particular technique are conjugated to magnetic particles. Separation of the magnetic particles, followed by a spectrophotometric assay of an enzyme linked to the labeled analyte [enzyme-linked immunoassay (ELISA)], gives an absorbance proportional to the amount of label. Using a calibration curve, this can be correlated to the concentration of unlabeled analyte in the sample. A similar immunoassay for parathion has also been reported that does not require its removal from hexane.

There are a number of serious drawbacks to these approaches: (i) it is well-recognized that competitive immunoassays are not trivial to carry out, and unlike sandwich immunoassays, in which the signal is proportional to analyte concentration, competitive immunoassays yield signals inversely proportional to analyte concentration; and (ii) different immunoassays kits are necessary for each analyte to be detected; no more than two uv-vis-based ELISAs can be carried out in the same test tube, and multianalyte detection by any method is difficult. Moreover, enzyme labeled analogs and antibodies exist for only a small fraction of OPPs in use. In addition, (iii) the extreme similarity in OPP structure (see Table II) suggests that very high specificity in monoclonal antibodies is not possible, i.e. one OPP could act as an interferant in an assay for another OPP, and (iv) other interferences, which are often present in real-world samples, cannot be identified in single parameter measurements. Finally, (v) even if none of these problems existed, the shelf life and stability of protein-based analytical reagents are generally quite short. The net effect is that while development of immunological approaches to on-site measurements of pesticides is being widely pursued, the measurements must necessarily be carried by people with technical expertise; the possibility of using this method to determine water quality on individual farms by individual farmers, a clear goal of the national water quality monitoring program, is slight.

It would therefore be advantageous to develop a direct method for quantitation of OPPs and other water-borne pestisides or agrochemicals based on surface enhanced Raman scattering (SERS), as this ultrasensitive spectroscopic technique is optimally suited for analysis of dilute aqueous solutions of organic compounds. Like its vibrational counterpart, infrared spectroscopy, Raman spectroscopy yields molecule-specific information relating to the identity of atoms, bond strengths, and bond angles. In other words, a Raman spectrum provides a characteristic fingerprint for a given molecule. Few other spectroscopic techniques can match the high information content of vibrational spectroscopy. This is to be contrasted with methods based on fluorescence and absorbance—immunoassays, for example—in which a single datum is often used to ascertain analyte concentration. Raman spectroscopy has a great advantage over other spectroscopic techniques for analysis of aqueous solutions; $H_2O$ is a very poor Raman scatterer, in contrast to the nearly insurmountable interference $H_2O$ generates in infrared spectroscopy. Raman spectroscopy has not been previously used in the analysis of water-borne pesticides, however, because Raman scattering is inherently a very weak phenomenon, with an intrinsic sensitivity 3–4 orders of magnitude too low to detect OPPs in the submicromolar concentration range. The improved results achieved with the SERS substrates formed in accordance with the present invention enable Raman spectroscopy to be used as a practical method for detecting and analysing water-borne pesticides.

The attraction of Raman spectroscopy as a technique for pesticide detection, and OPP detection in particular, is clearly elaborated in Table I, which lists the strong or medium Raman vibrations between 400 $cm^{-1}$ and 1700 $cm^{-1}$ for 8 OPPs (whose structures are illustrated in Table II). Each of the eight species has a unique spectrum, and each has at least one strong vibration that is spectrally well-resolved from the others. Thus, each compound in this table can be identified directly, without any separation required. In contrast to TLC, GC, and HPLC, this is a direct measurement in the truest sense of the word, since all compounds are detected simultaneously on the basis of their molecular structure. Among the many OPPs available for study, this particular set of compounds was focused on only because SERS spectra already exist: It is stressed that this same technology is applicable to any finite set of OPPs and to other pesticides and other classes of compounds, such as haloacetic acids, the toxic byproducts of chemical disinfection. Table III shows the unique Raman bands for haloacetic acids and chlorinated phenols.

TABLE I

Raman Peak Locations for 8 Organophosphorous Pesticides

| Peak # | A | B | C | D | E | F | G | H |
|---|---|---|---|---|---|---|---|---|
| 1 | | | | | | | ■ | |
| 2 | | ■ | | | | | | |
| 3 | 1628 | | 1628 | 1630 | | | | |
| 4 | | | | | ■ | | | |
| 5 | 1586 | 1588 | | | | 1586 | | |
| 6 | | 1580 | 1580 | | | | | |
| 7 | ■ | | | | | | | |
| 8 | | | ■ | | | | | |
| 9 | | 1249 | 1252 | | | | | |
| 10 | | | | ■ | | | | |
| 11 | | | | | 1231 | | | 1230 |
| 12 | ■ | | | | | | | |
| 13 | ■ | | | | | | | |
| 14 | | | | | | ■ | | |
| 15 | | | | | | | | ■ |
| 16 | | | | | | ■ | | |
| 17 | | | ■ | | | | | |
| 18 | | | | | | | | ■ |
| 19 | | ■ | | | | | | |
| 20 | | | | | | ■ | | |
| 21 | | | | | | | | ■ |
| 22 | | | | | | | | ■ |
| 23 | | | ■ | | | | | |
| 24 | | | | | | ■ | | |
| 25 | | | | | | | | ■ |
| 26 | | | | | | | | ■ |
| 27 | | | | | | ■ | | |

TABLE II

Structures for 8 Organophosphorous Pesticides

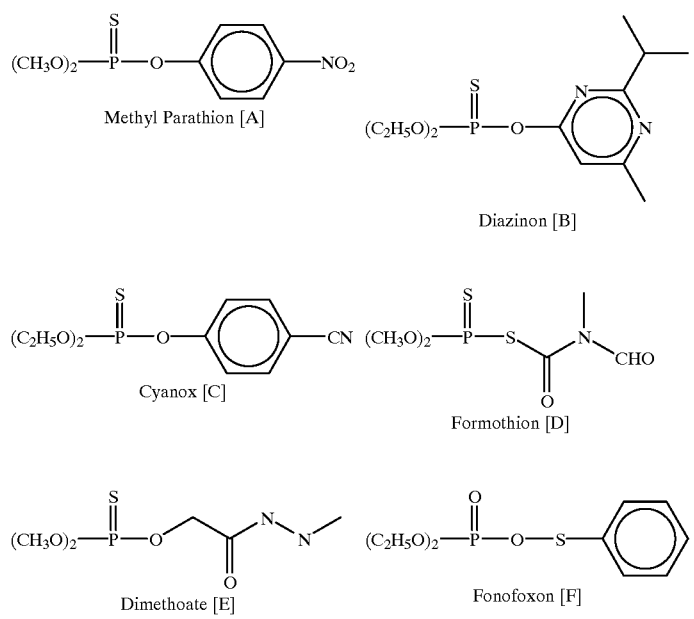

TABLE II-continued

Structures for 8 Organophosphorous Pesticides

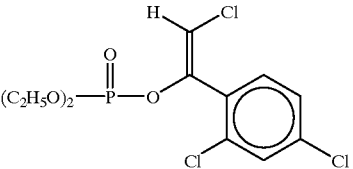

Chlorfenvinphos [G]    Trichlorofon [H]

TABLE III

Raman Spectra of 9 Haloacetic Acids

| | TBAA | DBAA | BAA | TCAA | DCAA | CAA | 2-CP | 24-DCP | 246-TCP |
|---|---|---|---|---|---|---|---|---|---|
| Source | A | B | C | C | C | C | B | B | D |
| Band = 1 | | | | | | | | | 193 vs |
| 2 | | | | 201 s | | | | | |
| 3 | | | | | 217 vs | | | | |
| 4 | 233 vs | | | | | 234 vs | | | 230 vs |
| 5 | | | | | 657 | | 271 vs | | |
| 6 | | | | 280 vs | | | | | |
| 7 | 343 vs | | | | | | | | |
| 8 | | 372 vs | 370 vs | | | | | | |
| 9 | | | | | | | 378 vs | | 379 vs |
| 10 | | | | | | | | 388 vs | 386 s |
| 11 | | | | | | | | 403 s | |
| 12 | | | | | | 412 vs | | | |
| 13 | | | | | 418 vs | | | | |
| 14 | | | | 437 vs | | | | | |
| 15 | | | | 449 vs | | | | | |
| 16 | | | | | | | 489 s | | |
| 17 | | | | | | | 563 vs | | |
| 18 | 614vs | | | | | | | | |
| 19 | | | | | | | | 656 vs | |
| 20 | | 667 vs | | | | | | | |
| 21 | | | | | | 677 vs | | | |
| 22 | 680 vs | | | 684 vs | | | 681 vs | | |
| 23 | | | 727 vs | | | | | 729 vs | |
| 24 | | | | | 775 vs | | | | |
| 25 | 797 vs | | | | | 793 vs | | | |
| 26 | | | | | 821 vs | | | | |
| 27 | | | | | | | 835 vs | | |
| 28 | | | | | | | | 856 vs | |
| 29 | | | | | | | | | 867 vs |
| 30 | | | 906 s | | | 903 s | | | |
| 31 | | | | | 927 vs | | | | |
| 32 | | | | | | | 1031 vs | | |
| 33 | | | 1392 s | | | | | | |
| 34 | | | | | | 1405 s | | | |

Abbreviations:
TBAA = tribromoacetic acid: DBAA = dibromoacetic acid: BAA = bromoacetic acid: TCAA = trichloroacetic acid: DCAA = dichloroacetic acid: CAA = chloroacetic acid: 2-CP = 2-chlorophenol: 2,4-DCP = 2,4-dichlorophenol: 2,4,6-TCP = 2,4,6-trichlorophenol: vs = very strong; s = strong.
Raman data for bromochloroacetic acid are not available.
Darkened boxes refer to vibrations that are spectrally distinct, and whose presence can be used to measure the concentration of a particular HAA in a mixture.
Note that: (a) for some compounds, there are multiple unique bands, each of which could be used as a diagnostic; and (b) there are other, much weaker bands in each spectrum.

It is important to note that a double monochromator and photomultiplier tube detector was used to aquire the data in Table I (in 1987) and Table III (in 1989). The instrumentation available today not only provides greater throughput (with a single monochromator/holographic notch filter combination) but also improved signal/noise (with CCD detectors). Thus, the detection limits for the work proposed herein will be superior to the nanogram levels previously reported.

SERS-based detection has additional advantages relative to HPLC and GC. both of which have significant setup time, involve machinery that is difficult to make portable, and typically require operator training. In other words, these "direct" methods are not necessarily "simple". With pre-formed substrates, SERS data are extremely easy to acquire, comparable to measuring absorbance.

Another significant advantage to Raman spectroscopy over GC and HPLC is the information content per molecule. GC and HPLC techniques identify compounds based on their viscoelastic properties and mobilities, and yield little information: a retention time, or in the case of diode array uv-vis detection for HPLC, an optical spectrum. Unfortunately, these properties cannot always be directly correlated to molecular structure, particularly for compounds with such similar atomic connectivity. Raman spectroscopy offers the advantage of multi-peak identification, with the signal for each OPP having numerous components. In complex matrices, where there is an increased likelihood of interferences and/or impurities, the ability to directly identify a compound using several distinct peaks (Table I) is a huge advantage. This property is especially important for compounds like OPPs that degrade rapidly; characteristic vibrations can be used to identify degradation products, without knowing the degradation chemistry. Similarly, characteristic frequencies can be used to identify other classes of pesticides. In contrast, an unknown compound cannot be identified by GC or HPLC solely on the basis of its retention time. It should be noted that phenylamide pesticides have been quantitated by Resonance Raman scattering in solution, but this requires derivatization with an intensely absorbing azo dye derivatives. Such an approach would not be practical for OPPs, which lack the appropriate chemical functionality.

A final advantage to SERS is that it is an extremely general method; if analyte adsorption can be induced, it can be used for any water analysis without any changes in equipment or configuration. As water quality takes on increased significance in society, and as the number of different compounds in water that must be monitored increases, this is an important consideration.

SERS behavior of colloid monolayers can further be controlled by adjusting the intrinsic properties thereof. It is known, for example, that the dielectric constant of Ag make it more enhancing than Au for visible light excitation. However, over the 10–100 nm scale, Au colloids are more monodisperse than Ag. Thus, in a preferred embodiment of the invention, the strengths of each metal are exploited by using autometallography, a technique whereby $Ag^+$ is selectively reduced onto pre-existing Au particle surfaces. Thus, submonolayers of monodisperse colloidal Au, sufficiently separated so as to be only weakly SERS enhancing, are overcoated with Ag. The resulting particles are larger and therefore exhibit reduced interparticle separation. Particle arrays formed thereof possess Ag-like optical properties and enhancement factors. Testing with Ag-coated Au confirms that the SERS intensity achieved with such particles are within a factor of two of the signal obtained with pure Ag colloid, and within a factor of ten of the best roughened Ag electrodes. These results indicate that these surfaces possess exceptional enhancement characteristics.

While SERS is capable of providing an enormous stream of data, it will be necessary to rapidly convert the data into a usable form. One way to do so is to use artificial neural networks (neural nets) for this task. A growing body of work describes the use of neural nets for spectral recognition, quantitation, or classification. Applications to Mossbauer, laser-induced fluorescence, and mass spectra are notable. A particularly intriguing implementation appears in commercial instrumentation for odor detection.

Neural nets have previously been used in several capacities with regard to pesticide physical properties. These include an estimation of soil partition coefficients based on chemical structure, a model for half-lives, and an assessment of toxicity. More importantly, experiments have been carried out to classify pesticide IR spectra into organophosphorous and non-organophosphorous classes with neural networks. The same group also used a three-layered neural network for automated interpretation of pesticide IR spectra. These results, coupled with demonstrated recent successes of neural networks for multiparameter spectral analysis, indicate that the proposed neural net-based identification and quantitation of OPPs is possible.

Establishment of a non-separation based analytical method on samples containing mixtures requires three stages of experimentation. In the first, detection limits are established for each analyte individually. In the second, detection limits are established for mixtures. Finally, signal calibration is required for mixtures with differing concentrations.

Measurement and optimization of individual detection limits is a straightforward task. The detection limit is defined according to convention as the amount of sample producing a signal/noise ratio of 2. A tremendous advantage of Raman over separation-based methods is the removal of flow-induced limits on integration times. In other words, since the analyte is not moving, one can integrate the Raman spectrum for arbitrarily long times. For CCD detectors, background noise is virtually nonexistent, but practical limitations on integration times are about 15 minutes. Nevertheless, this number should be compared to just the few seconds of integration time available for a chromatographic detector. There are two fundamentally different approaches to measuring SERS spectra of OPPs, each with different detection limits. In Method A, the solution is made basic to insure complete deprotonation of OPPs. A small aliquot (50 $\mu$L) is applied to an Ag/Au colloid monolayer on a substrate of 1.0×1.0 cm dimensions. The hydrophilic nature of these surfaces allows an acceptable degree of wetting; the resulting high surface area/volume ratio leads to rapid evaporation of excess water. Alternatively, the substrate can be mildly heated to promote evaporation. The sample is then placed in front of the laser beam and the SERS spectrum is measured. In Method B, a glass slide containing a colloid monolayer is immersed in the treated $H_2O$, and the SERS spectrum is acquired in situ. Below are estimates for the detection limits for each method.

Method A

Assumptions (1) Detection limit=$10^{-5}$ monolayers of adsorbate (2) Sampling area=focused laser spot size ≈2.0 mm×2.0 mm (3) Molecular area ≈40 $Å^2$/molecule These assumptions are completely reasonable. (1) Single monolayers of adsorbates can be detected by Raman spectroscopy using CCD detectors on unenhanced surfaces. With an enhancement factor of $10^6$, it therefore follows that $10^{-6}$ monolayers can be detected on SERS-active surfaces using a CCD. Thus, a detection limit of $10^{-5}$ monolayers is conservative. (2) Focusing a laser through a microscope objective allows Raman spectra to be obtained from spot sizes approaching 1 $\mu$m in diameter—thus the 4 $mm^2$ sampling area is simple to achieve. (3) The value of 40 $Å^2$/molecule translates to $2.5\times10^{14}$ molecules/$cm^2$, a commonly cited value for monolayer coverage of small adsorbates on surfaces.

Sample Calculation

Let MNDAM=the minimum number of detectable adsorbate molecules=0.00001 monolayers×0.04 cm$^2$ sampled×1 molecule/40 Å$^2$×10$^{16}$ Å$^2$/cm$^2$=1×10$^8$ molecules Only the actual volume above the sampled area is relevant to the detection limit, and this is the sampled area/total area multiplied by the total volume, i.e. (0.04 cm$^2$/1 cm$^2$)×50 μL=2 μL.

The presence of 10$^8$ molecules in a volume of 2 μL corresponds to a concentration of 83 pM. For a species with MW=200 (around the average MW for the 8 OPPs under consideration), this is equivalent to 16.6 ng/L. Assuming all 8 OPPs are present in equal concentration, the detection limit will be increased by a factor of 9. Thus, a simultaneous detection limit of 149 ng/L=0.15 μg/L is anticipated. This number is equivalent to detection limits reported for GC, but without any sample pre-concentration. In other words, direct adsorption to SERS substrates eliminates the need for sample concentration using SPE or liquid-liquid extraction. This is a significant advantage to this method.

Method B

Assumptions

Whereas Method A has the advantage of effectively adsorbing every molecule in a given volume of solution through increased evaporation, in Method B one is constrained by K, the equilibrium constant for adsorption. This parameter defines the surface coverage for a given solution concentration (c). In addition to the assumptions delineated above, the calculation for in situ detection limit will assume Langmuirian adsorption (i.e. no interaction between particles). Thus, q/(1−q)=Kc, where q is fractional surface coverage. In the absence of concrete data regarding attraction or repulsion between particles, it is a reasonable approximation to assume a Langmuirian adsorption isotherm. A value of K=10$^5$ on Ag is likely an underestimate for two reasons: first, OPPs are sparingly soluble, which dramatically increases their affinity for surfaces; and second, most of the compounds in Table II contain sulfer, which binds very strongly to Ag and Au.

Sample Calculation

Using q=10$^{-5}$, c=q/[K(1−q)]=10$^{-5}$/[10$^5$(0.99999)]=1×10$^{-10}$ M. With MW=200, and all 8 OPPs present, this corresponds to 0.18 μg/l, a value similar to that for method A, abut again without the need for pre-concentration.

It is important to note that Method B essentially corresponds to an in situ method, and as such, has important ramifications. A protocol that consists of withdrawing 2 mls of sample, placing it into a uv-vis cuvette, adding a colloid-coated glass slide, and pressing a button on a computer console is exceptionally attractive. If an internal standard is desired (vide infra), this could be added to the cuvette. Furthermore, if the colloid monolayer technology could be transferred to an optical fiber (a likely scenerio, given the success with oxidic surfaces such as glass, quartz, SnO$_2$, and Al$_2$O$_3$), true in situ monitoring can be achieved. Raman spectroscopy using optical fibers is well-established, as is its use to monitor industrial processes; it would be invaluable to monitor speciation of pesticides in real time.

Inherent to the inventive methods are four possible problems: non-systematic intensity variations, the possibility of interferences, the need for adsorption of analyte, and surface saturation-induced nonlinearities in signal. However, each of these can be straightforwardly addressed.

Addition of an internal standard eliminates any concerns regarding surface and/or intensity variation. Any one of hundred of compounds possessing a Raman spectrum distinct from those of the OPPs would suffice. So that adsorption properties would be similar, structural similarity is desirable; thus, fluorinated phenols are a logical choice. Small volumes of known concentrations would be added prior to measurement.

The most likely interferences in SERS are adsorption of inorganic anions (HO$^{31}$, HCOO$^{31}$, etc.) Their influence can be minimized by acidifcation; at pH 5, [HO$^-$]=10$^{-9}$. Thus a simple route to identify (and eliminate) undesired adsorbates is to acquire Raman spectra at several pH's. Halide anions are bound more tightly, but each have only one band in the Raman spectrum, so that their net effect is essentially limited to a reduction of available OPP binding sites. If this leads to significant problems, it can be overcome by introducing an element of molecular selectivity at the Au/Ag interface. The introduction of organothiol self-assembled monolayers (SAMs) onto SERS-active surfaces increases selectivity for the desired analytes, and that partition from solution into the SAM film can be quantitated. A similar strategy can be adopted with regard to the inventive method using HSCH$_2$CH$_2$OH or HSCH$_2$CH$_2$NH$_3^+$. Monolayers of the first molecule should preferentially hydrogen bond with the P=S or P=O functional group relative to H$_2$O, HO$^-$, or halide. Note that direct analyte adsorption is not necessary for SERS: enhancement by the so-called electromagnetic effect—which accounts for 10$^4$ of the 10$^6$ overall enhancement—is still quite substantial 10 Å from the surface.

A legitimate concern is the presence of organic carboxylate impurities. These can be avoided in the preparation of colloid monolayers, but may be present in treated waters (a disadvantage to non-separation based methods). Fortunately, if such compounds are present, they can be easily identified by their Raman spectra. Considering the purity of the waters under consideration, it is anticipated that this will not be a serious problem.

All 8 OPPs will strongly adsorb to Ag, but do not adsorb to equal extents. If two species are present in equal concentration in solution, but one adsorbs with greater affinity, the true concentration of the poorly adsorbed species can easily be masked. Fortunately, the structures of the OPPs fall into two narrowly-defined categories (phosphotriesters and phosphothiotriesters). Within each structural class, the equilibrium constants will vary little. Any non-zero differences between the equilibrium constants for adsorption can be measured and factored in. This process is further described below in the discussion of mixture analysis.

A final potential problem is saturation of the surface-binding sites: at high OPP concentrations, this could lead to a non-linear response. Inaccuracies can be avoided by diluting the original OPP-containing solution by 10–100 when peak intensities exceed 50000 counts per second. If there is no appreciable decrease in signal intensity, the surface is likely saturated. A good procedure for dealing with this is to discard the substrate, dilute by a factor of 500–1000, and repeat the measurement with a new substrate. In general, it is desirable to run each sample at three slightly different concentrations under non-saturating conditions, particularly since the measurement process itself is so simple. This will yield more statistically valid data.

To best understand the complexities of mixtures, the ranges of K for each class of OPP should be determined. Using a microcalorimeter, adsorption isotherms can be generated, from which K can be calculated. With values for K in hand, mixtures are prepared, and the measured intensities compared to those predicted. If they are identical, then by measuring all K's, it is possible to know the exact surface distribution of a prepared mixture a priori. More likely is the case where the predicted and observed differ, in which case it will be necessary to generate calibration curves manually. This requires substantial effort, and can constitute a critical component of the protocol.

Alternatively, the method of standard addition can be used instead of calibration curves. In this approach, known amounts of OPPs are added to samples containing unknown; the x-intercept that results from the linear plot of signal vs. amount added gives the concentration of unknown.

Thus, as described above, surface enhanced Raman scattering (SERS), coupled to a neural net can be used to identify and quantify water-borne pesticides and other compounds, such as haloacetic acids, with detection limits below 0.2 $\mu g/L$. This can be accomplished without the need for extraction or separation. This method makes use of Au, or preferably Ag-clad Au colloid monolayers, used in combination with SERS instrumentation. In contrast to existing methods, the method of the invention is remarkably simple to carry out, and provides direct spectral identification for each compound. The inventive technique can be used alone, or interfaced to existing separation methods. Further, the inventive method makes on site detection of water-borne pesticides possible.

Colloid Monolayer-Based Detection In Separation Experiments

SERS can also be used as a detection method in a separation experiment. A default protocol would thus be to do GC or HPLC with SPE, adsorbing the eluate directly onto colloid monolayers. Using a micromanipulator to raster the surface across the solvent exit port will thus preserve the chromatogram spatially on the SERS substrate, which can then be addressed in a site-by-site fashion by SERS. For HPLC, this is a technically trivial task. The task is slightly more complex for GC; nevertheless, a SERS-based GC detector has been described. In any case, coupling HPLC or GC with SERS eliminates any problems mixtures engender, while considerably improving the detection limits currently available for each.

Figure 30A:
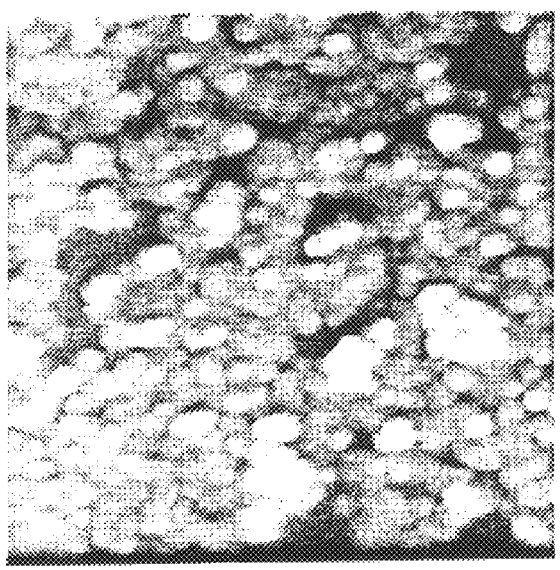
Figure 30B:
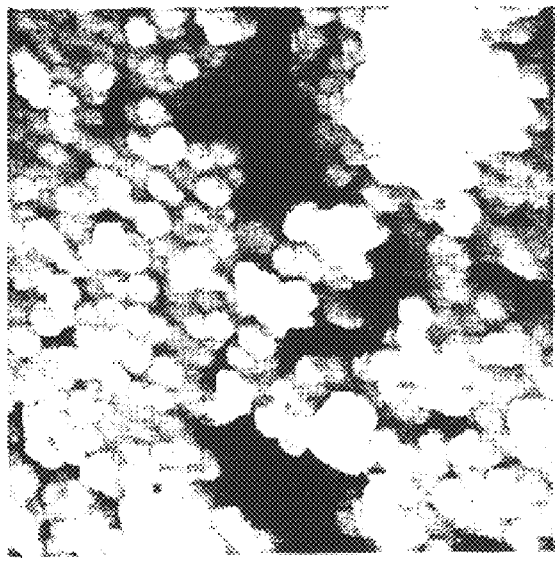
Figure 30C:
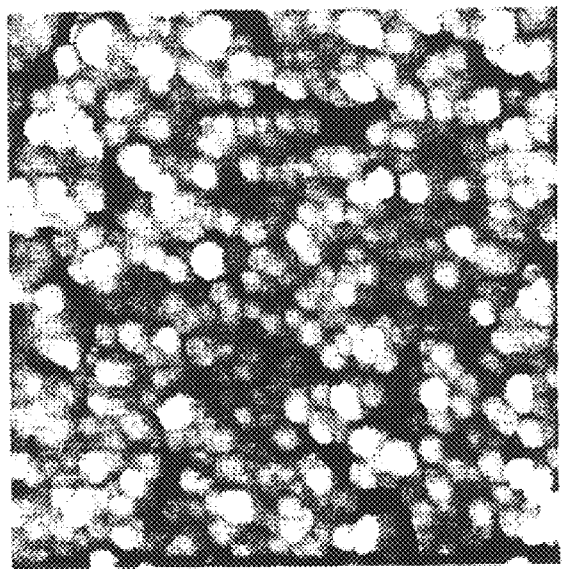

SERS can also be used in conjunction with capillary electrophoresis (CE). The basic idea behind SERS detection in CE is to spread the eluate onto an Au or Ag (or Ag-coated Au colloid monolayer on conducting $SnO_2$ and then interrogate the surface using microRaman. FIG. 30 illustrates this approach. An electric field is applied between one solvent reservoir and a conductive substrate, such as a doped $SnO_2$ surface. Alternatively, the tip of the capillary can be metallized, and the electric field applied thereto, in which case a non-conductive substrate can be used. One end of the capillary is placed in the solvent reservoir, and the other end is contacted to the Au colloid monolayer. The substrate is then rastered by the capillary. As compounds A, B, and C elute, they are deposited at different spots on the surface. Elimination of diffusion and forced adsorption can be simultaneously effected by solvent removal, and MPMDMS (mercaptopropylmethyldimethoxysilane)-based Au colloid surfaces can be heated to 70° C. with no effects on optical or SERS behavior. Once immobilized, the substrate is rastered across a focused laser and the spectra are recorded using a CCD. Like recently-popularized direct uv fluorescence detection schemes for CE, no pre- or post-column derivatization is needed. However, this method is not restricted to uv fluorophores and works for all Raman-active molecules.

It has previously been demonstrated that a capillary can be rastered while in operation and that Au and Ag colloid monolayers have a high degree of reproducibility from area to area and within a given sample. Therefore, several runs can be carried out on a given substrate. Alternatively, the sample can be discarded and another used—the value of the Au on a microscope-slide sized substrate is a fraction of one cent. In other words, these substrates are disposable. SERS has previously been demonstrated using a microRaman apparatus with attomole mass sensitivity, and detector sensitivity has improved considerably since then.

A possible pitfall in the device shown in FIG. 30 is the presence of non-uniform fields on the colloid monolayer surface, resulting in analyte migration. If this occurs, it can be circumvented in two ways. The simplest approach is to make electrical contact to both ends of the $SnO_2$ substrate, eliminating any potential drops across the surface. Another alternative is to metallize the outer surface of the capillary end and make contact to it.

A conservative estimate of the detection limit can be calculated using a 5 $\mu m \times 5$ $\mu m$ spot size and a SERS signal/noise (S/N) ratio of 1000:1. Raman microprobes allow focusing down to spot sizes down to 1 $\mu m \times 1$ $\rho m$, and with the CCD detector now available, a S/N of >5000:1 is attainable. With a monolayer coverage of $10^{14}$ molecules/$cm^2$, one calculates 25 $\mu m^2 \times 10^{14}$ molecules/$cm^2 \times 1 cm^2 / 10^8$ $\mu m^2 = 25 \times 10^6$ molecules in the laser beam for a full monolayer. Factoring in a detection limit where S/N=2, this corresponds to 50,000 molecules.

Surface-Confined Protein/Au Complexes and the Use Thereof as Biosensors

Studies indicate a future trend in the medical field will lead to an increased use of implantable "biochips", responding to biosensor analysis of health-related biological markers via controlled release of surface-confined drugs. Before such technology can be practically used, however, dramatic advances are needed in biosensor architecture: the distinct fabrication chemistries and different readouts (photons, current, frequency, etc.) of the present devices preclude integration into miniature, multi-sensor arrays. What is lacking is a uniform mechanism for transducing a ligand binding event or a solution concentration into a measurable quantity. In view of this need, as well as for the need to replace immunoassays with more rapid methods, Applicants have developed a series of biosensors based on complexes between biomolecules and colloidal Au nanoparticles. It has been found that appropriately sized colloidal Au nanoparticles can be used as non-denaturing photon and electron "antennae" for biomolecules, allowing biomolecule/Au colloid conjugates to be used as building blocks for a variety of sensing mechanisms. More specifically, this aspect of the invention is directed to biomolecule/Au complexes that can be used to detect biological ligands (either small molecules or proteins) through measuring of binding-induced changes in electrical resistance, using the previously described self-assembled metal colloid layers.

Discontinuous conductors surrounded by insulators are an imporant class of materials that include evaporated thin metal films and particle-loaded polymers. At low conductor concentrations (p), these materials do not conduct electricity; at high p, conductivity approaches bulk values. At a certain critical concentration ($p_c$, the percolation threshold), dramatic increases in ac and dc conductivity are observed. In this threshold region, small changes in insulator volume (which decrease conductor concentration) lead to large changes in film resistance. Accordingly, small molecules that induce swelling in polymers can be detected by measuring the resistance changes in polymer/conducting particle composites. Similarly, volume changes in percolating Au/antibody films, induced by antigen:antibody complex formation can be detected by simple resistance measurements which can then be converted to analyte concentration data. Related implementations include detection of receptors using arrays of Au particles harboring surface-confined ligand, and detection of oligonucleotides using surface-confined complementary fragments.

As was previously noted, Au colloid-based macroscopic surfaces are simple and inexpensive to prepare, stable, amenable to assembly in large numbers and in any geometry, extremely reproducible, capable of further modification (i.e. Ag deposition to yield Ag-clad Au), SERS-active, and electrochemically addressable. Further, surface confined protein/Au complexes retain bioactivity, a property of the utmost importance for potential sensor applications.

An important feature of the Au colloid-based substrates is the control of feature size, spacing, and substrate coupling available through self-assembly. Size control is simple, as descibed above. Since solution-based surface formation is based on particle diffusion, manipulation of interparticle spacing can be achieved through a detailed understanding of the kinetics of surface evolution. In addition, tremendous variation in coupling between colloidal submonolayers and the underlying substrates is available through modulation of the spacer film thickness.

These parameters are crucial in determining how metal surfaces interact with proteins. Numerous studies using a variety of spectroscopic techniques have shown that direct protein adsorption on macroscopic metal surfaces leads to partial or complete denaturation. The most likely, process for this denaturation is through formation of thermodynamically favorable protein-surface contacts that lead to reduced conformational flexibility and, eventually, to unfolding. The denaturing properties of macroscopic metal surfaces pose a serious problem for biosensors, which typically require metals to transduce biological signals.

It has been found that, unlike macroscopic metal surfaces, small colloidal Au particles do not denature proteins as the high curvature of the nanoparticles minimizes the surface area available to the proteins. In fact, colloidal Au particles of $\leq 5$ nm in diameter are the same size as the proteins themselves. In contrast, the diminished curvature of larger particles leads to approximately the same characteristics noted with macroscopic Au surfaces, and thus, it is generally accepted that larger Au particles, as well as aggregates of smaller Au particles, have an increased tendency to denature proteins.

The surface confined protein/Au complexes can be formed by exposing the surface of a previously formed Au colloidal monolayer to protein. Alternatively, a pre-formed protein/Au complex can be immobilized from solution onto a substrate. The latter method is preferable as it allows the particle:protein ratio and the biological activity to be ascertained prior to immobilization. The ability to prepare macroscopic, bioactive metal interfaces of well defined structure is the key step to a uniform biosensor architecture, and when coated with protein receptors, or antibodies, such surfaces form the basis for a novel type of biosensor based on ligand binding-induced conductivity changes.

While ligand-induced changes in the dielectric constant of protein films have been proposed as a sensing mechanism, and changes in solution conductivity are routinely used to measure cell growth, the use of biopolymers as molecule-sensitive insulators in composites with metal particles has not been previously suggested. Such technology was heretofore unavailable as only Au nanoparticles combine the high degrees of conductivity and biocompatibility needed for operation of this type of biosensor, and until the present discovery of a self-assembled colloidal Au monolayer, there was no mechanism for the preparation of macroscopic, well-defined two or three dimensional particle-based films having the degree of coverage required for conductivity. The two dimensional particle based films display a p≈0.16. The inventive method, however, allows the interparticle spacing to be decreased (by, for example, coating the Au particles with Ag) to such a degree that a p of about 0.60 is achieved. Alternatively, multilayers with p≈0.4 to 0.6 can be formed. In the three dimensional regime, these are conductive.

The varying of particle spacing has been found to have a profound impact on the electronic and electrochemical properties of surface-confined colloidal Au films. For example, in measuring the sheet resistivity (measured by the four-point probe method) of a 12-nm diameter colloidal Au film on glass as a function of absorbance at 520 nm, in which increased absorbances (which correspond to decreased spacing) were effected by repetitive exposure of the Au colloid-derivatized surfaces to $HOCH_2CH_2SH$ and colloidal Au in solution led to an abrupt five order of magnitude drop in resistivity as the absorbance increased from 0.4 to 0.6. Because this absorbance range corresponds to relatively close packed monolayers (as opposed to multiple layers), the data demonstrates that sensitive resistance measurements on monolayers of protein/Au complexes can be performed. Further, the insulator-conductor transition is extremely sharp compared to those obtained with vapor-deposited thin Au films, demonstrating that protein/Au complexes assembled to the percolation threshold are extremely sensitive to volume changes.

The colloidal Au monolayers described above have the properties of a two dimensional system, surrounded by air. Because three dimensional composites of conductive particles and insulating polymers display a much lower Pc, the use of Au colloid multilayers is prefered to a monolayer arrangement. Therefore, there is described below a method for the stepwise assembly of conducting Au colloid multilayers from solution.

When a Au colloid monolayer on 3-aminopropyltrimethoxysilane (APTMS)-coated glass is exposed to a molecule having two functional groups that bind to or induce flocculation of colloidal Au {2-mercaptoethanol, 2-mercaptoethylamine, $HS(CH_2)_6SH$, APTMS, polyvinylpyrrolidone, etc.}, immersion in colloidal Au leads to additional particle binding. Repetitive dips (5–15 minutes for the crosslinker, 5–60 minutes for the colloid) into bifunctional organic crosslinker and colloidal Au solutions (with copious rinsing between immersions) rapidly leads to formation of Au colloid multilayers. Note that no interlayer registry of particles is expected. This method is very general, and can be used with colloidal Au nanoparticles of any diameter, although the lower particle concentrations for standard preparations of both large and small particles lead to longer derivatization times.

Figure 31:
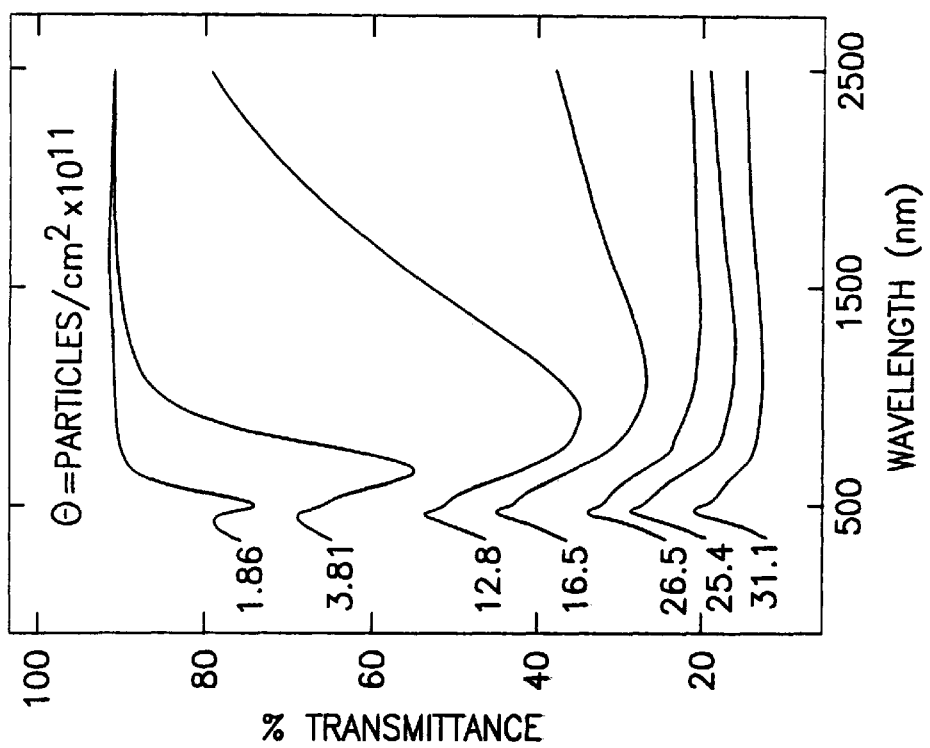
FIG. 31 shows Au particle coverage dependence (in particles/cm$^2$) of uv-vis/near-IR transmission spectra of Au colloid multilayers (prepared by successive, repeated immersion of a glass slide derivatized with APTMS and a 12-nm diameter Au colloid monolayer into (a) 4 mM 2-mercaptoethanol and (b) 17 nM, 12 nm-diameter Au)

Tapping-mode atomic force microscopy (AFM) has been used to monitor the growth of colloidal Au films. Images obtained after 2 and 5 exposures to 2-mercaptoethanol/ colloidal Au indicate a porous geometry,with neither close-packed coverage within a layer (in accord with previous findings) nor registry between layers (FIG. 31). Importantly, these AFM images clearly indicate large areas of uninterrupted particle contact after just two 2-mercaptoethanol/Au treatments, suggesting the possibility of conductive paths.

Figure 32:
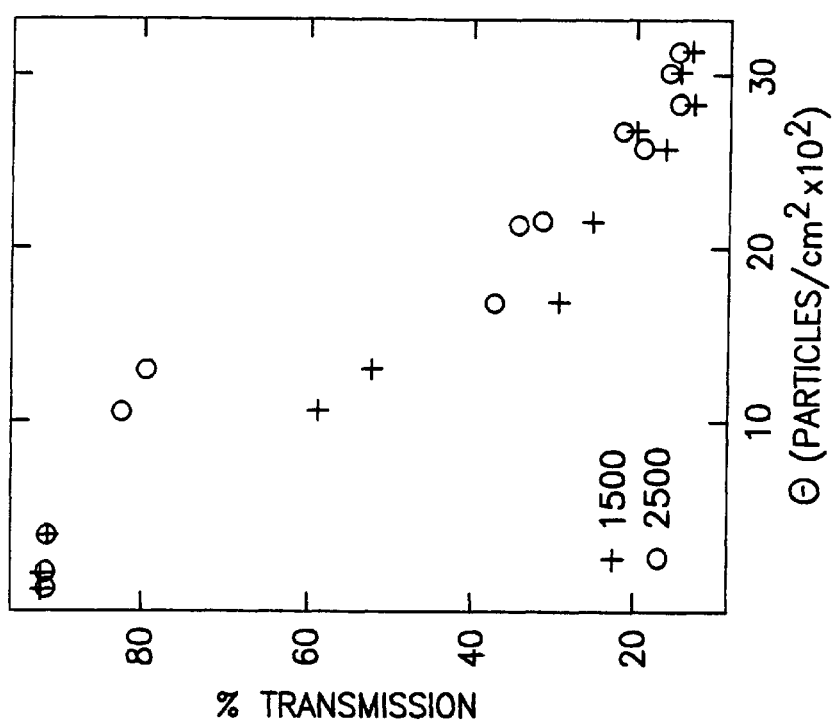
FIG. 32 show the percent transmission at 1500 nm (+) and 2500 nm (O) as a function of Au colloid coverage for a Au colloid multilayer. These data were obtained from FIG. 1 of the manuscript.

Further support for metal-like attributes comes from visible/near-infrared optical transmission spectra as function of particle coverage for samples immersed between 1–12 times in 2-mercaptoethanol/12-nm Au. The spectra for low coverages match those previously obtained for 2-D Au arrays or small Au aggregates in solution: strongly absorbing in the visible and transparent in the near-infrared (FIG. 32). As the particle coverage increases, near-infrared transmission decreases markedly and becomes only weakly wavelength dependent. Similar behavior is seen in evaporated thin Au films, which also exhibit linear plots of transmittance vs. p at 1500 nm or 2500 nm. The intersection point of these lines (i.e. the point at which % T is wavelength-independent) corresponds to $p_c$. In Au colloid multilayers, a similar plot shows no such intersection (FIG. 33).

Figure 34:
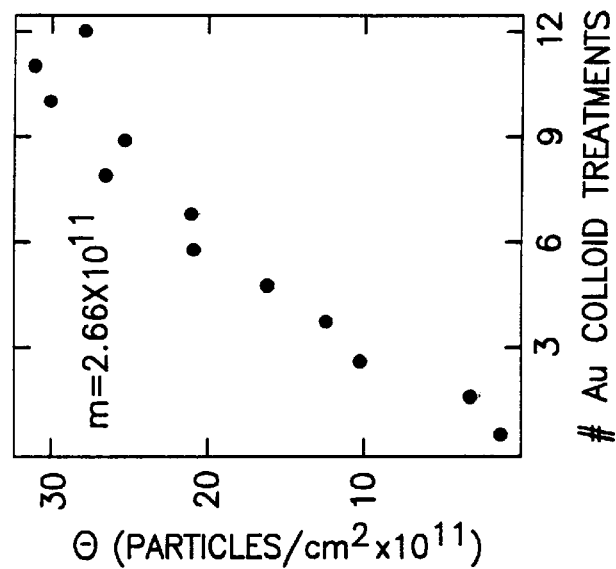
FIG. 34 shows Au particle coverage (in particles/cm$^2$) vs. the number of immersions into 12-nm colloidal Au in which one immersion corresponds to a monolayer.

Nevertheless, at sufficiently high coverages, Au colloid multilayers undergo an insulator-conductor transition. A plot of DC resistance (plotted on a log scale) vs. particle coverage shows that samples containing $15 \times 10^{11}$ particles/cm$^2$ are insulating, with a resistance approaching $10^8 \Omega$. Increasing particle coverage leads to an enormous decrease in resistance; when the particle coverage is doubled to $30 \times 10^{11}$/cm$^2$, the resistance drops below 100$\Omega$, a change of almost 6 orders of magnitude (FIG. 34). Considering the extremely porous nature of these films, and the presence of organic adsorbed 2-mercaptoethanol on the particles, these films are remarkably conductive: the most conductive sample (12 treatments) has a resistivity of $5.1 \times 10^{-4}$ $\Omega$-cm, a value roughly 1/200 that of pure Au of the same geometry. Au colloid multilayers on glass substrates are thus more conductive than In-doped SnO$_2$, for example, and can be used for routine voltammetric measurements. Electron transfer between particles likely occurs by activated hopping between nearest neighbors, as previously observed for granular metal films.

Figure 33:
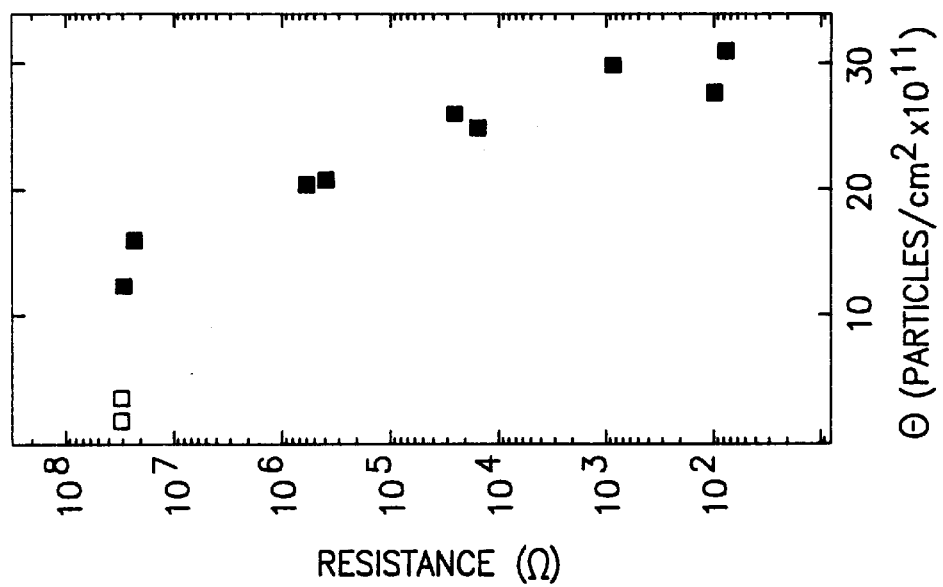
FIG. 33 shows a log plot of DC resistance versus Au particle coverage for Au colloid multilayers. See FIG. 29 for details of sample preparation.
Figure 35:
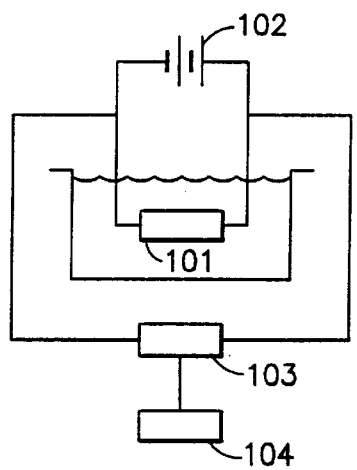
FIG. 35 shows a diagram of a device for determining the presence of an antigen protein.

Interestingly, the Au volume fraction does not change with increasing particle coverage, evidenced by a linear plot of coverage vs. number of immersions in Au (FIG. 33). In other words, each step in the multilayer assembly adds the same amount of Au; the slope of the line ($2.66 \times 10^{11}$/cm) corresponds to p=0.38. This value is below that needed for 2-D percolation, but sufficient for 3-D percolation, suggesting that the dramatic decrease in resistance results from establishment of multiple 3-D percolation paths.

Figure 36:
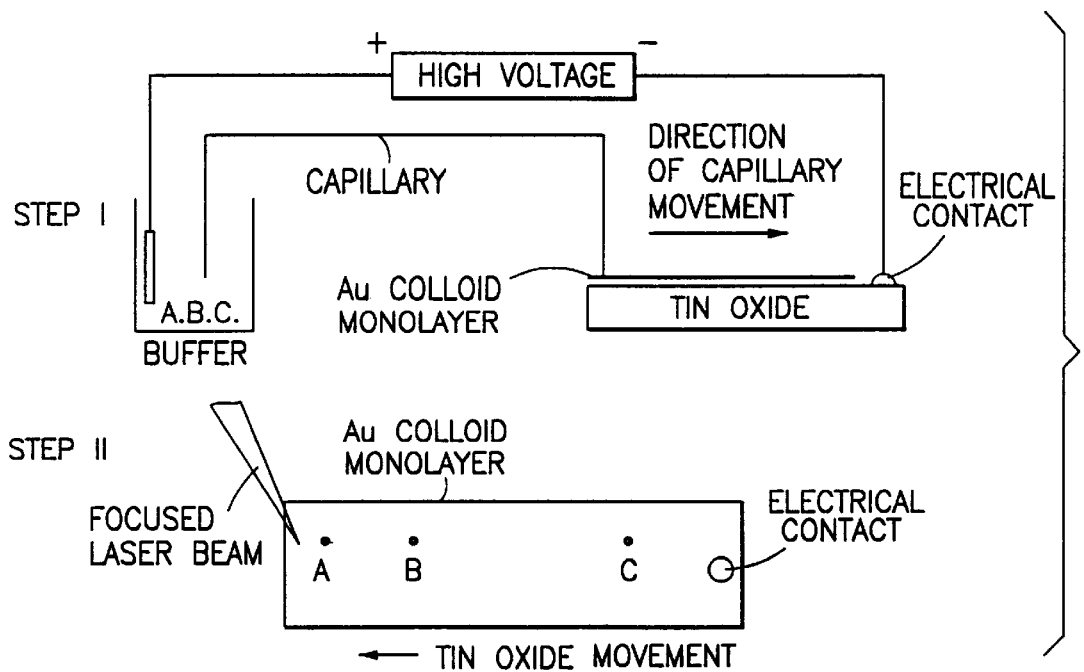
FIG. 36 shows the coupling of a colloid-based SERS with capillary electrophoresis.

Devices for determining the presence and/or concentration of a biomolecule, with a biosensor comprising a receptor, antibody, or biocomplement-coated Au colloidal layer can be constructed in the same manner as devices using the conventional discontinuous conductor in insulator-based sensors. As shown in FIG. 36, such a device could include, for example, the inventive biosensor 101, means for applying a voltage across the biosensor 102, means for measuring an electrical characteristric (e.g. resistance) of the biosensor 103 and means for converting resitivity data to analyte (antigen) concentration 104. An alternative, but equally viable implementation of the device shown in FIG. 36 involves measurement in air. The present technology is not limited to any specific class of biomolecules and is applicable to biosensors for detecting any biomolecule for which there is a corresponding binding partner.

Binding of a colloidal Au particle monolayer to a preformed Au colloid monolayer or multilayer changes the effective film thickness, a fact that can be used to fabricate a biosensor based on changes in surface plasmon resonance (SPR) signals.

To wit, a Au colloid monolayer or mulitlayer of insufficient thickness to achieve resonance (at a given excitation wavelength/angle of incidence) is coated with an antibody. This surface is then exposed to analyte (antigen). After rinsing, the sample is exposed to a Au colloid: antibody complex (the same antibody as bound to the surface). Binding of the Au:antibody to the surface-bound antigen leads to an increase in Au film thickness leading to resonance. Thus, in contrast to a conventional SPR method, which measures small, binding event-induced changes in reflectivity of a thin Au film under resonant plasmon excitation, the binding event described above leads to an enormous increase in reflectivity. This novel approach has several advantages. First, the "sandwich" immunoassay approach is widely used in immunochemical analytes, including enzyme-linked immunoassays (ELISAs). Thus, there is little doubt that chemistry described above will obtain. Second, this approach can be used to sense small molecules, not routinely possible with current SPR technology. Third, the sensing chemistry is general for any analyte B in an A-B-C ternary complex. For example, A and C can be non-complementary strands of DNA attached to surface-bound and solution phase DNA, and B can be an oligonucleotide (to be sensed) with ends that are complementary to A and C.

Optimization of the Surface Characteristics of the Metal Colloid Monolayer

Preferably, for any specific application of the metal colloid monolayers, the surface characteristics, i.e., Au particle coverage (density), Au particle size, Ag cladding thickness, will be optimized. To determine the optimal surface characteristics, a solution-based combinatorial strategy for synthesis of surfaces exhibiting nanometer-scale variation in mixed-metal composition and architecture has been developed. With this method, continuous or stepped gradients in the size and number density of surface features can be generated simultaneously on different regions of a single substrate. In order to demonstrate this technique, the surface enhanced Raman scattering (SERS) response of a glass slide upon which the coverage of colloidal Au and the extent of Ag coating were varied and optimized. Over a 2 cm×2 cm sample area, changes in enhancement factor (EF) spanning four orders of magnitude were realized, and the changes in nanostructure responsible for these effects were determined using atomic force microscopy (AFM). The results show significant changes in SERS EFs over small alterations in surface morphology, demonstrating the power of solution-based combinatorial approaches for optimizing the characteristics of mixed-metal materials.

Figure 37:
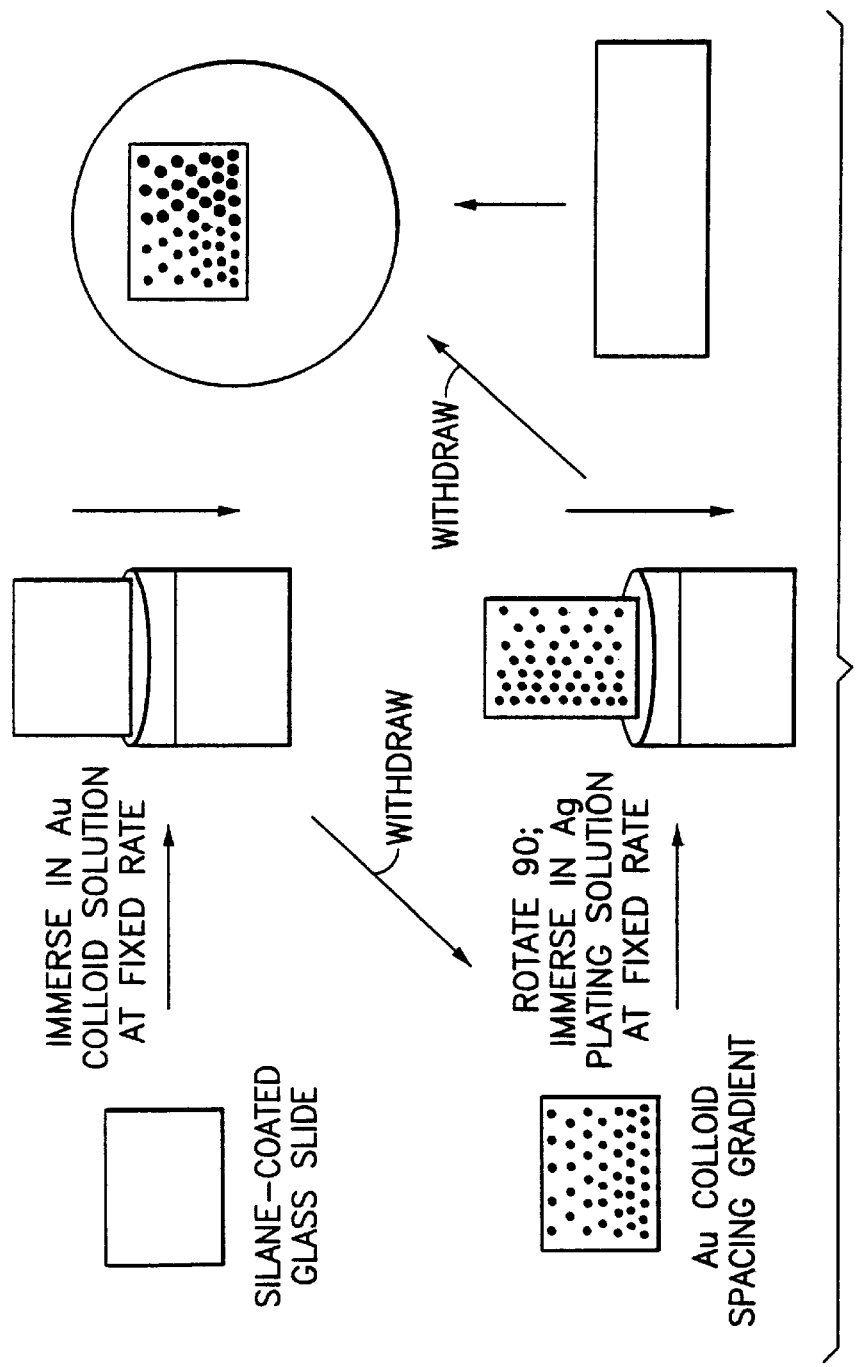
FIG. 37 illustrates a technique for forming a self-assembled metal colloid monolayer that exhibits continuous nanometer-scale gradient of mixed-metal compositionand surface architecture. Such gradients are useful for optimizing surface characteristics of the metal colloid monolayer for a given application.
Figure 38:
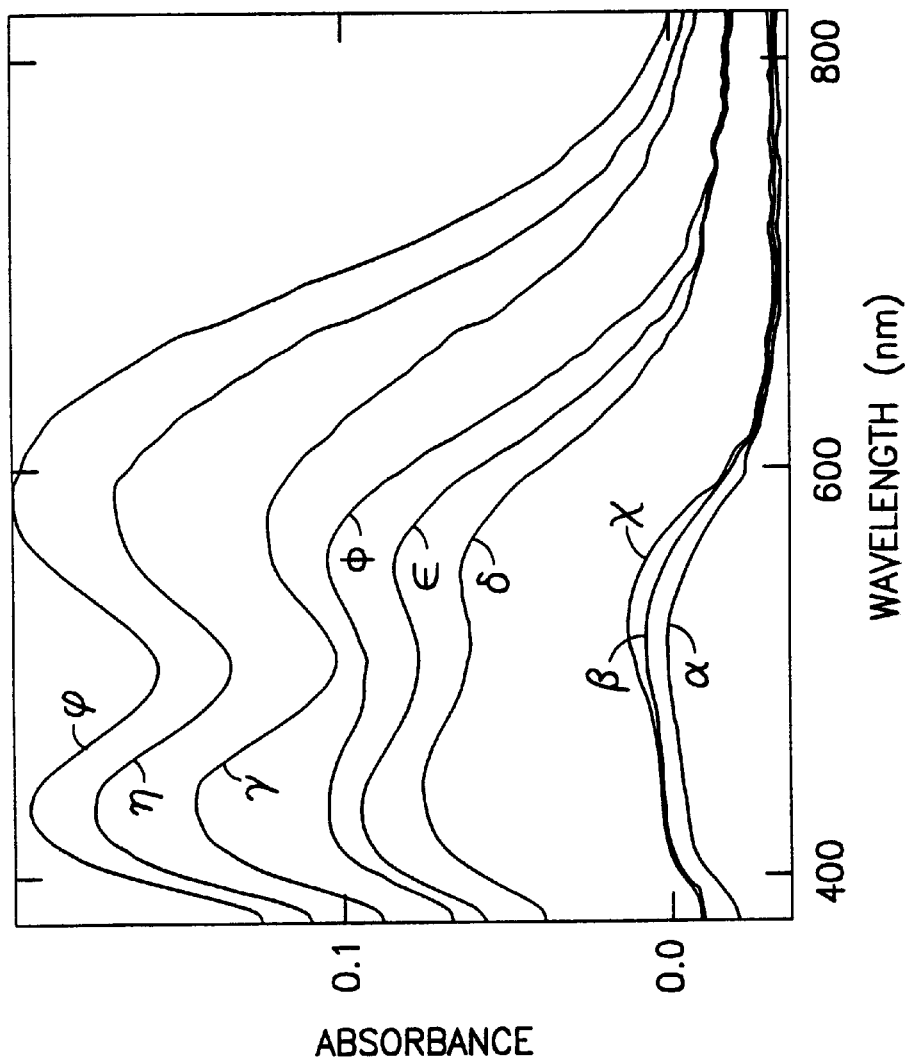
FIG. 38 shows UV-vis waves of 9 different Au/Ag coatings of a stepwise gradient combinatorial surface. The sample was submerged into Au in 3 steps of 0.83 cm, with 50 minute pauses, turned 90°, and lowered into an Ag$^+$ solution in 3 steps of 0.67 cm, with 10 minute pauses resulting in a maximum Au exposure time of 2.5 hrs, and Ag exposure time of 30 min. Au and Ag exposure times for spectrum ω are analogous to the exposures for the morphology represented by AFM image C in FIG. 42.

The general combinatorial assembly approach is shown in FIG. 37. The number of colloidal Au particles bound to functionalized surfaces can be predicted from immersion times in colloidal solution using initial (time)$^{1/2}$ kinetics. Thus, when a 3-mercaptopropyltrimethoxysilane (MPTMS)-coated glass slide attached to a motorized translation stage is immersed at a fixed rate into a 17 nM aqueous solution of 12-nm diameter colloidal Au, a gradient in particle coverage is generated in the direction of immersion. After sample rotation by 90°, fixed-rate immersion into a Ag$^+$-containing solution designed to specifically deposit Ag on Au leads to a gradient in particle size over the new immersion direction. The resulting surface exhibits a continuous variation in nanometer scale morphology as defined by particle coverage and particle size that results from known, repeatable immersion conditions. In preparing the gradient surface, a stepper motor with a 2° step yields a 3 $\mu$m translation. Over a 3 cm×3 cm region, it is therefore possible to generate $10^8$ different, 9 $\mu$m$^2$ nanostructures. Macroscopic regions with uniform morphology can be prepared by very rapid successive steps followed by a long delay. These stepwise gradients are especially useful in examination of bulk changes in physical properties. For example, optical changes linked to growth of the characteristic Ag plasmon band at 400 nm with increasing Ag coverage, evident to some degree in continuous gradient samples, are clearly visible as square regions with uniform shading. FIG. 38 shows optical spectra of 9 different Au/Ag coatings, showing evolution of the Ag plasmon mode.

Figure 39:
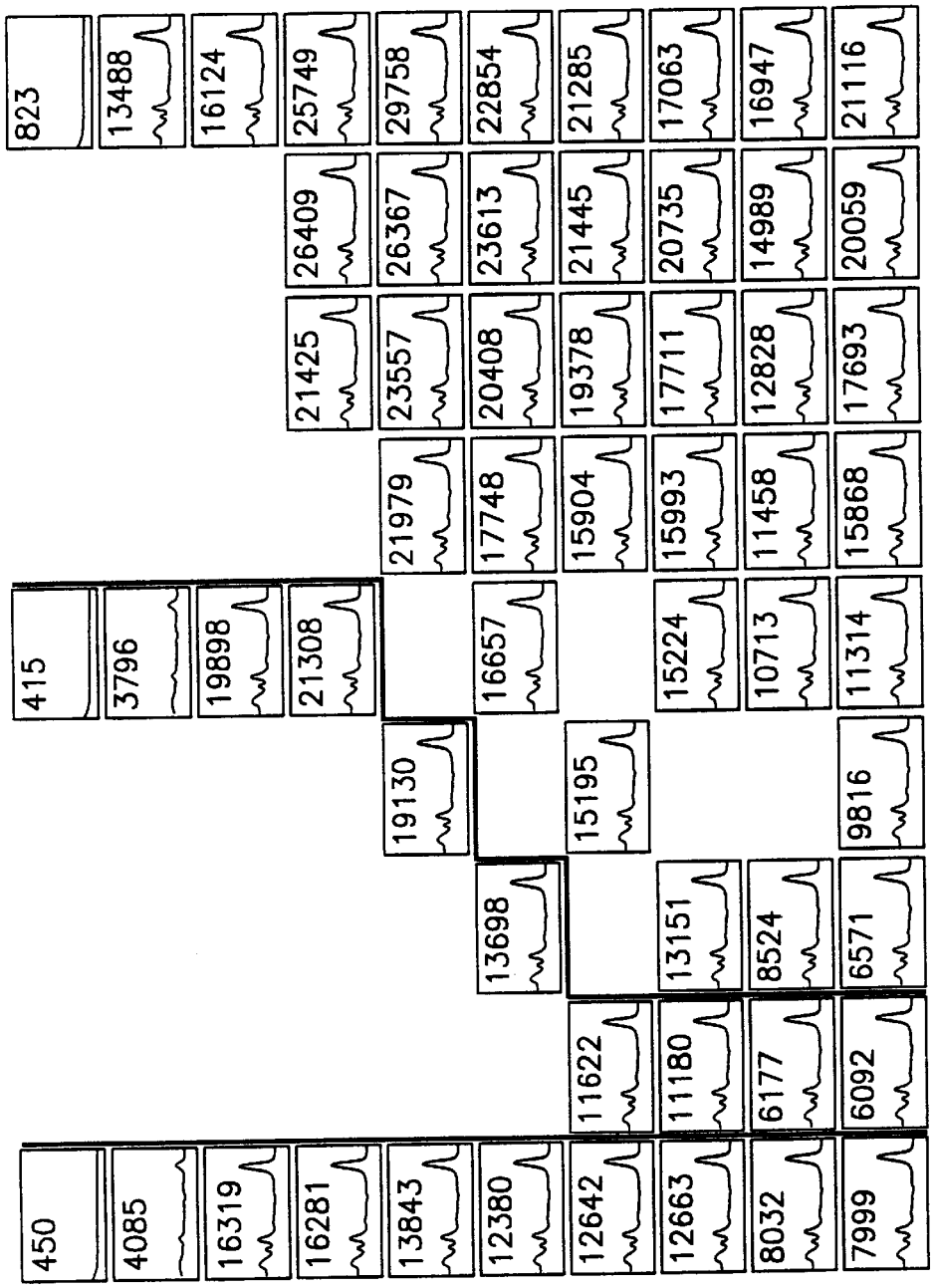
FIG. 39 shows SERS response of spatially discrete areas on a 2.5 cm×2.0 cm continuous gradient combinatorial surface (4 hrs for Au, and 20 minutes for Ag, respectively). Each box represents a SERS spectrum collected in a 0.2 cm×0.2 cm area on the sample; each spectrum's x-axis is Raman shift (1300 cm$^{-1}$ to 1650 cm$^{-1}$) and y-axis is intensity (0 counts per second (cps) to 35000 cps). The numbers located in each box indicate the background subtracted intensity of the 1610 cm$^{-1}$ ring stretch mode of p-NDMA, and box locations in space correspond to the acquisition position on the sample; bold vertical lines indicate a 0.2 cm jump in position. Particle coverage increases from left to right, and particle size increases from top to bottom. Experimental conditions; [p-NDMA]=0.3 mM, 20 mW of 530.9 nm excitation, 1 cm$^{-1}$ step, 1-s integration, 5 cm$^{-1}$ band pass.
Figure 40:
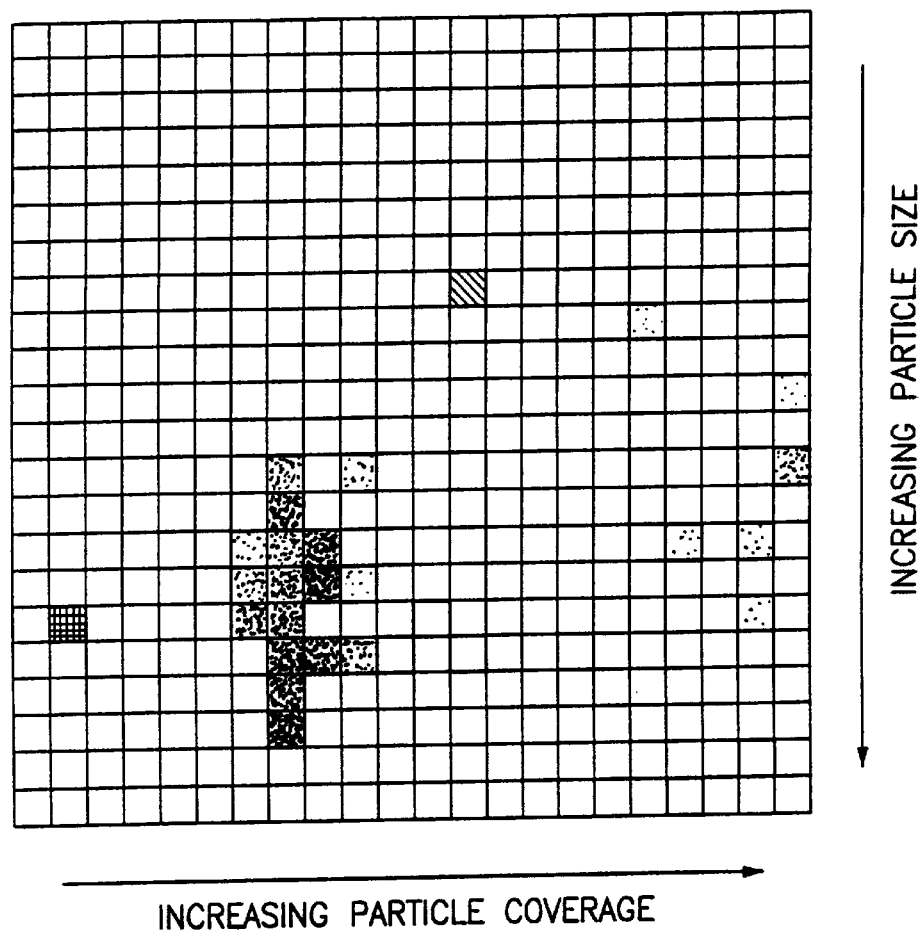
FIG. 40 shows background subtracted SERS intensity map in counts per second (cps) for the 1610 cm$^{-1}$ symmetric ring stretch of p-NDMA on a large scale continuous gradient combinatorial surface, 0–12 hr for Au, 0–30 min for Ag. Each box represents one SERS spectrum in a 0.1 cm×0.1 cm area, total sample size is 2 cm×2 cm. Experimental conditions; [p-NDMA]=2.5 mM, 25 mW of 647.1 nm photons focused at the sample; 1 cm$^{-1}$ step, 1 s integration, 5 cm$^{-1}$ band pass.

To demonstrate the SERS screening approach, the SERS response on spatially discrete areas of a 2.5×2.0 cm continuous gradient substrate were determined; the results are shown in FIG. 39. The data clearly show regions where the SERS intensity was maximized. A second example in FIG. 40 shows similar data plotted in a different way. Here, increasing SERS intensity is denoted by increasing depth of shading on a grid, with the most intense spectra corresponding to the darkest squares.

Figure 41:
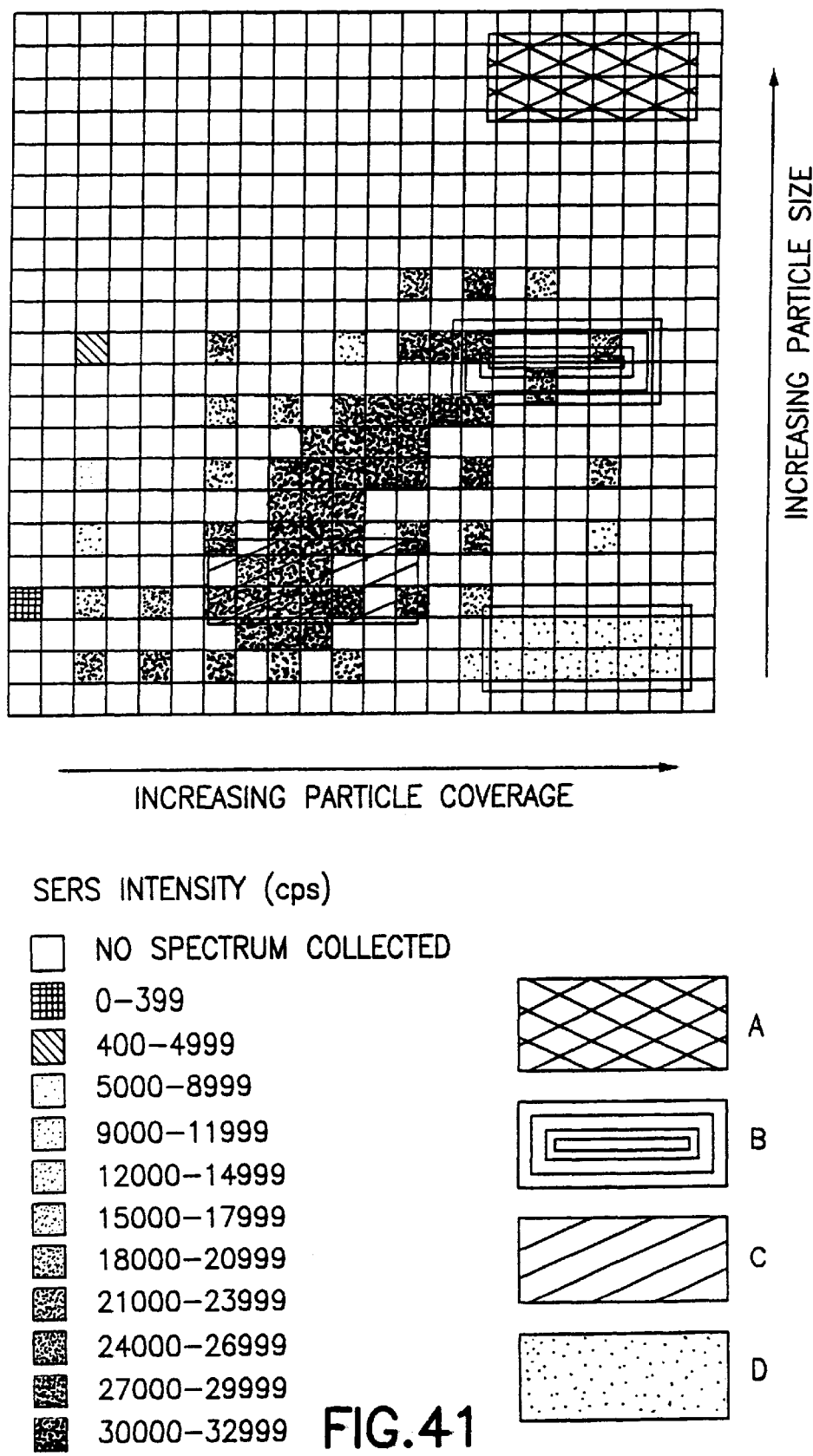
FIG. 41 shows background subtracted SERS intensity in counts per second (cps) for the 1168 cm$^{-1}$ phenyl-nitroso stretch of p-NDMA as a function of sample position. Each shaded box represents one SERS spectrum collected in a 0.1 cm×0.1 cm area. Regions A–D correspond to AFM images in FIG. 39. Experimental conditions: [p-NDMA]=2.5 mM; 30 mW of 647.1 nm, 2 mm diameter spot at the sample; 1 cm$^{-1}$ step, 1 s integration, 5 cm$^{-1}$ band pass.
Figure 42A:
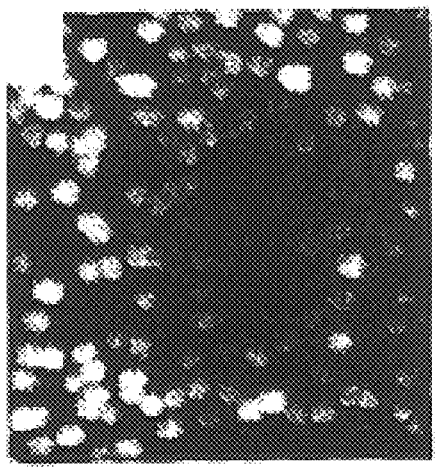
FIG. 42 shows AFM images (500 nm×500 nm) of MPTMS-derivatized glass slides with varying coverages of 12-nm diameter colloidal Au and varying quantities of deposited Ag. Images A–D correspond to regions delineated in FIG. 38. Z-axis (vertical) gray scale: black=0 nm, white=35 nm.
Figure 42B:
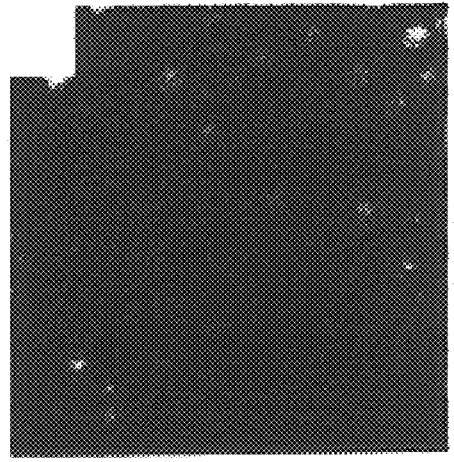
Figure 42C:
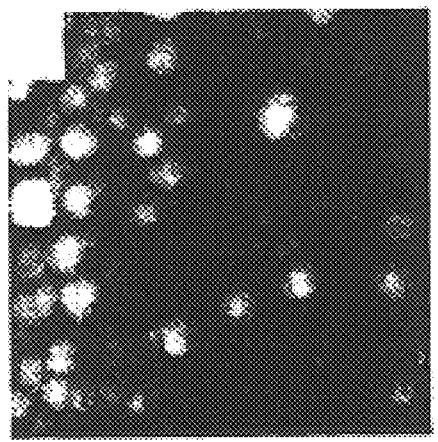
Figure 42D:
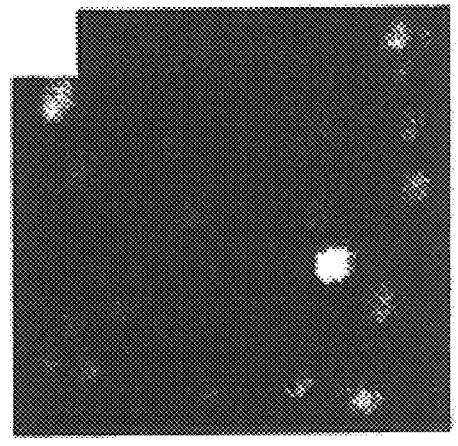

An example of combinatorial signal optimization was determined as follows. SERS signal for adsorbed p-nitrosodimethylaniline (p-NDMA) was measured over a 2 cm×2 cm sample exhibiting continuous gradients in Au coverage and Ag cladding thickness. The immersion times for sample preparation (0–6 hr for the Au gradient, 8–22 min for the Ag gradient) were established by determination of the most enhancing region from an initial, large gradient SERS screen on a 2 cm×2 cm sample (0–12 hr for Au, 0–30 min for Ag). FIG. 41 shows a spatial map of the background-corrected SERS intensity for the phenyl-nitroso stretch at 1168 cm$^{-1}$. Intensity trends from 15 initial spots at 0.4 cm intervals were used to locate the most SERS-active area on the sample. Further interrogation at smaller intervals revealed a region that was at least $10^4$-fold more enhancing than the least SERS-active domains of the substrate. The location of this region, a narrow diagonal band of moderate Au particle coverage and Ag coating, is surprising, suggesting that maximum EFs are obtained at relatively fixed interparticle spacing. Such spacing can be achieved either by a thin coat of Ag on closely-spaced Au particles, or with larger Ag coatings on particles exhibiting slightly larger spacing.

AFM was used to determine the nanometer-scale morphology at positions of interest (FIG. 42). In FIG. 42, the image labels A–D correspond to representative morphologies at locations marked by shaded squares in FIG. 41. Sampling positions were chosen to highlight variation in Ag cladding thickness (i.e. to span the vertical gradient) as opposed to variation in number density of particles. Accordingly, differences in particle coverage in images A, B and D are not significant, and represent positional uncertainty in the horizontal (coverage) gradient. Immersion time in Ag$^+$ increases in the order D>C>B>A (A=0 min Ag), but SERS intensity follows the pattern C>B>D>A. Section analyses reveal that mean particle size increases from A to C as expected, but decreases in D. Two related effects contribute to this result; the formation of small Ag particles between Ag clad Au colloids, and the loss of monolayer structure (i.e. formation of multilayers) upon extended Ag exposure. Evidently, interconnection of closely-spaced particles to yield surfaces with a morphology resembling roughened electrodes has a deleterious effect on SERS.

The wavelength dependence of the SERS intensity is shown in FIG. 43. The data show that the highest SERS enhancement factors were obtained using 647-nm excitation, even though the $v^4$ Raman effect favors a lower excitation wavelength. Using this wavelength, the nanostructure was optimized over two iterations, as shown in FIGS. 44A and 44B. These figures show position-dependent SERS intensity maps. The results of the first map were used to optimize the maximum signal in the second map. FIG. 44C is a SERS intensity map generated using 28-nm diameter Au nanoparticles. FIG. 44C shows that the use of the larger core particles leads to an increase in overall signal, as evidenced by the different intensity scales.

Figure 45:
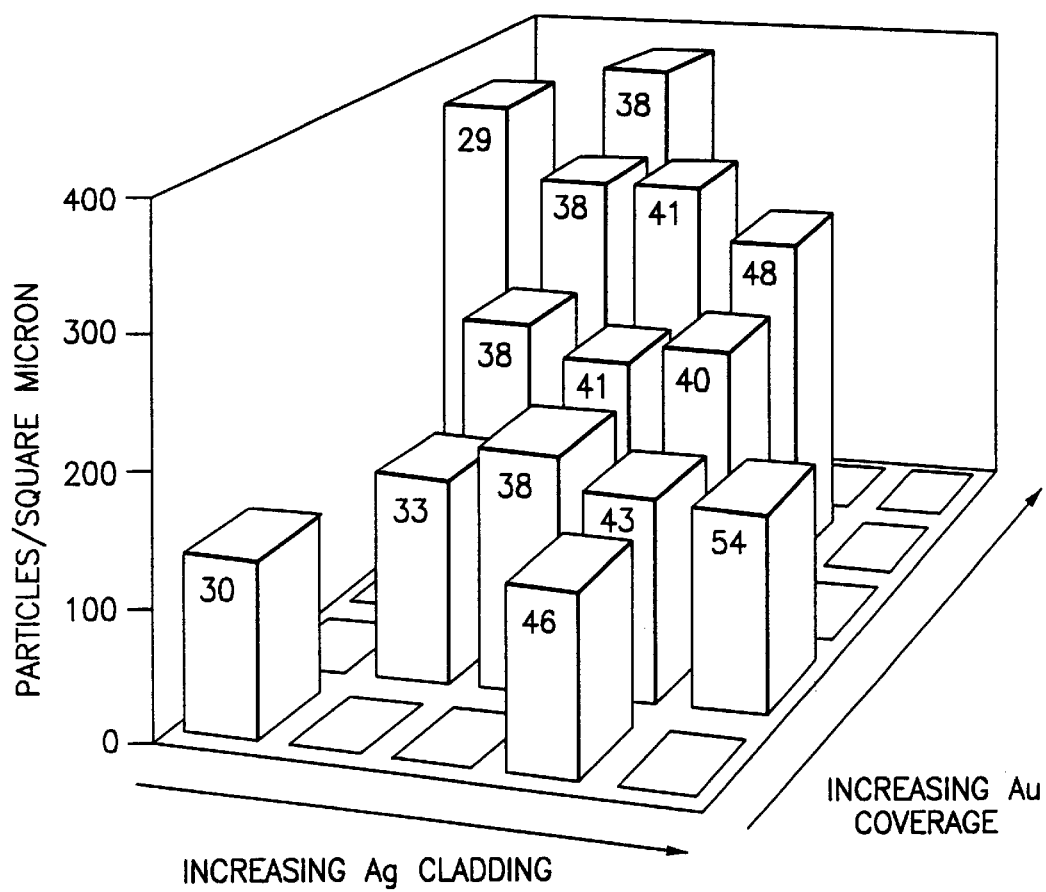
FIG. 45 is a bar graph showing the number of particles per square micron as derived from analysis of AFM images (Au colloid/MPMDMS/glass). Numbers on the bars represent the mean particle height (in nm) for the images as obtained via a section analysis.
Figure 46A:
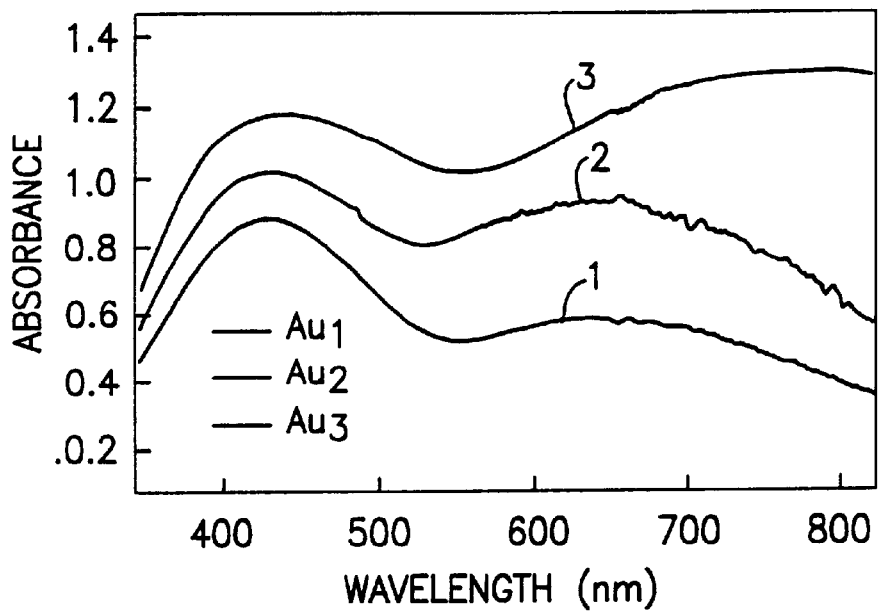
FIG. 46A shows the optical spectra of 14-nm diameter colloidal Au clad with Ag. Each spectrum has the same exposure time to Ag, but different amounts of Au particles with Au$_3$>Au$_2$>Au$_1$. The samples comprised monolayers of Au colloid on MPMDMS-coated glass slides.
Figure 46B:
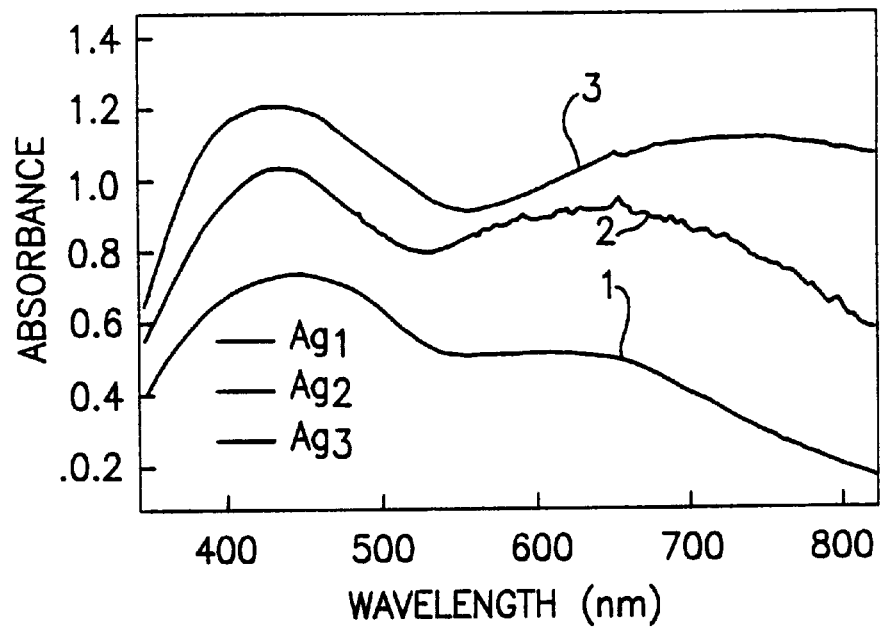
FIG. 46B shows the optical spectra of 14-nm colloidal Au clad with Ag. The spectrum of each of FIG. 46A and FIG. 46B has the same exposure time to Au, but different durations of Ag exposure with Ag3>Ag2>Ag$_1$. The samples comprised monolayers of Au colloid on MPMDMS-coated glass slides.
Figure 47A:
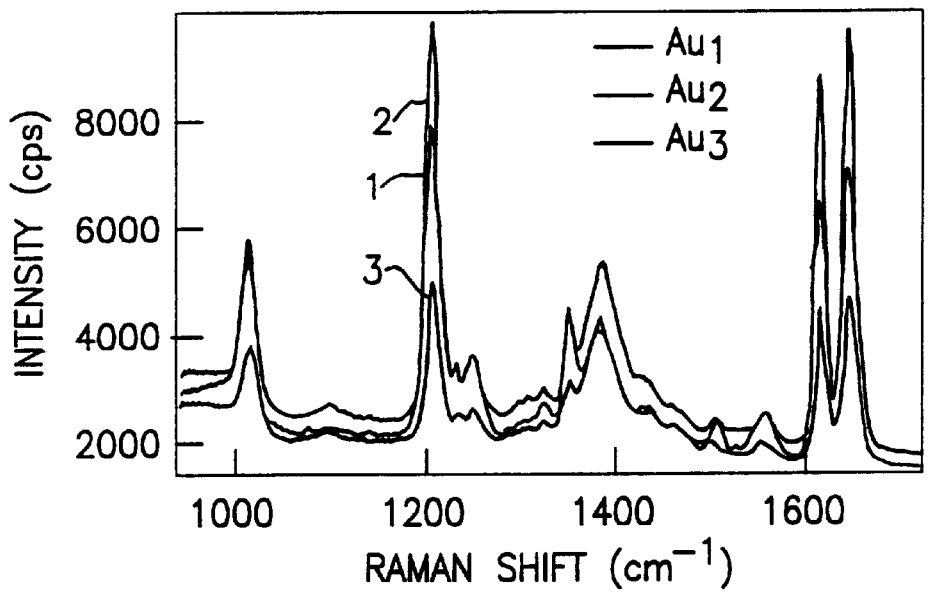
FIGS. 47A and 47B show SERS spectra for the samples shown in FIG. 46A and 46B, respectively. Experimental conditions: [BPE]=10 mM; 30 mW of 647.1-nm excitation; two collections of a 2- s integration, 5 cm$^{-1}$ band pass.
Figure 47B:
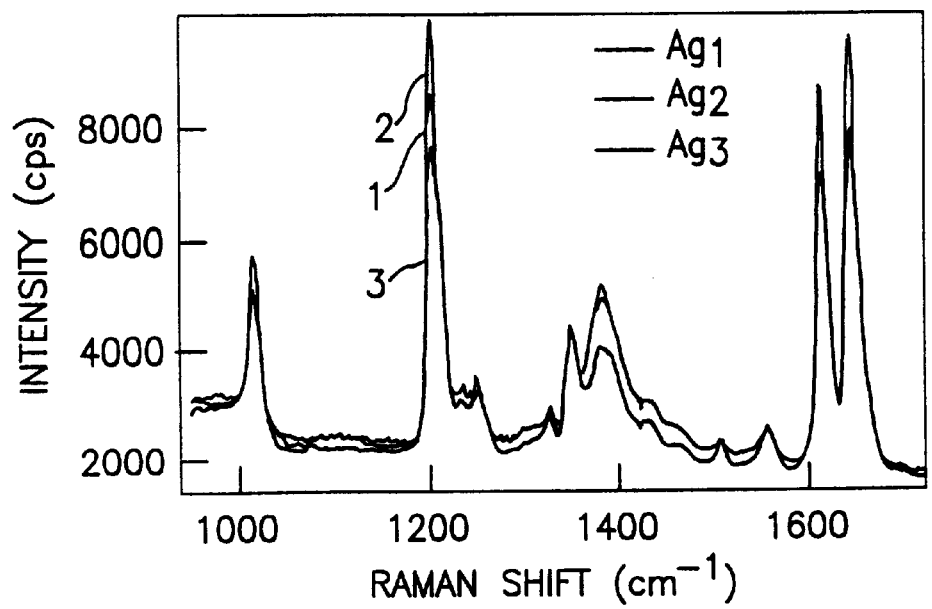
Figure 48A:
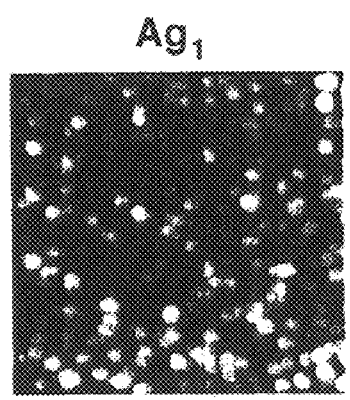
FIGS. 48A, 48B and 48C show AFM images (1 μm×1 μm, with 80 nm Z-scale) for the samples with varying Ag coverages described in FIGS. 46A and 46B, and FIGS. 47A and 47B.
Figure 48B:
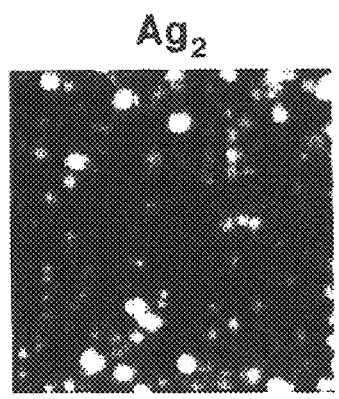
Figure 48C:
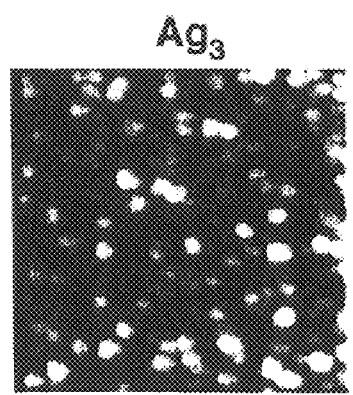

A stepped gradient synthetic protocol was prepared that allowed a 10×10 array of separate glass slides to be simultaneaouly derivatized and characterized. Using this apparatus, a 5×5 array was selected for further analysis. The 3D bar graph shown in FIG. 45 depicts particle coverage and height measurements from several AFM images collected from a 5×5 array of Ag-clad-Au samples. The Au particle diameter before exposure to Ag was 14 nm. Immersion times were chosen using previous combinatorial data as a guide. The Z-scale on the graph shows the number of particles/$\mu m^2$, reflecting the increasing Au particle coverage with exposure time. The number written on each bar is the average particle height on the sample, as determined by AFM section analysis. As expected, the particle height increases with continued Ag plating solution exposure.

Representative AFM images, uv-vis spectra, and SERS spectra from this data set are shown in FIGS. 46A and 46B, FIGS. 47A and 47B, FIGS. 48A, 48B and 48C and FIGS. 49A, 49B and 49C. For Ag$_1$, Ag$_2$, and Ag$_3$, the samples were exposed to colloidal Au for the same time, therefore differences in optical spectra and SERS intensity arise from different amounts of Ag cladding. All three optical spectra exhibit a typical Mie absorbance at ~430 nm for Ag, and a collective plasmon band (~650) indicating at least partial electronic coupling between particles. Similarly, for Au$_1$, Au$_2$, and Au$_3$, coverage of Ag is fixed. The data show that changes in SERS intensity from non-optimal Au colloid coverage are significantly more dramatic than those seen by varying the Ag cladding.

Figure 50A:
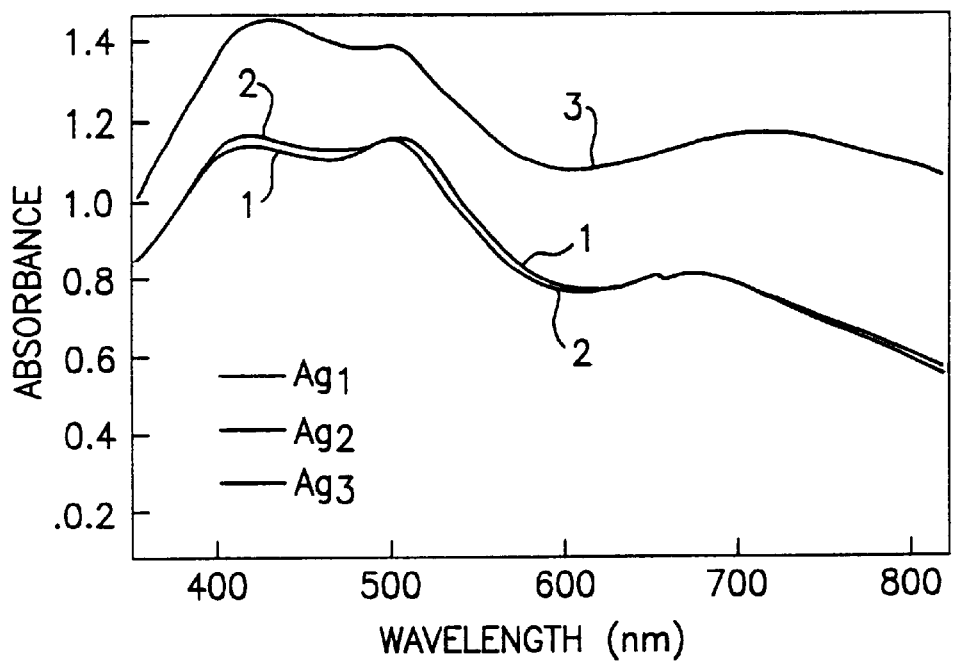
FIG. 50A shows the optical spectra of Ag-clad, 28-nm diameter colloidal Au monolayers on MPMDMS/glass (Ag$_3$>Ag2>Ag$_1$).
Figure 50B:
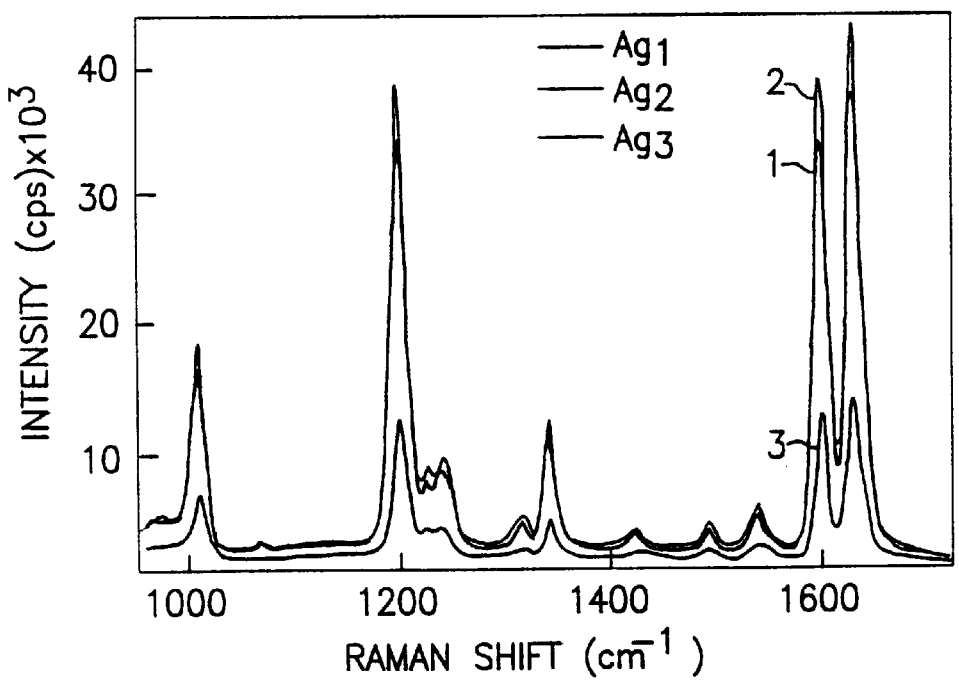
FIG. 50B shows SERS spectra for Ag-clad, 28-nm diameter colloidal Au monolayers on MPMDMS/glass. Experimental conditions for FIGS. 50A and 50B:[BPE]=10 mM; 30 mW of 647.1-nm excitation; two collections of a 2- s integration, 5 cm$^{-1}$ band pass.

In another example, images and spectra were collected from a combinatorial sample series using 28-nm diameter colloidal Au. Each sample was exposed to colloidal Au for the same amount of time. Total particle coverage needed to achieve high SERS signals is significantly lower when using larger colloid cores. Optical spectra exhibit an Au Mie resonance at ~530 nm in addition to the collective plasmon and Ag bands found in the Au/Ag optical spectra having smaller Au particles, as shown by FIGS. 50A and 50B. As shown, SERS intensity is significantly increased with larger Au cores (FIG. 50B). AFM for these samples are shown in FIGS. 51A, 51B and 51C.

The ability to vary surface nanostructure combinatorially from solution is extremely important for optimizing the surface characteristics of self-assembled metal colloid monolayers for SERS, surface plasmon resonance, sum frequency generation and electrochemistry, where substrate composition and topography are critical. The utility of this approach in materials synthesis is further augmented by the widespread availability of dispersible metal-containing nanoparticles and the numerous routes to metal deposition from complexed metal cations. Moreover, recently developed Raman imaging methods are intrinsically more efficient than the point-by-point mapping method described herein. With tunable filter imaging spectrometers and charge-coupled device detectors, it should be possible to simultaneously probe up to $10^6$ sample structures.

Thus is described my invention and the manner and process of making and using it in such full, clear, concise, and exact terms so as to enable any person skilled in the art to which it pertains, or with which it is most nearly connected, to make and use the same.

What is claimed is:

1. A metal colloid monolayer comprising a plurality of colloidal Ag clad Au nanoparticles surface confined on a substrate, said monolayer having a gradient of nanoparticle density in a first direction, and a gradient in particle size in a second direction perpendicular to said first direction.

2. The metal colloid monolayer of claim 1, wherein said nanoparticles are bound to said substrate by bonding with functional groups of a bifunctional organic film.

3. The metal colloid monolayer of claim 2, wherein said bifunctional organic film is selected from the group consisting of an organosilane, poly(allylamine) hydrochloride and biotin.

4. The metal colloid monolayer of claim 1, wherein said substrate is elected from the group consisting of glass, quartz, alumina, tin oxides and metals.

5. The metal colloid monolayer of claim 1, wherein said nanoparticles have a size of about 3 nm to about 100 nm.

6. A metal colloid monolayer comprising a plurality of colloidal Ag clad Au nanoparticles surface confined on a substrate, said monolayer having a gradient of nanoparticle density in a first direction, and a gradient in particle size in a second direction perpendicular to said first direction formed by:

coating a substrate with a bifunctional organic film;

immersing the coated substrate into a colloidal Au solution such that a first leading edge of said substrate is immersed in said colloidal Au solution for a longer period of time relative to a first trailing edge to provide a monolayer of Au nanoparticles having a decreasing level of coverage from said first leading edge to said first trailing edge;

withdrawing said substrate from said colloidal Au solution;

rotating said substrate through an angle of about 90°;

immersing the substrate provided with the monolayer of Au nanoparticles in an $Ag^+$ solution such that a second leading edge of said substrate is immersed in said $Ag^+$ solution for a longer period of time relative to a second trailing edge to provide a monolayer of Au nanoparticles having a decreasing level of Ag cladding thickness from said second leading edge to said second trailing edge; and withdrawing said substrate from said $Ag^+$ solution.

7. The metal colloid monolayer of claim 6, wherein said nanoparticles are bound to said substrate by bonding with functional groups of a bifunctional organic film.

8. The metal colloid monolayer of claim 7, wherein said bifunctional organic film is selected from the group consisting of an organosilane, poly(allylamine) hydrochloride and biotin.

9. The metal colloid monolayer of claim 6, wherein said substrate is selected from the group consisting of glass, quartz, alumina, tin oxides and metals.

10. The metal colloid monolayer of claim 6, wherein said Au nanoparticles, prior to cladding, have a uniform size of about 3nm to about 100 nm.

11. A method of determining optimal surface characteristics of a metal colloid monolayer comprising a plurality of colloidal Ag clad Au nanoparticles surface confined on a substrate for use in an analytical procedure, said method comprising:

coating a substrate with a bifunctional organic film;

immersing the coated substrate into a colloidal Au solution such that a first leading edge of said substrate is immersed in said colloidal Au solution for a longer period of time relative to a first trailing edge to provide a monolayer of Au nanoparticles having a decreasing level of coverage from said first leading edge to said first trailing edge;

withdrawing said substrate from said colloidal Au solution;

rotating said substrate through an angle of about 90°;

immersing the substrate provided with the monolayer of Au nanoparticles in an $Ag^+$ solution such that a second leading edge of said substrate is immersed in said $Ag^+$ solution for a longer period of time relative to a second trailing edge to provide a monolayer of Au nanoparticles having a decreasing level of Ag cladding thickness from said second leading edge to said second trailing edge;

withdrawing said substrate from said $Ag^+$ to form a monolayer having a gradient of nanoparticle density in one direction, and a gradient in particle size in another direction;

using the gradated monolayer for an analytical procedure; and analyzing the results achieved at different regions of said gradated monolayer to determine a nanoparticle coverage and particle size that provides an optimal result.

12. The method of claim 11, wherein said monolayer is a surface enhanced Raman scattering response substrate.

13. The method of claim 11, wherein said monolayer is a biosensor for detecting the presence of a biological ligand.

* * * * *